(12) United States Patent
Shigemori et al.

(10) Patent No.: US 7,713,700 B2
(45) Date of Patent: May 11, 2010

(54) METHOD OF AMPLIFYING NUCLEIC ACIDS, REAGENT KIT FOR AMPLIFYING NUCLEIC ACIDS, METHOD OF DETECTING SINGLE NUCLEOTIDE POLYMORPHISM, AND REAGENT KIT FOR DETECTING SINGLE NUCLEOTIDE POLYMORPHISM

(75) Inventors: Yasushi Shigemori, Kariya (JP); Takehiko Shibata, Wako (JP); Tsutomu Mikawa, Wako (JP); Michio Oishi, Kisarazu (JP); Osamu Ohara, Kisarazu (JP)

(73) Assignees: Aisin Cosmos R&D Co., Ltd., Kariya-Shi, Aichi (JP); Riken, Wako-Shi, Saitama (JP); Kazusa DNA Research Institute, Kisarazu-Shi, Chiba (JP)

( * ) Notice: Subject to any disclaimer, the term of this patent is extended or adjusted under 35 U.S.C. 154(b) by 0 days.

(21) Appl. No.: 12/062,215

(22) Filed: Apr. 3, 2008

(65) Prior Publication Data

US 2008/0206775 A1    Aug. 28, 2008

Related U.S. Application Data

(60) Division of application No. 11/081,949, filed on Mar. 17, 2005, now abandoned, which is a continuation of application No. PCT/JP03/11752, filed on Sep. 12, 2003.

(30) Foreign Application Priority Data

Sep. 17, 2002   (JP)   ............... 2002-269645

(51) Int. Cl.
   *C12Q 1/68*   (2006.01)
(52) U.S. Cl. ............. 435/6; 435/91.1; 435/91.2
(58) Field of Classification Search ............... None
   See application file for complete search history.

(56) References Cited

U.S. PATENT DOCUMENTS

| | | | |
|---|---|---|---|
| 5,223,414 | A | 6/1993 | Zarling et al. |
| 5,510,473 | A | 4/1996 | Camerini-Otero et al. |
| 2005/0136443 | A1 | 6/2005 | Shigemori |
| 2005/0214753 | A1* | 9/2005 | Shultz et al. ............... 435/6 |

FOREIGN PATENT DOCUMENTS

| | | |
|---|---|---|
| JP | 3010738 | 12/1999 |
| WO | WO 91/17267 | 11/1991 |
| WO | WO 00/43540 | 7/2000 |

OTHER PUBLICATIONS

Newton et al. Nucleic Acids Research vol. 17:2503-2516. 1989.*

Kato et al., "Observation of RecA protein monomer by small angle X-ray scattering with synchrotron radiation," *FEBS Letters*, 2000, vol. 482, pp. 159-162, Elsevier Science, B.V., London, England.

Wetmur et al., "Cloning, Sequencing, and Expression of RecA Proteins from Three Distantly Related Thermophilic Eubacteria," *The Journal of Biological Chemistry*, 1994, vol. 269, No. 41, pp. 25928-25935, The American Society for Biochemistry and Molcular Biology, Inc., Baltimore, Maryland.

Kato et al., "Characterization of thermostable RecA protein and analysis of its interaction with single-stranded DNA," *Eur. J. Biochem.*, 1999, vo. 259, pp. 592-601, Blackwell Science, Berlin, Germany.

Tombline et al., "Heterogeneity of primer extension products in asymmetric PCR is due both to cleavage by a structure-specific exo/endonuclease activity of DNA polymerases and to premature stops," *Proc. Natl. Acad. Sci., USA*, 1996, vol. 93, pp. 2724-2728, National Academy of Sciences, Washington, D.C.

Shigemori et al., "Multiplex PCR: use of heat-stable *Thermus thermophilus* RecA protein to minimize non-specific PCR products," *Nucleic Acids Research*, 2005, vol. 33, No. 14, Oxford University Press, Oxford, England.

Angov et al., "The *recA* Gene from the Thermophile *Thermus aquaticus* YT-1: Cloning, Expression, and Characterization," *Journal of Bacteriology*, 1994, vol. 175, No. 5, pp. 1405-1412, American Society for Microbiology, Washington, D.C.

Schwarz et al., "Improved yields of long PCR products using gene 32 protein," *Nucleic Acids Research*, 1990, vol. 18, No. 4, p. 1079, Oxford University Press, Oxford, England.

Elnifro et al., "Multiplex PCR: Optimization and Application in Diagnostic Virology," *Clinical Microbiology Reviews*, 2000, vol. 13, No. 4, pp. 559-570, American Society for Microbiology, Washington, D.C.

Kato et al., "RecA Protein from an Extremely Thermophilic Bacterium, *Thermus thermophilus* HB8," *J. Biochem.*, 1993, vol. 114, pp. 926-929.

* cited by examiner

*Primary Examiner*—Heather G Calamita
(74) *Attorney, Agent, or Firm*—Buchanan Ingersoll & Rooney PC

(57) ABSTRACT

An object of the present invention is to provide a nucleic acid amplification method for amplifying a desired nucleic acid while suppressing amplification of byproducts in a PCR reaction, a reagent kit used for nucleic acid amplification, a method of detecting single nucleotide polymorphism to detect single nucleotide polymorphism by utilizing that amplification of byproducts is suppressed in a PCR reaction, and a reagent kit used for detecting single nucleotide polymorphism. The method of amplifying nucleic acids by PCR is characterized by admixing in a reaction solution, a homologous recombinant protein which contains at least one of a RecA protein derived from *Thermus thermophilus*, and a modified RecA protein obtained by modification of the RecA protein and having a function similar to that of the RecA protein, and carrying out PCR.

6 Claims, 47 Drawing Sheets

FIG.2
(A)
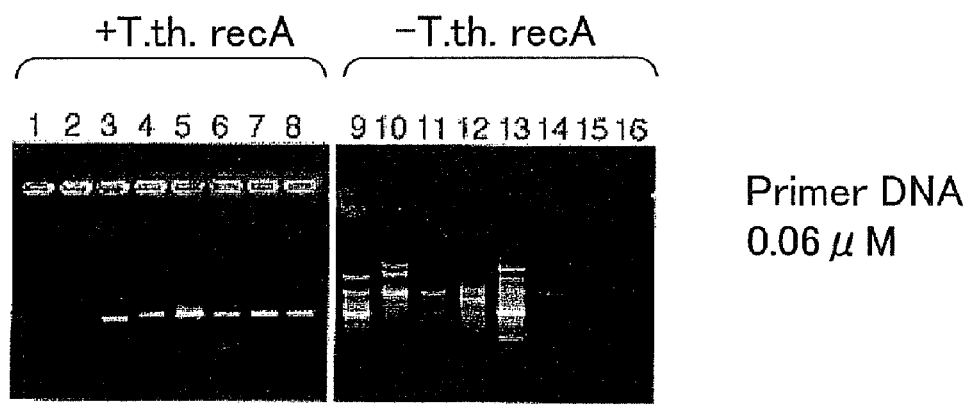
Primer DNA
0.06 μM
(B)
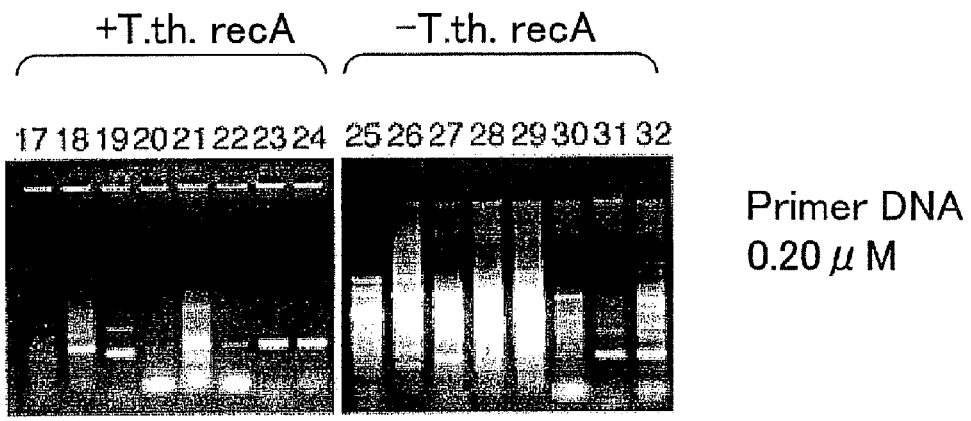
Primer DNA
0.20 μM

FIG.7
(A)
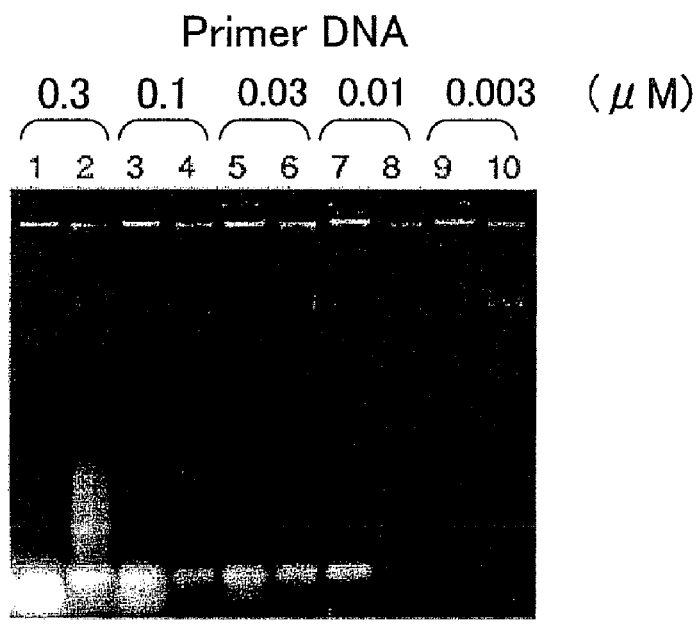
(B)
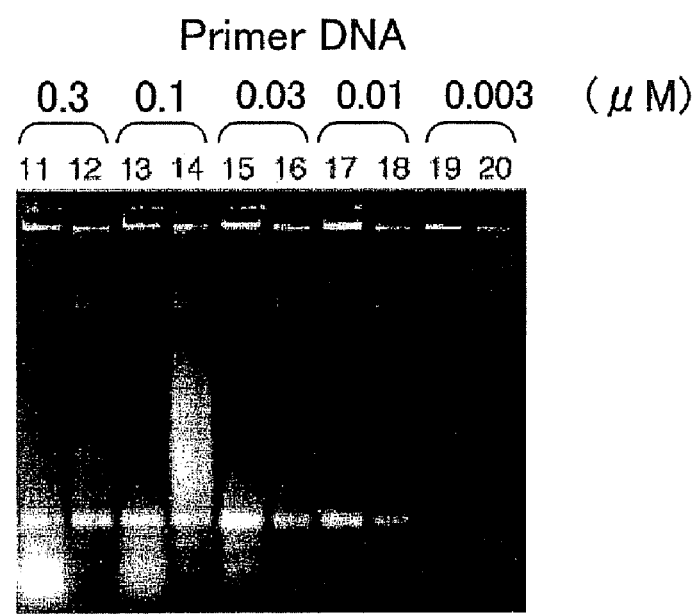

FIG.8
(A)
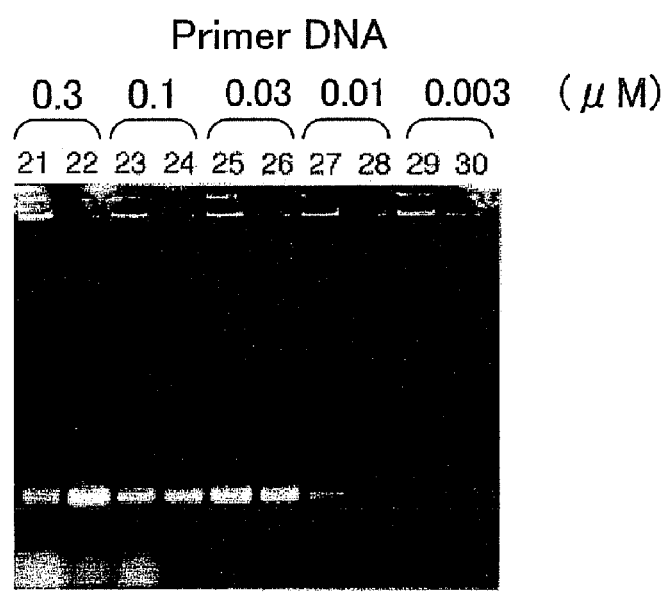
(B)
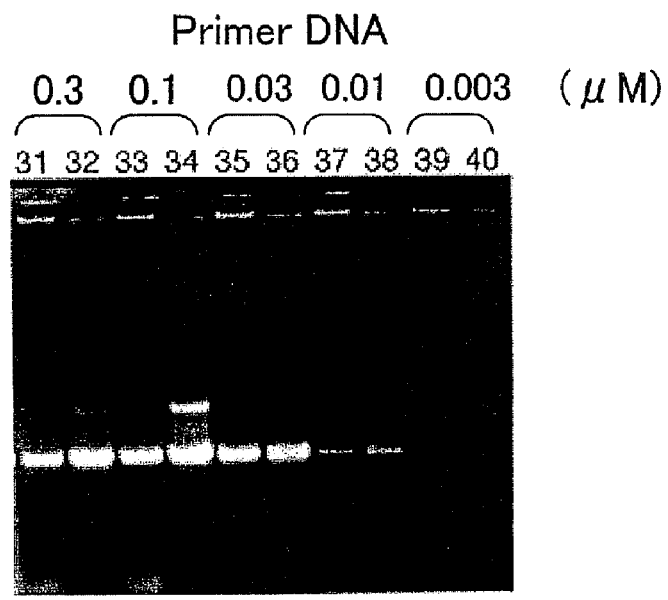

FIG.13
(A)
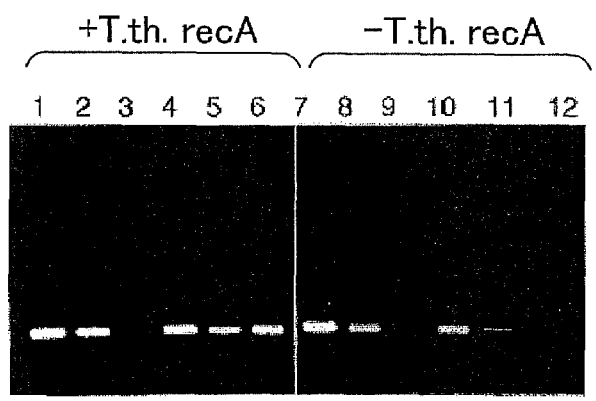
Annealing temperature: 60°C
(B)
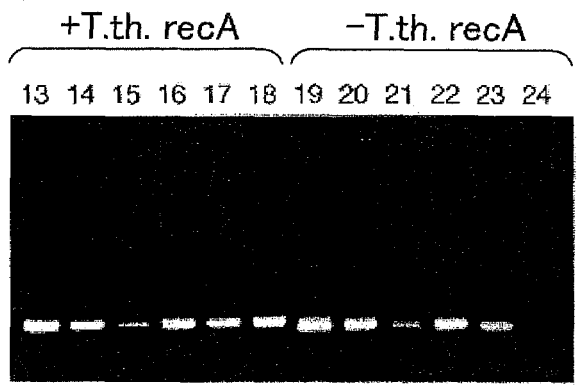
Annealing temperature: 55°C

FIG. 14
(A)
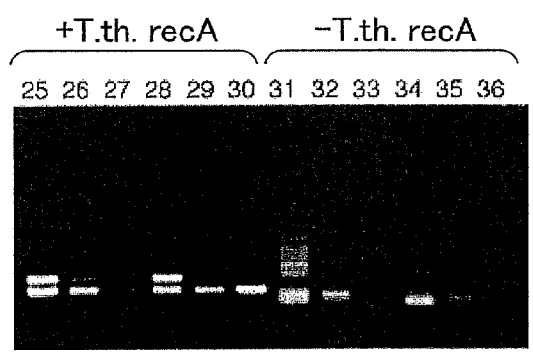
Annealing temperature: 50°C
(B)
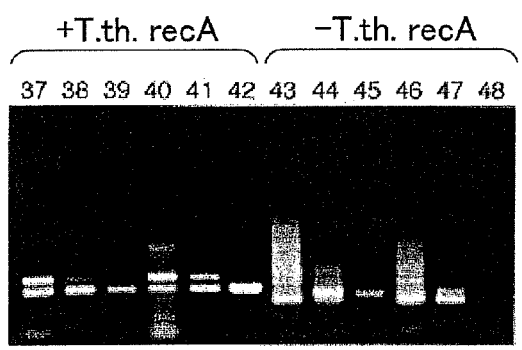
Annealing temperature: 45°C

FIG.16
(A)
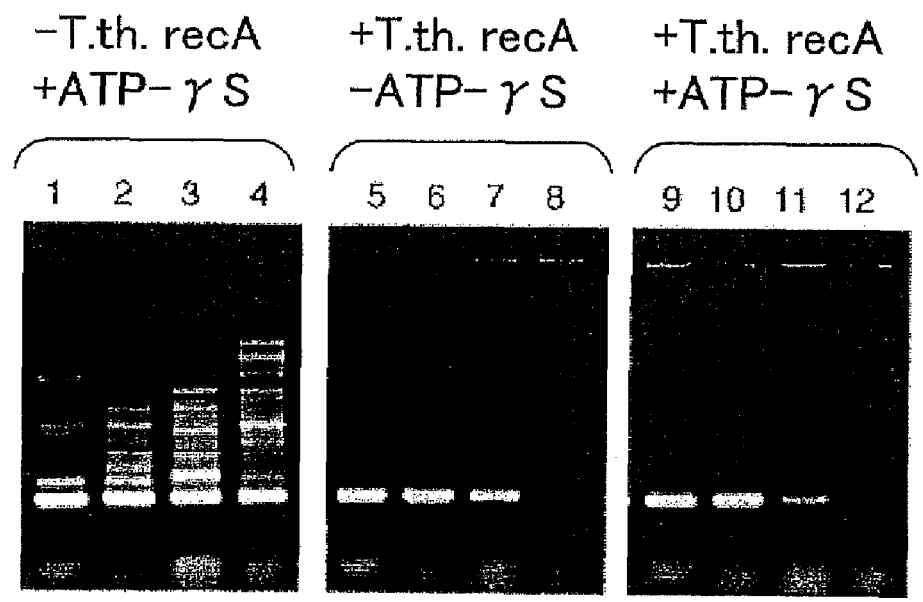
(B)
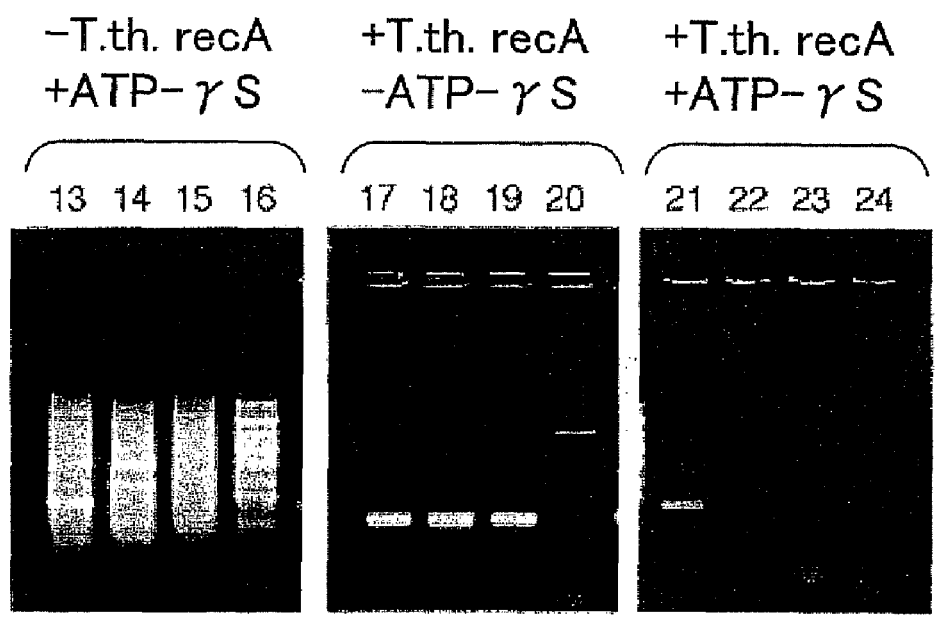

FIG.17
(A)
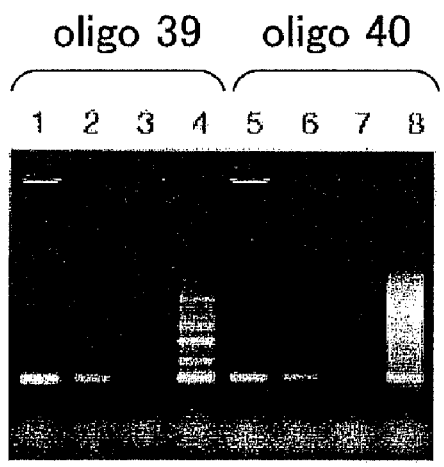
(B)
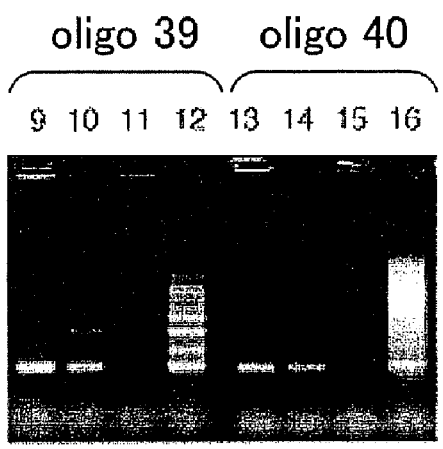
The primer DNAs were added after the first 1 cycle of the reaction

FIG.18
(A)
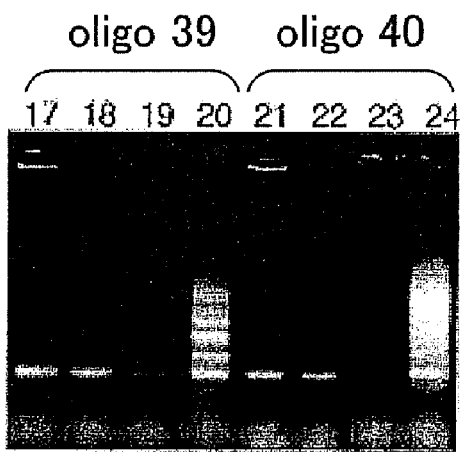
The primer DNAs were added after the first 3 cycle of the reaction
(B)
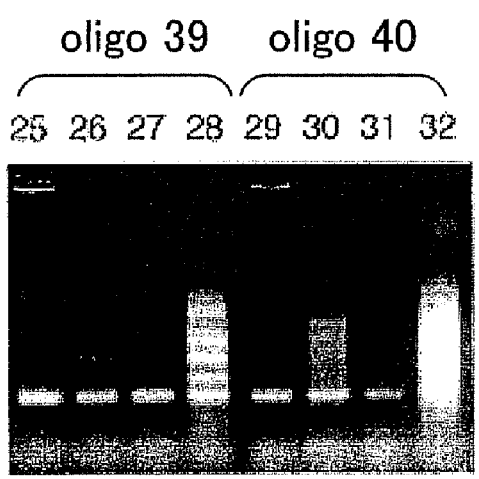
The primer DNAs were added after the first 6 cycle of the reaction

FIG.19
(A)
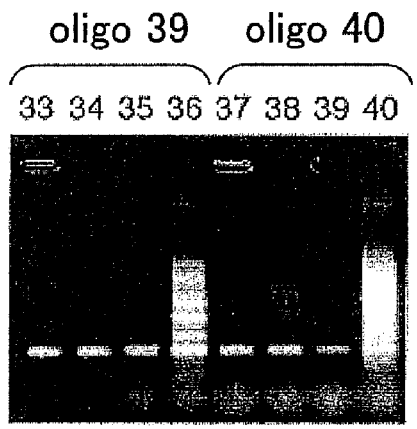
The primer DNAs were added after the first 10 cycle of the reaction
(B)
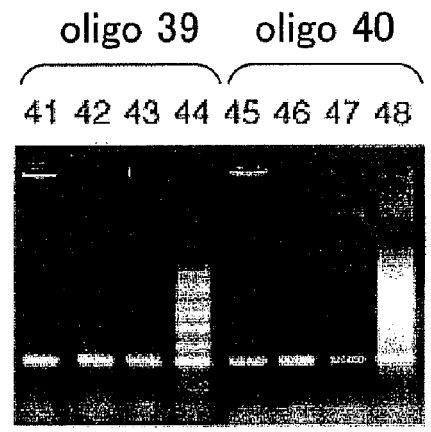
The primer DNAs were added after the first 15 cycle of the reaction

FIG.20
(A)
Initial denaturation condition : 70°C for 10 minutes
(B)
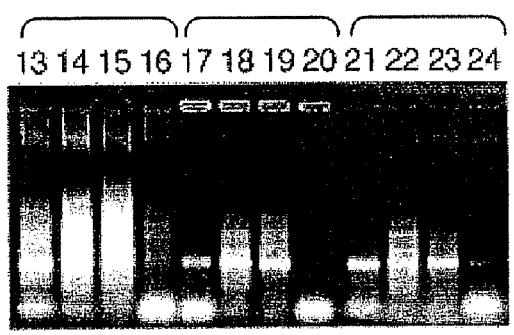
Initial denaturation condition : 80°C for 10 minutes FIG.37

FIG.47
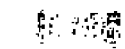
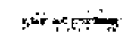
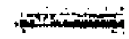
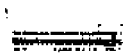
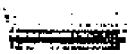
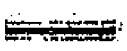

SEQUENCE LISTING

```
<160> NUMBER OF SEQ ID NOS: 132

<210> SEQ ID NO 1
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens PAC clone RP5-852P6 from 7p11.2-p21,
      complete sequence (ACCESSION AC006454)

<400> SEQUENCE: 1
ggtgcactcc atcatgctta                                               20

<210> SEQ ID NO 2
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens PAC clone RP5-852P6 from 7p11.2-p21,
      complete sequence (ACCESSION AC006454)
```

```
<400> SEQUENCE: 2
catcagtcag aggggctcac                                          20

<210> SEQ ID NO 3
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens PAC clone RP5-852P6 from 7p11.2-p21,
      complete sequence (ACCESSION AC006454)

<400> SEQUENCE: 3
cccacatccc tggcaggaat                                          20

<210> SEQ ID NO 4
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens PAC clone RP5-852P6 from 7p11.2-p21,
      complete sequence (ACCESSION AC006454)

<400> SEQUENCE: 4
tgcaggtgtg ggcctagctg                                          20

<210> SEQ ID NO 5
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens PAC clone RP5-852P6 from 7p11.2-p21,
      complete sequence (ACCESSION AC006454)

<400> SEQUENCE: 5
tgtcctgggc cccagcagga                                          20

<210> SEQ ID NO 6
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens PAC clone RP5-852P6 from 7p11.2-p21,
      complete sequence (ACCESSION AC006454)

<400> SEQUENCE: 6
ggggtcttgc tgtgggcagg                                          20

<210> SEQ ID NO 7
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens PAC clone RP5-852P6 from 7p11.2-p21,
      complete sequence (ACCESSION AC006454)

<400> SEQUENCE: 7
gagatgcccc cccatactgc                                          20

<210> SEQ ID NO 8
<211> LENGTH: 20
<212> TYPE: DNA
<213> ORGANISM: Artificial Sequence
```

```
<220> FEATURE:
<223> OTHER INFORMATION: synthesize oligonucleotide by referring to Homo
      sapiens PAC clone RP5-852P6 from 7p11.2-p21,
      complete sequence (ACCESSION AC006454)

<400> SEQUENCE: 8
atctgtcccc tctcctcctg                                                    20

<210> SEQ ID NO 9
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens PAC clone RP5-852P6 from 7p11.2-p21,
      complete sequence (ACCESSION AC006454)

<400> SEQUENCE: 9
aggtgtgcag agtgcaaagc                                                    20

<210> SEQ ID NO 10
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens PAC clone RP5-852P6 from 7p11.2-p21,
      complete sequence (ACCESSION AC006454)

<400> SEQUENCE: 10
gcttcaaggc agaggccagg                                                    20

<210> SEQ ID NO 11
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens PAC clone RP5-852P6 from 7p11.2-p21,
      complete sequence (ACCESSION AC006454)

<400> SEQUENCE: 11
tccaggtggc ccccaagcag                                                    20

<210> SEQ ID NO 12
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens PAC clone RP5-852P6 from 7p11.2-p21,
      complete sequence (ACCESSION AC006454)

<400> SEQUENCE: 12
atctctcttg ccttggggtg                                                    20

<210> SEQ ID NO 13
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens PAC clone RP5-852P6 from 7p11.2-p21,
      complete sequence (ACCESSION AC006454)

<400> SEQUENCE: 13
gtgtgctggg aggaggggcc                                                    20
```

```
<210> SEQ ID NO 14
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens PAC clone RP5-852P6 from 7p11.2-p21,
      complete sequence (ACCESSION AC006454)

<400> SEQUENCE: 14
gtcactaaac aggggctcaa                                              20

<210> SEQ ID NO 15
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens PAC clone RP5-852P6 from 7p11.2-p21,
      complete sequence (ACCESSION AC006454)

<400> SEQUENCE: 15
cgtgtgggag gagcaggcag                                              20

<210> SEQ ID NO 16
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens PAC clone RP5-852P6 from 7p11.2-p21,
      complete sequence (ACCESSION AC006454)

<400> SEQUENCE: 16
gccagaatgt tcccctggag                                              20

<210> SEQ ID NO 17
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens BAC clone RP11-16P10 from 7, complete
      sequence (ACCESSION AC093734 AC 011786)

<400> SEQUENCE: 17
cgggtgcaca caaaggctgg                                              20

<210> SEQ ID NO 18
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens BAC clone RP11-16P10 from 7, complete
      sequence (ACCESSION AC093734 AC 011786)

<400> SEQUENCE: 18
tctctggcca ggtgcctggc                                              20

<210> SEQ ID NO 19
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens BAC clone RP11-16P10 from 7, complete
      sequence (ACCESSION AC093734 AC 011786)
```

<400> SEQUENCE: 19
cgccccgaca accctgaccc                                              20

<210> SEQ ID NO 20
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens BAC clone RP11-16P10 from 7, complete
      sequence (ACCESSION AC093734 AC 011786)

<400> SEQUENCE: 20
cttgggaaga tcctgagact                                              20

<210> SEQ ID NO 21
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens BAC clone RP11-16P10 from 7, complete
      sequence (ACCESSION AC093734 AC 011786)

<400> SEQUENCE: 21
tcggtaaacg ctggctcccg                                              20

<210> SEQ ID NO 22
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens BAC clone RP11-16P10 from 7, complete
      sequence (ACCESSION AC093734 AC 011786)

<400> SEQUENCE: 22
caaaacgccc cccaccgccc                                              20

<210> SEQ ID NO 23
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens BAC clone RP11-16P10 from 7, complete
      sequence (ACCESSION AC093734 AC 011786)

<400> SEQUENCE: 23
ggtttaccag cacctgggga                                              20

<210> SEQ ID NO 24
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens BAC clone RP11-16P10 from 7, complete
      sequence (ACCESSION AC093734 AC 011786)

<400> SEQUENCE: 24
cccatcgtgg tctagcgggat                                             20

<210> SEQ ID NO 25
<211> LENGTH: 20
<212> TYPE: DNA

```
<213> ORGANISM: Artificial Sequence
<220> FEATURE:
<223> OTHER INFORMATION: synthesize oligonucleotide by referring to Homo
      sapiens BAC clone RP11-16P10 from 7, complete
      sequence (ACCESSION AC093734 AC 011786)

<400> SEQUENCE: 25
gaagtggccc ggaagacggt                                                   20

<210> SEQ ID NO 26
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens BAC clone RP11-16P10 from 7, complete
      sequence (ACCESSION AC093734 AC 011786)

<400> SEQUENCE: 26
gcagcgccct tcccacccct                                                   20

<210> SEQ ID NO 27
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens BAC clone RP11-16P10 from 7, complete
      sequence (ACCESSION AC093734 AC 011786)

<400> SEQUENCE: 27
gcacacgcct tgtagacagc                                                   20

<210> SEQ ID NO 28
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens BAC clone RP11-16P10 from 7, complete
      sequence (ACCESSION AC093734 AC 011786)

<400> SEQUENCE: 28
ctgattctcc agggtgggct                                                   20

<210> SEQ ID NO 29
<211> LENGTH: 22
<212> TYPE: DNA
<213> ORGANISM: Artificial Sequence
<220> FEATURE:
<223> OTHER INFORMATION: synthesize oligonucleotide by referring to
      Human DNA sequence from clone RP5-1013A22 on chromosome 20
      Contains the HNF4A (hepatic nuclear factor 4, alpha) gene, part of
      a novel gene encoding a protein similar to cellular
      retinaldehyde-binding protein, a RPL37A (ribosomal protein L37A)
      psudogene, parts of 2 novel genes, ESTs, STSs and
      GSSs, complete sequence (ACCESSION AL132772)

<400> SEQUENCE: 29
gcatctgggg cctgggattt ag                                                22

<210> SEQ ID NO 30
<211> LENGTH: 25
<212> TYPE: DNA
<213> ORGANISM: Artificial Sequence
<220> FEATURE:
<223> OTHER INFORMATION: synthesize oligonucleotide by referring to
      Human DNA sequence from clone RP5-1013A22 on chromosome 20
      Contains the HNF4A (hepatic nuclear factor 4, alpha) gene, part of
``` a novel gene encoding a protein similar to cellular
retinaldehyde-binding protein, a RPL37A (ribosomal protein L37A)
psudogene, parts of 2 novel genes, ESTs, STSs and
GSSs, complete sequence (ACCESSION AL132772)

<400> SEQUENCE: 30
tacaaggcag gcatcatgac tcacg                                      25

<210> SEQ ID NO 31
<211> LENGTH: 21
<212> TYPE: DNA
<213> ORGANISM: Artificial Sequence
<220> FEATURE:
<223> OTHER INFORMATION: synthesize oligonucleotide by referring to Homo
      sapiens 3q BAC RP11-529F4 (Roswell Park Cancer
      Institute Human BAC Library) complete sequence
      (ACCESSION AC080007)

<400> SEQUENCE: 31
aggagcttag gaggggagg t                                           21

<210> SEQ ID NO 32
<211> LENGTH: 23
<212> TYPE: DNA
<213> ORGANISM: Artificial Sequence
<220> FEATURE:
<223> OTHER INFORMATION: synthesize oligonucleotide by referring to Homo
      sapiens 3q BAC RP11-529F4 (Roswell Park Cancer
      Institute Human BAC Library) complete sequence
      (ACCESSION AC080007)

<400> SEQUENCE: 32
cattgacagg acaggagaag gga                                        23

<210> SEQ ID NO 33
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens genomic beta globin region (HBB alpha) on
      chromosome 11 (ACCESSION NG_000007)

<400> SEQUENCE: 33 cttttgttc ccccagacac tc                                          22

<210> SEQ ID NO 34
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens genomic beta globin region (HBB alpha) on
      chromosome 11 (ACCESSION NG_000007)

<400> SEQUENCE: 34
gcactggctt aggagttgga ct                                         22

<210> SEQ ID NO 35
<211> LENGTH: 24
<212> TYPE: DNA
<213> ORGANISM: Artificial Sequence
<220> FEATURE:
<223> OTHER INFORMATION: synthesize oligonucleotide by referring to Homo
      sapiens HPFH60R gene for olfactory receptor
      (ACCESSION X81445 X91835)

<400> SEQUENCE: 35

```
gttaataacct aaggctctac tgca                                          24
```

<210> SEQ ID NO 36
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens HPFH60R gene for olfactory receptor
      (ACCESSION X81445 X91835)

<400> SEQUENCE: 36

```
aggcaatggc ggcacccatc                                                20
```

<210> SEQ ID NO 37
<211> LENGTH: 21
<212> TYPE: DNA
<213> ORGANISM: Artificial Sequence
<220> FEATURE:
<223> OTHER INFORMATION: synthesize oligonucleotide by referring to Homo
      sapiens PAC clone RP5-1142J19 from 7q35-q36,
      complete sequence (ACCESSION AC004975)

<400> SEQUENCE: 37

```
gcaggcacca agaactactg c                                              21
```

<210> SEQ ID NO 38
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens PAC clone RP5-1142J19 from 7q35-q36,
      complete sequence (ACCESSION AC004975)

<400> SEQUENCE: 38

```
gcctaaggtc acgttgtccc                                                20
```

<210> SEQ ID NO 39
<211> LENGTH: 21
<212> TYPE: DNA
<213> ORGANISM: Artificial Sequence
<220> FEATURE:
<223> OTHER INFORMATION: synthesize oligonucleotide by referring to Homo
      sapiens PAC clone RP5-1142J19 from 7q35-q36,
      complete sequence (ACCESSION AC004975)

<400> SEQUENCE: 39

```
gcaggcacca ggaactactg c                                              21
```

<210> SEQ ID NO 40
<211> LENGTH: 21
<212> TYPE: DNA
<213> ORGANISM: Artificial Sequence
<220> FEATURE:
<223> OTHER INFORMATION: synthesize oligonucleotide by referring to Homo
      sapiens PAC clone RP5-1142J19 from 7q35-q36,
      complete sequence (ACCESSION AC004975)

<400> SEQUENCE: 40

```
gcaggcgcca ggaagtactg c                                              21
```

<210> SEQ ID NO 41
<211> LENGTH: 21
<212> TYPE: DNA
<213> ORGANISM: Artificial Sequence
<220> FEATURE:
<223> OTHER INFORMATION: synthesize oligonucleotide by referring to Homo -continued sapiens PAC clone RP5-1142J19 from 7q35-q36,
complete sequence (ACCESSION AC004975)

<400> SEQUENCE: 41
gcgggcgcca ggaagtacgg c                                              21

<210> SEQ ID NO 42
<211> LENGTH: 21
<212> TYPE: DNA
<213> ORGANISM: Artificial Sequence
<220> FEATURE:
<223> OTHER INFORMATION: synthesize oligonucleotide by referring to Homo
      sapiens PAC clone RP5-1142J19 from 7q35-q36,
      complete sequence (ACCESSION AC004975)

<400> SEQUENCE: 42
gcaggcacca agaactactg c                                              21

<210> SEQ ID NO 43
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens PAC clone RP5-1142J19 from 7q35-q36,
      complete sequence (ACCESSION AC004975)

<400> SEQUENCE: 43
gcctaaggtc acgttgtccc                                                20

<210> SEQ ID NO 44
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens PAC clone RP5-852P6 from 7p11.2-p21,
      complete sequence (ACCESSION AC006454)

<400> SEQUENCE: 44
catggcacct gctctgagac                                                20

<210> SEQ ID NO 45
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens PAC clone RP5-852P6 from 7p11.2-p21,
      complete sequence (ACCESSION AC006454)

<400> SEQUENCE: 45
ggcactttgt gcctctctcc                                                20

<210> SEQ ID NO 46
<211> LENGTH: 18
<212> TYPE: DNA
<213> ORGANISM: Artificial Sequence
<220> FEATURE:
<223> OTHER INFORMATION: synthesize oligonucleotide by referring to Homo
      sapiens PAC clone RP5-912I13 from 7, complete
      sequence (ACCESSION AC008060)

<400> SEQUENCE: 46
ccgagtcgca tgggtgag                                                  18

<210> SEQ ID NO 47

<210> SEQ ID NO 47
<211> LENGTH: 20
<212> TYPE: DNA
<213> ORGANISM: Artificial Sequence
<220> FEATURE:
<223> OTHER INFORMATION: synthesize oligonucleotide by referring to Homo sapiens PAC clone RP5-912I13 from 7, complete sequence (ACCESSION AC008060)

<400> SEQUENCE: 47
tttgtgcaag gaattgtggg        20

<210> SEQ ID NO 48
<211> LENGTH: 20
<212> TYPE: DNA
<213> ORGANISM: Artificial Sequence
<220> FEATURE:
<223> OTHER INFORMATION: synthesize oligonucleotide by referring to Homo sapiens BAC clone RP11-16P10 from 7, complete sequence (ACCESSION AC093734 AC011786)

<400> SEQUENCE: 48
atctgtgtgg ttcggctctg        20

<210> SEQ ID NO 49
<211> LENGTH: 20
<212> TYPE: DNA
<213> ORGANISM: Artificial Sequence
<220> FEATURE:
<223> OTHER INFORMATION: synthesize oligonucleotide by referring to Homo sapiens BAC clone RP11-16P10 from 7, complete sequence (ACCESSION AC093734 AC011786)

<400> SEQUENCE: 49
ctcccttaac agcagcctcc        20

<210> SEQ ID NO 50
<211> LENGTH: 22
<212> TYPE: DNA
<213> ORGANISM: Artificial Sequence
<220> FEATURE:
<223> OTHER INFORMATION: synthesize oligonucleotide by referring to Homo sapiens BAC clone CTB-135C18 from 7q11.2-q22, complete sequence (ACCESSION AC005164)

<400> SEQUENCE: 50
caaagctact ttcacagcct cc        22

<210> SEQ ID NO 51
<211> LENGTH: 22
<212> TYPE: DNA
<213> ORGANISM: Artificial Sequence
<220> FEATURE:
<223> OTHER INFORMATION: synthesize oligonucleotide by referring to Homo sapiens BAC clone CTB-135C18 from 7q11.2-q22, complete sequence (ACCESSION AC005164)

<400> SEQUENCE: 51
ggcatattca gccaaggatt tc        22

<210> SEQ ID NO 52
<211> LENGTH: 20
<212> TYPE: DNA
<213> ORGANISM: Artificial Sequence
<220> FEATURE:
<223> OTHER INFORMATION: synthesize oligonucleotide by referring to Homo sapiens PAC clone RP5-852P6 from 7p11.2-p21, complete sequence (ACCESSION AC006454)

<400> SEQUENCE: 52
tttctggaag ggactgggtc                                             20

<210> SEQ ID NO 53
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens PAC clone RP5-852P6 from 7p11.2-p21,
      complete sequence (ACCESSION AC006454)

<400> SEQUENCE: 53
tcccaggatc catggagaag                                             20

<210> SEQ ID NO 54
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens BAC clone CTB-135C18 from 7q11.2-q22,
      complete sequence (ACCESSION AC005164)

<400> SEQUENCE: 54
caaagctact ttcacagcct cc                                          22

<210> SEQ ID NO 55
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens BAC clone CTB-135C18 from 7q11.2-q22,
      complete sequence (ACCESSION AC005164)

<400> SEQUENCE: 55
ggcatattca gccaaggatt tc                                          22

<210> SEQ ID NO 56
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens BAC clone CTB-135C18 from 7q11.2-q22,
      complete sequence (ACCESSION AC005164)

<400> SEQUENCE: 56
caaagctact tgcacagcct cc                                          22

<210> SEQ ID NO 57
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens BAC clone CTB-135C18 from 7q11.2-q22,
      complete sequence (ACCESSION AC005164)

<400> SEQUENCE: 57
caaagctgct tgcacggcct cc                                          22

<210> SEQ ID NO 58
<211> LENGTH: 22
<212> TYPE: DNA
<213> ORGANISM: Artificial Sequence
<220> FEATURE:

```
<223> OTHER INFORMATION: synthesize oligonucleotide by referring to Homo
      sapiens BAC clone CTB-135C18 from 7q11.2-q22,
      complete sequence (ACCESSION AC005164)

<400> SEQUENCE: 58
caaggctgct tgcacggccg cc                                              22

<210> SEQ ID NO 59
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens BAC clone CTB-135C18 from 7q11.2-q22,
      complete sequence (ACCESSION AC005164)

<400> SEQUENCE: 59
caaagctact tgcacagcct cc                                              22

<210> SEQ ID NO 60
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens BAC clone CTB-135C18 from 7q11.2-q22,
      complete sequence (ACCESSION AC005164)

<400> SEQUENCE: 60
ggcatattca gccaaggatt tc                                              22

<210> SEQ ID NO 61
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens BAC clone CTB-135C18 from 7q11.2-q22,
      complete sequence (ACCESSION AC005164)

<400> SEQUENCE: 61
caaagctact ttcacagcct cc                                              22

<210> SEQ ID NO 62
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens BAC clone CTB-135C18 from 7q11.2-q22,
      complete sequence (ACCESSION AC005164)

<400> SEQUENCE: 62
caaagctact tacacagcct cc                                              22

<210> SEQ ID NO 63
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens BAC clone CTB-135C18 from 7q11.2-q22,
      complete sequence (ACCESSION AC005164)

<400> SEQUENCE: 63
caaagctact tccacagcct cc                                              22
```

<210> SEQ ID NO 64
<211> LENGTH: 21
<212> TYPE: DNA
<213> ORGANISM: Artificial Sequence
<220> FEATURE:
<223> OTHER INFORMATION: synthesize oligonucleotide by referring to Homo
      sapiens PAC clone RP5-1142J19 from 7q35-q36,
      complete sequence (ACCESSION AC004975)

<400> SEQUENCE: 64
gcaggcacca agaactacag c                                              21

<210> SEQ ID NO 65
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens PAC clone RP5-1142J19 from 7q35-q36,
      complete sequence (ACCESSION AC004975)

<400> SEQUENCE: 65
gcctaaggtc acgttgtccc                                                20

<210> SEQ ID NO 66
<211> LENGTH: 21
<212> TYPE: DNA
<213> ORGANISM: Artificial Sequence
<220> FEATURE:
<223> OTHER INFORMATION: synthesize oligonucleotide by referring to Homo
      sapiens PAC clone RP5-1142J19 from 7q35-q36,
      complete sequence (ACCESSION AC004975)

<400> SEQUENCE: 66
gcaggcacca agaactaccg c                                              21

<210> SEQ ID NO 67
<211> LENGTH: 21
<212> TYPE: DNA
<213> ORGANISM: Artificial Sequence
<220> FEATURE:
<223> OTHER INFORMATION: synthesize oligonucleotide by referring to Homo
      sapiens PAC clone RP5-1142J19 from 7q35-q36,
      complete sequence (ACCESSION AC004975)

<400> SEQUENCE: 67
gcaggcacca agaactacgg c                                              21

<210> SEQ ID NO 68
<211> LENGTH: 21
<212> TYPE: DNA
<213> ORGANISM: Artificial Sequence
<220> FEATURE:
<223> OTHER INFORMATION: synthesize oligonucleotide by referring to Homo
      sapiens PAC clone RP5-1142J19 from 7q35-q36,
      complete sequence (ACCESSION AC004975)

<400> SEQUENCE: 68
gcaggcacca agaactactg c                                              21

<210> SEQ ID NO 69
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens BAC clone CTB-135C18 from 7q11.2-q22,
      complete sequence (ACCESSION AC005164)

```
<400> SEQUENCE: 69
caaagctact ttcacagcat cc                                              22

<210> SEQ ID NO 70
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens BAC clone CTB-135C18 from 7q11.2-q22,
      complete sequence (ACCESSION AC005164)

<400> SEQUENCE: 70
ggcatattca gccaaggatt tc                                              22

<210> SEQ ID NO 71
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens BAC clone CTB-135C18 from 7q11.2-q22,
      complete sequence (ACCESSION AC005164)

<400> SEQUENCE: 71
caaagctact ttcacagcct cc                                              22

<210> SEQ ID NO 72
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens BAC clone CTB-135C18 from 7q11.2-q22,
      complete sequence (ACCESSION AC005164)

<400> SEQUENCE: 72
caaagctact ttcacagcgt cc                                              22

<210> SEQ ID NO 73
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens BAC clone CTB-135C18 from 7q11.2-q22,
      complete sequence (ACCESSION AC005164)

<400> SEQUENCE: 73
caaagctact ttcacagctt cc                                              22

<210> SEQ ID NO 74
<211> LENGTH: 25
<212> TYPE: DNA
<213> ORGANISM: Artificial Sequence
<220> FEATURE:
<223> OTHER INFORMATION: synthesize oligonucleotide by referring to
      Human S100 protein beta-subunit gene, exon 1 (ACCESSION
      M59486 J05600)

<400> SEQUENCE: 74
gactactcta gcgactgtcc atctc                                           25

<210> SEQ ID NO 75
<211> LENGTH: 20
<212> TYPE: DNA
<213> ORGANISM: Artificial Sequence
```

```
<220> FEATURE:
<223> OTHER INFORMATION: synthesize oligonucleotide by referring to
      Human S100 protein beta-subunit gene, exon 1 (ACCESSION
      M59486 J05600)

<400> SEQUENCE: 75
gacagccacc agatccaatc                                                    20

<210> SEQ ID NO 76
<211> LENGTH: 21
<212> TYPE: DNA
<213> ORGANISM: Artificial Sequence
<220> FEATURE:
<223> OTHER INFORMATION: synthesize oligonucleotide by referring to Homo
      sapiens blue cone opsin gene, complete cds
      (ACCESSION L32835)

<400> SEQUENCE: 76
ggcagctttc atgggcactg t                                                  21

<210> SEQ ID NO 77
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens blue cone opsin gene, complete cds
      (ACCESSION L32835)

<400> SEQUENCE: 77
gacagggctg gactgacatt tg                                                 22

<210> SEQ ID NO 78
<211> LENGTH: 21
<212> TYPE: DNA
<213> ORGANISM: Artificial Sequence
<220> FEATURE:
<223> OTHER INFORMATION: synthesize oligonucleotide by referring to Homo
      sapiens beta globin region (HBB alpha) on
      chromosome 11 (ACCESSION NG_000007)

<400> SEQUENCE: 78
ctgctgaaag agatgcggtg g                                                  21

<210> SEQ ID NO 79
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens beta globin region (HBB alpha) on
      chromosome 11 (ACCESSION NG_000007)

<400> SEQUENCE: 79
aggaaaacag cccaagggac ag                                                 22

<210> SEQ ID NO 80
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens BAC clone CTB-135C18 from 7q11.2-q22,
      complete sequence (ACCESSION AC005164)

<400> SEQUENCE: 80
caaagctact ttcacagcct cc                                                 22
```

```
<210> SEQ ID NO 81
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens BAC clone CTB-135C18 from 7q11.2-q22,
      complete sequence (ACCESSION AC005164)

<400> SEQUENCE: 81
caaagctact gtcacagcct cc                                              22

<210> SEQ ID NO 82
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens chromosome 19 clone CTD-2166J9, complete
      sequence (ACCESSION AC010412)

<400> SEQUENCE: 82
caaagcgact gtcagagcct cc                                              22

<210> SEQ ID NO 83
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens chromosome 19 clone CTD-2166J9, complete
      sequence (ACCESSION AC010412)

<400> SEQUENCE: 83
cagagcgact gtcagagcgt cc                                              22

<210> SEQ ID NO 84
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens BAC clone CTB-135C18 from 7q11.2-q22,
      complete sequence (ACCESSION AC005164)

<400> SEQUENCE: 84
ggcatattca gccaaggatt tc                                              22

<210> SEQ ID NO 85
<211> LENGTH: 21
<212> TYPE: DNA
<213> ORGANISM: Artificial Sequence
<220> FEATURE:
<223> OTHER INFORMATION: synthesize oligonucleotide by referring to Homo
      sapiens PAC clone RP5-1142J19 from 7q35-q36,
      complete sequence (ACCESSION AC004975)

<400> SEQUENCE: 85
gcaggcacca agaactactg c                                               21

<210> SEQ ID NO 86
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens PAC clone RP5-1142J19 from 7q35-q36,
      complete sequence (ACCESSION AC004975)
```

<400> SEQUENCE: 86
gcctaaggtc acgttgtccc                                                    20

<210> SEQ ID NO 87
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens BAC clone CTB-135C18 from 7q11.2-q22,
      complete sequence (ACCESSION AC005164)

<400> SEQUENCE: 87
caaagctact ttcacagccg cc                                                 22

<210> SEQ ID NO 88
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens BAC clone CTB-135C18 from 7q11.2-q22,
      complete sequence (ACCESSION AC005164)

<400> SEQUENCE: 88
caaagctact ttcacagcca cc                                                 22

<210> SEQ ID NO 89
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens BAC clone CTB-135C18 from 7q11.2-q22,
      complete sequence (ACCESSION AC005164)

<400> SEQUENCE: 89
caaagctact ttcacagccc cc                                                 22

<210> SEQ ID NO 90
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens BAC clone CTB-135C18 from 7q11.2-q22,
      complete sequence (ACCESSION AC005164)

<400> SEQUENCE: 90
caaagctact ttcacagcct cc                                                 22

<210> SEQ ID NO 91
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens BAC clone CTB-135C18 from 7q11.2-q22,
      complete sequence (ACCESSION AC005164)

<400> SEQUENCE: 91
ggcatattca gccaaggatt tc                                                 22

<210> SEQ ID NO 92
<211> LENGTH: 21
<212> TYPE: DNA

<213> ORGANISM: Artificial Sequence
<220> FEATURE:
<223> OTHER INFORMATION: synthesize oligonucleotide by referring to Homo
      sapiens PAC clone RP5-1142J19 from 7q35-q36,
      complete sequence (ACCESSION AC004975)

<400> SEQUENCE: 92
gcaggcacca agaactacgg c                                              21

<210> SEQ ID NO 93
<211> LENGTH: 21
<212> TYPE: DNA
<213> ORGANISM: Artificial Sequence
<220> FEATURE:
<223> OTHER INFORMATION: synthesize oligonucleotide by referring to Homo
      sapiens PAC clone RP5-1142J19 from 7q35-q36,
      complete sequence (ACCESSION AC004975)

<400> SEQUENCE: 93
gcaggcacca agaactactg c                                              21

<210> SEQ ID NO 94
<211> LENGTH: 21
<212> TYPE: DNA
<213> ORGANISM: Artificial Sequence
<220> FEATURE:
<223> OTHER INFORMATION: synthesize oligonucleotide by referring to Homo
      sapiens PAC clone RP5-1142J19 from 7q35-q36,
      complete sequence (ACCESSION AC004975)

<400> SEQUENCE: 94
gcaggcacca agaactacag c                                              21

<210> SEQ ID NO 95
<211> LENGTH: 21
<212> TYPE: DNA
<213> ORGANISM: Artificial Sequence
<220> FEATURE:
<223> OTHER INFORMATION: synthesize oligonucleotide by referring to Homo
      sapiens PAC clone RP5-1142J19 from 7q35-q36,
      complete sequence (ACCESSION AC004975)

<400> SEQUENCE: 95
gcaggcacca agaactaccg c                                              21

<210> SEQ ID NO 96
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens PAC clone RP5-1142J19 from 7q35-q36,
      complete sequence (ACCESSION AC004975)

<400> SEQUENCE: 96
gcctaaggtc acgttgtccc                                                20

<210> SEQ ID NO 97
<211> LENGTH: 20
<212> TYPE: DNA
<213> ORGANISM: Artificial Sequence
<220> FEATURE:
<223> OTHER INFORMATION: synthesize oligonucleotide by referring to
      Human chromosome 14 DNA sequence BAC C-2240H23 of library
      CalTech-D from chromosome 14 of Homo sapiens (Human), complete
      sequence (ACCESSION AL356017)

<400> SEQUENCE: 97

```
atgaaaagcc ctgctttgca                                              20

<210> SEQ ID NO 98
<211> LENGTH: 20
<212> TYPE: DNA
<213> ORGANISM: Artificial Sequence
<220> FEATURE:
<223> OTHER INFORMATION: synthesize oligonucleotide by referring to
      Human chromosome 14 DNA sequence BAC C-2240H23 of library
      CalTech-D from chromosome 14 of Homo sapiens (Human), complete
      sequence (ACCESSION AL356017)

<400> SEQUENCE: 98
agacttcttc aactcaatgg                                              20

<210> SEQ ID NO 99
<211> LENGTH: 22
<212> TYPE: DNA
<213> ORGANISM: Artificial Sequence
<220> FEATURE:
<223> OTHER INFORMATION: synthesize oligonucleotide by referring to
      Human DNA sequence from clone RP11-760M1 on chromosome 13,
      complete sequence (ACCESSION AL354815)

<400> SEQUENCE: 99
gcatctgggg cctggtattt ag                                           22

<210> SEQ ID NO 100
<211> LENGTH: 25
<212> TYPE: DNA
<213> ORGANISM: Artificial Sequence
<220> FEATURE:
<223> OTHER INFORMATION: synthesize oligonucleotide by referring to
      Human hepatocyte nuclear factor 4-alpha gene, exon 1(ACCESSION
      U72959 U72960)

<400> SEQUENCE: 100
tacaaggcag gcatcatgac tcacg                                        25

<210> SEQ ID NO 101
<211> LENGTH: 21
<212> TYPE: DNA
<213> ORGANISM: Artificial Sequence
<220> FEATURE:
<223> OTHER INFORMATION: synthesize oligonucleotide by referring to
      Human rhodospin gene, complete cds (ACCESSION U49742 K02281)

<400> SEQUENCE: 101
aggagcttag gagggggagg t                                            21

<210> SEQ ID NO 102
<211> LENGTH: 23
<212> TYPE: DNA
<213> ORGANISM: Artificial Sequence
<220> FEATURE:
<223> OTHER INFORMATION: synthesize oligonucleotide by referring to
      Human rhodospin gene, complete cds (ACCESSION U49742 K02281)

<400> SEQUENCE: 102
cattgacagg acaggagaag gga                                          23

<210> SEQ ID NO 103
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens beta globin region (HBB alpha) on
``` chromosome 11 (ACCESSION NG_000007)

<400> SEQUENCE: 103 cttttttgttc ccccagacac tc                                              22

<210> SEQ ID NO 104
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens beta globin region (HBB alpha) on
      chromosome 11 (ACCESSION NG_000007)

<400> SEQUENCE: 104
gcaatggctt aggagttgga ct                                               22

<210> SEQ ID NO 105
<211> LENGTH: 24
<212> TYPE: DNA
<213> ORGANISM: Artificial Sequence
<220> FEATURE:
<223> OTHER INFORMATION: synthesize oligonucleotide by referring to Homo
      sapiens HPFH60R gene for olfactory receptor
      (ACCESSION X81445 X91835)

<400> SEQUENCE: 105
gttaatacct aaggctctac tgca                                             24

<210> SEQ ID NO 106
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens HPFH60R gene for olfactory receptor
      (ACCESSION X81445 X91835)

<400> SEQUENCE: 106
aggcaatggc ggcacccatc                                                  20

<210> SEQ ID NO 107
<211> LENGTH: 24
<212> TYPE: DNA
<213> ORGANISM: Artificial Sequence
<220> FEATURE:
<223> OTHER INFORMATION: synthesize oligonucleotide by referring to
      Human p53 (TP53) gene, complete cds (ACCESSION U94788)

<400> SEQUENCE: 107
gcagagacct gtgggaagcg aaaa                                             24

<210> SEQ ID NO 108
<211> LENGTH: 22
<212> TYPE: DNA
<213> ORGANISM: Artificial Sequence
<220> FEATURE:
<223> OTHER INFORMATION: synthesize oligonucleotide by referring to
      Human p53 (TP53) gene, complete cds (ACCESSION U94788)

<400> SEQUENCE: 108
gagagctgtg gcaagcaggg ga                                               22

<210> SEQ ID NO 109
<211> LENGTH: 20
<212> TYPE: DNA
<213> ORGANISM: Artificial Sequence

```
<220> FEATURE:
<223> OTHER INFORMATION: synthesize oligonucleotide by referring to
      Human p53 (TP53) gene, complete cds (ACCESSION U94788)

<400> SEQUENCE: 109
cccctcctgg cccctgtcat                                                   20

<210> SEQ ID NO 110
<211> LENGTH: 27
<212> TYPE: DNA
<213> ORGANISM: Artificial Sequence
<220> FEATURE:
<223> OTHER INFORMATION: synthesize oligonucleotide by referring to
      Human p53 (TP53) gene, complete cds (ACCESSION U94788)

<400> SEQUENCE: 110
gttagatgac tttgcccaac tgtaggg                                           27

<210> SEQ ID NO 111
<211> LENGTH: 21
<212> TYPE: DNA
<213> ORGANISM: Artificial Sequence
<220> FEATURE:
<223> OTHER INFORMATION: synthesize oligonucleotide by referring to Homo
      sapiens beta globin region (HBB alpha) on
      chromosome 11 (ACCESSION NG_000007)

<400> SEQUENCE: 111
ctgctgaaag agatgcggtg g                                                 21

<210> SEQ ID NO 112
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens beta globin region (HBB alpha) on
      chromosome 11 (ACCESSION NG_000007)

<400> SEQUENCE: 112
aggaaaacag cccaagggac ag                                                22

<210> SEQ ID NO 113
<211> LENGTH: 23
<212> TYPE: DNA
<213> ORGANISM: Artificial Sequence
<220> FEATURE:
<223> OTHER INFORMATION: synthesize oligonucleotide by referring to Homo
      sapiens 16p13.3 sequence section 1 of 8 (ACCESSION
      AE006462 AE005175)

<400> SEQUENCE: 113
cacagatttc caaggatgcg ctg                                               23

<210> SEQ ID NO 114
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens 16p13.3 sequence section 1 of 8 (ACCESSION
      AE006462 AE005175)

<400> SEQUENCE: 114
cgtgctctgt tccagacttg                                                   20

<210> SEQ ID NO 115
```

```
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens SVMT gene for synaptic vesicle monoamine
      transporter, exon 16 and complete cds (ACCESSION
      AB044401)

<400> SEQUENCE: 115
cgtctggcga ttgctccaaa tg                                              22

<210> SEQ ID NO 116
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens SVMT gene for synaptic vesicle monoamine
      transporter, exon 16 and complete cds (ACCESSION
      AB044401)

<400> SEQUENCE: 116
gggcagttgt gatccatgag aa                                              22

<210> SEQ ID NO 117
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens HPFH6OR gene for olfactory receptor
      (ACCESSION X81445 X91835)

<400> SEQUENCE: 117
ggcttgcacc agcttaggaa ag                                              22

<210> SEQ ID NO 118
<211> LENGTH: 25
<212> TYPE: DNA
<213> ORGANISM: Artificial Sequence
<220> FEATURE:
<223> OTHER INFORMATION: synthesize oligonucleotide by referring to Homo
      sapiens HPFH6OR gene for olfactory receptor
      (ACCESSION X81445 X91835)

<400> SEQUENCE: 118
cgttaggcat aatcagtggg atagt                                           25

<210> SEQ ID NO 119
<211> LENGTH: 26
<212> TYPE: DNA
<213> ORGANISM: Artificial Sequence
<220> FEATURE:
<223> OTHER INFORMATION: synthesize oligonucleotide by referring to
      Human p53 (TP53) gene, complete cds (ACCESSION 94788)

<400> SEQUENCE: 119
gcctctgatt cctcactgat tgctct                                          26

<210> SEQ ID NO 120
<211> LENGTH: 23
<212> TYPE: DNA
<213> ORGANISM: Artificial Sequence
<220> FEATURE:
<223> OTHER INFORMATION: synthesize oligonucleotide by referring to
      Human hepatocyte nuclear factor 4-alpha gene, exon 1
      (ACCESSION U72959 U72960)
```

```
<400> SEQUENCE: 120
tgtcaaccac ccttaacccc tcc                                              23

<210> SEQ ID NO 121
<211> LENGTH: 22
<212> TYPE: DNA
<213> ORGANISM: Artificial Sequence
<220> FEATURE:
<223> OTHER INFORMATION: synthesize oligonucleotide by referring to
      Human hepatocyte nuclear factor 4-alpha gene, exon 1
      (ACCESSION U72959 U72960)

<400> SEQUENCE: 121
ttggaggggt gggtgagtca ag                                               22

<210> SEQ ID NO 122
<211> LENGTH: 23
<212> TYPE: DNA
<213> ORGANISM: Artificial Sequence
<220> FEATURE:
<223> OTHER INFORMATION: synthesize oligonucleotide by referring to
      Human hepatocyte nuclear factor 4-alpha gene, exon 1
      (ACCESSION U72959 U72960)

<400> SEQUENCE: 122 ggagggtgg gggttaatgg tta                                               23

<210> SEQ ID NO 123
<211> LENGTH: 20
<212> TYPE: DNA
<213> ORGANISM: Artificial Sequence
<220> FEATURE:
<223> OTHER INFORMATION: synthesize oligonucleotide by referring to Homo
      sapiens diacylglycerol kinase, zeta 104kDa (DGKZ),
      mRNA (ACCESSION NM_003646)

<400> SEQUENCE: 123
ggaacaagac acggctggtt                                                  20

<210> SEQ ID NO 124
<211> LENGTH: 21
<212> TYPE: DNA
<213> ORGANISM: Artificial Sequence
<220> FEATURE:
<223> OTHER INFORMATION: synthesize oligonucleotide by referring to Homo
      sapiens diacylglycerol kinase, zeta 104kDa (DGKZ),
      mRNA (ACCESSION NM_003646)

<400> SEQUENCE: 124
agcaaggcag ggcaggcaag t                                                21

<210> SEQ ID NO 125
<211> LENGTH: 22
<212> TYPE: DNA
<213> ORGANISM: Artificial Sequence
<220> FEATURE:
<223> OTHER INFORMATION: synthesize oligonucleotide by referring to
      Human rhodopsin gene, complete cds (ACCESSION U49742 K02281)

<400> SEQUENCE: 125
cggtcccatt ctcagggaat ct                                               22

<210> SEQ ID NO 126
<211> LENGTH: 22
<212> TYPE: DNA
<213> ORGANISM: Artificial Sequence
<220> FEATURE:
```

<223> OTHER INFORMATION: synthesize oligonucleotide by referring to
      Human rhodopsin gene, complete cds (ACCESSION U49742 K02281)

<400> SEQUENCE: 126
gcccagagga agaagaagga aa                                          22

<210> SEQ ID NO 127
<211> LENGTH: 23
<212> TYPE: DNA
<213> ORGANISM: Artificial Sequence
<220> FEATURE:
<223> OTHER INFORMATION: synthesize oligonucleotide by referring to
      Human DNA for CAAF1 (calcium-binding protein in amniotic
      fluid 1), complete cds (ACCESSION D83657)

<400> SEQUENCE: 127
gcccccaccc aggttggttt cta                                         23

<210> SEQ ID NO 128
<211> LENGTH: 23
<212> TYPE: DNA
<213> ORGANISM: Artificial Sequence
<220> FEATURE:
<223> OTHER INFORMATION: synthesize oligonucleotide by referring to
      Human DNA for CAAF1 (calcium-binding protein in amniotic
      fluid 1), complete cds (ACCESSION D83657)

<400> SEQUENCE: 128
atgccttcat ctggctcagt gaa                                         23

<210> SEQ ID NO 129
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens CYP21 gene, exons 1 through 10; and
      steroid 21-hydroxylase (CYP21) gene, complete cds
      (ACCESSION M12792 M23280)

<400> SEQUENCE: 129
gctcagcatg ctggtggcat aa                                          22

<210> SEQ ID NO 130
<211> LENGTH: 22
<212> TYPE: DNA
<213> ORGANISM: Artificial Sequence
<220> FEATURE:
<223> OTHER INFORMATION: synthesize oligonucleotide by referring to Homo
      sapiens CYP21 gene, exons 1 through 10; and
      steroid 21-hydroxylase (CYP21) gene, complete cds
      (ACCESSION M12792 M23280)

<400> SEQUENCE: 130
cctcatacct tcccccccat tt                                          22

<210> SEQ ID NO 131
<211> LENGTH: 25
<212> TYPE: DNA
<213> ORGANISM: Artificial Sequence
<220> FEATURE:
<223> OTHER INFORMATION: synthesize oligonucleotide by referring to
      Human S100 protein beta-subunit gene, exon 1 (ACCESSION M59486
      J05600)

<400> SEQUENCE: 131
gactactcta gcgactgtcc atctc                                       25

```
<210> SEQ ID NO 132
<211> LENGTH: 20
<212> TYPE: DNA
<213> ORGANISM: Artificial Sequence
<220> FEATURE:
<223> OTHER INFORMATION: synthesize oligonucleotide by referring to
      Human S100 protein beta-subunit gene, exon 1 (ACCESSION M59486
      J05600)

<400> SEQUENCE: 132
gacagccacc agatccaatc                                                  20
```

METHOD OF AMPLIFYING NUCLEIC ACIDS, REAGENT KIT FOR AMPLIFYING NUCLEIC ACIDS, METHOD OF DETECTING SINGLE NUCLEOTIDE POLYMORPHISM, AND REAGENT KIT FOR DETECTING SINGLE NUCLEOTIDE POLYMORPHISM

CROSS-REFERENCE TO RELATED APPLICATIONS

This application is a divisional application of application Ser. No. 11/081,949, filed on Mar. 17, 2005, which is a continuation application based upon and claims the benefit of the prior PCT International Patent Application No. PCT/JP2003/011752, filed on Sep. 12, 2003, the entire contents of which are incorporated herein by reference.

BACKGROUND OF THE INVENTION

1. Field of the Invention

The present invention relates to a method of amplifying nucleic acids by PCR, a reagent kit for amplifying nucleic acids by PCR, a method of detecting single nucleotide polymorphism by PCR and a reagent kit for detecting single nucleotide polymorphism by PCR.

2. Description of Related Art

A method of amplifying nucleic acids by PCR is conventionally known. That is, PCR is a technique to obtain certain DNA by mixing a template DNA, primer DNAs, a DNA polymerase, etc. in a reaction solution, and specifically amplifying a region narrowed by two kinds of the primer DNAs in the template DNA.

As such a method of amplifying nucleic acids, a method using a RecA protein of *E. coli* is known (for example, Patent Document 1).

[Patent Document 1] Japanese Patent No. 3010738 (pages 1 to 4)

However, when PCR is carried out, there may be the cases in which not only a desired nucleic acid (a right specific PCR product), but also byproducts (non-specific PCR products) are amplified. Further, in such cases in the above-mentioned conventional methods, byproducts are amplified in a significant amount even if PCR conditions are changed appropriately.

In light of such circumstances, an object of the present invention is to provide a nucleic acid amplification method for amplifying a desired nucleic acid while suppressing amplification of byproducts in a PCR reaction, a reagent kit for nucleic acid amplification for amplifying the desired nucleic acid while suppressing amplification of the byproducts in the PCR reaction, a method for detecting single nucleotide polymorphism utilizing amplification of the desired nucleic acid while suppressing amplification of the byproducts in the PCR reaction, and a reagent kit for detecting single nucleotide polymorphism by detecting single nucleotide polymorphism utilizing amplification of the desired nucleic acid while suppressing amplification of the byproducts in the PCR reaction.

SUMMARY OF THE INVENTION

Means for solving such problems is a method of amplifying nucleic acids by PCR which is characterized by admixing in a reaction solution, a homologous recombinant protein which contains at least one of a RecA protein derived from *Thermus thermophilus*, and a modified RecA protein obtained by modification of the RecA protein and having a function similar to that of the RecA protein, and carrying out PCR.

According to the present invention, PCR is carried out by mixing the homologous recombinant protein such as RecA protein derived from *Thermus thermophilus* and the like in a reaction solution, to amplify the desired DNA.

By carrying out PCR as such, amplification of byproducts (non-specific PCR product) can be suppressed to low levels without reducing the yield of the desired nucleic acid (the right specific PCR product). In other words, by the presence of the above-mentioned homologous recombinant protein, the primer extension reaction caused by binding of the primer DNAs to a non-specific region of the template DNA is suppressed, and thus it is possible to suppress amplification of non-specific PCR products. More specifically, according to the present invention, it is possible to amplify nucleic acids specifically only if there is a mismatch of 3 bases or less between the primer DNA and the template DNA by changing appropriately PCR conditions. Further, it is possible to amplify nucleic acids specifically only if there is a mismatch of 2 bases or less between the primer DNA and the template DNA by changing appropriately PCR conditions. Still further, it is possible to amplify nucleic acids specifically only if there is a mismatch of 1 base or less between the primer DNA and the template DNA by changing appropriately PCR conditions.

Further, according to the method of amplifying nucleic acids of the present invention, it is possible to amplify nucleic acids in a sufficient amount even if the concentration of the primer DNAs added to the reaction solution is reduced to low levels, and by reducing the concentration of the primer DNAs to low levels, it is possible to specifically amplify the desired nucleic acid only while suppressing amplification of byproducts.

Further, since the specificity is high as described above, it is possible to specifically amplify the desired nucleic acid even when the temperature conditions of the primer extension reaction such as an annealing temperature are changed. That is, in the conventional method of amplifying nucleic acids, when the temperature conditions of the primer extension reaction such as an annealing temperature are set to be low, not only the desired DNA, but also byproducts are amplified in a large amount. However, according to the present invention, it is possible to amplify the desired nucleic acid more specifically.

Further, in the present method of amplifying nucleic acids, it is possible to amplify nucleic acids in a sufficient amount as compared with the conventional method even when the amount of the DNA polymerase to be added is reduced to low levels.

As described above, according to the present invention, it is possible to amplify the desired nucleic acid more specifically.

Herein, the above-mentioned homologous recombinant protein is not limited if it comprises at least one of a RecA protein of *Thermus thermophilus* (it may be referred to as a T.th.RecA protein in the present specification), and a modified RecA protein (a modified T.th.RecA protein) obtained by modification of the RecA protein and having a function similar to that of the RecA protein. The modified T.th.RecA protein includes, for example, a gene product made by inducing site-specific mutation, etc., from a gene encoding T.th.RecA protein and having an amino acid sequence with deletion, substitution or addition of one or more amino acids, and further having a function similar to that of the T.th.RecA protein. In addition, it may be a protein fragment of the T.th.RecA protein which has a function similar to that of the T.th.RecA protein (T.th.RecA fragment) and the like.

The homologous recombinant protein is preferably mixed in the range of 0.1 µg to 100 µg per 1 µg of the primer DNA, and more preferably 1 µg to 10 µg per 1 µg of the primer DNA. If PCR is carried out with the homologous recombinant protein in such a range, the desired nucleic acid can be amplified more efficiently and specifically.

Various reagents used in PCR reaction will be explained below.

The template DNA is not particularly limited. In other words, any template DNA comprising any base sequence may be used, and the chain length is not limited by any upper limit. Accordingly, for example, even a giant DNA having a full length of 3,000 Mbp of the human genome may be used. Needless to say, the origin thereof is not limited. Accordingly, it includes a DNA derived from genomes of a virus, a microorganism, an animal or a plant, or a modified DNA thereof; a plasmid, etc. contained in a microorganism, etc., or a chimera DNA formed by insertion of a heterologous DNA fragment into the plasmid, etc. contained in microorganisms, etc.; or an artificially synthesized oligonucleotide, etc. In addition, the template DNA may be a double-stranded DNA or a single-stranded DNA. Further, a cDNA obtained by the reverse transcription of a RNA may be also used as a template DNA.

The primer DNA is not particularly limited if it is substantially complementary to a significant number of the bases located at both ends of the sequence (the region) to be amplified in the template DNA, and also the origin thereof is not limited. The extent of the substantial complementarity is preferably a mismatch of 3 bases or less, more preferably 2 bases or less, further preferably 1 base or less, and particularly preferably 100% of complementarity for the template DNA. The reason for this is that amplification of the desired nucleic acid becomes difficult with low complementarity of the primer DNA, since, as described above, binding of the primer DNA to the non-specific region of the template DNA to cause the primer extension reaction is suppressed by the presence of the homologous recombinant protein such as a T.th.RecA protein.

Further, the primer DNAs are preferably mixed in the range of 0.01 µM to 10 µM, and particularly preferably 0.1 µM to 1 µM in the final concentration for each of the primer DNAs. If PCR is carried out with the primer DNAs in such a range, the desired nucleic acid can be amplified more efficiently and specifically. Further, by reducing the concentration of the primer DNAs lower than that of the conventional method, it is possible to amplify more specifically the desired nucleic acid only while suppressing amplification of byproducts.

A suitable DNA polymerase is one which is not permanently inactivated by short-time heating at a high temperature at which the DNA chain is denatured in PCR, and has activity at high temperature. The DNA polymerase includes, for example, a DNA polymerase derived from thermophilic bacteria such as *Thermococcus litoralis, Bacillus stearothermophilus, Methanothermus fervidus, Thermus aquaticus, T. flavus, T. lacteus, T. rubens, T. rubber* and *T. thermophilus*, a DNA polymerase derived from thermophilic Archaea such as *Desulfurococcus mobilis, Methanobacterium thermoautotrophilcum, Sulfolobus solfataricus, S. acidocaldarius* and *Thermoplasma acidophilum*, and the like. Among these, a DNA polymerase derived from *Thermus aquaticus* (a Taq DNA polymerase), a DNA polymerase derived from *Thermus thermophilus* (a T.th.DNA polymerase), and a DNA polymerase derived from *Thermococcus litoralis* are preferred in view of easy availability, etc.

In addition, for example, if a Taq DNA polymerase is used, it is preferably mixed in the range of 0.05 unit to 50 units per 100 µl, and more preferably 0.5 unit to 5 units per 100 µl. If PCR is carried out with the DNA polymerase in such a range, the desired nucleic acid can be amplified more efficiently and specifically. Further, even if the amount of the DNA polymerase to be added is reduced to low levels, it is possible to amplify nucleic acids in a sufficient amount as compared with the conventional method.

Further, an antibody which is specific to the above-mentioned DNA polymerase may be mixed in the PCR reaction solution in order to inhibit the activity of the above-mentioned DNA polymerase before amplifying nucleic acids. Such antibody includes a monoclonal antibody, a polyclonal antibody, an antibody produced by a recombination method, an antibody fragment produced by a chemical or recombination method (for example, a Fab fragment) and the like. Among them, it is particularly preferable to use a monoclonal antibody. For example, if a known monoclonal antibody for the Taq DNA polymerase is used, the enzymatic activity of the Taq DNA polymerase at a temperature of about 20° C. to about 40° C. can be inhibited, and also can be inactivated by the high temperature of the thermal PCR cycle.

Further, PCR is generally carried out in the presence of four kinds of dNTPs, i.e., dATP, dCTP, dGTP and dTTP.

In addition, PCR is generally carried out in a reaction solution containing a suitable buffer to amplify nucleic acids efficiently. The buffer solution can be suitably varied to obtain optimal reaction conditions according to the homologous recombinant protein, the DNA polymerase, etc. used in the PCR reaction. For example, potassium chloride or magnesium chloride can be added to a TRIS buffer solution of which pH is suitably adjusted.

Further, 5% to 10% of DMSO and 1% to 2% of betaine may be added to the PCR reaction solution, which has effects of minimizing the problem that amplification of desired product becomes poor due to a secondary structure of the template DNA. The RecA protein derived from *E. coli* and the like has no resistance to the denaturing agents while the RecA protein derived from *Thermus thermophilus* has resistance to the denaturing agents and thus can be used in the present invention.

Further, an antibody for the homologous recombinant protein such as the RecA protein derived from *Thermus thermophilus* may be added to the PCR reaction solution.

Another means for solving such problems is a method of amplifying nucleic acids by PCR, wherein the method is characterized by admixing in a reaction solution, a homologous recombinant protein which contains at least one of a RecA protein which causes primer extension reaction only for the primer DNA having a mismatch of 3 bases or less with the template DNA, and a modified RecA protein obtained by modification of the RecA protein and having a function similar to that of the RecA protein, and carrying out PCR.

According to the present invention, PCR is carried out by mixing the homologous recombinant protein such as RecA protein and the like which causes primer extension reaction only for the primer DNA having a mismatch of 3 bases or less with the template DNA, in a reaction solution to amplify the desired DNA.

By carrying out PCR as such, amplification of byproducts can be suppressed to low levels without decreasing the yield of the desired nucleic acid. In other words, by the presence of the homologous recombinant protein, the primer extension reaction caused by binding of the primer DNAs to a non-specific region of the template DNA is suppressed, and thus it is possible to suppress amplification of non-specific PCR products.

Further, according to this method of amplifying nucleic acids, it is possible to amplify nucleic acids in a sufficient amount even if the concentration of the primer DNAs added to the reaction solution is reduced to low levels, and by reducing the concentration of the primer DNAs to low levels, it is possible to specifically amplify the desired nucleic acid only while suppressing amplification of byproducts.

Further, since the specificity is high as described above, it is possible to specifically amplify the desired nucleic acid even when the temperature conditions of the primer extension reaction such as an annealing temperature are changed. That is, in the conventional method of amplifying nucleic acids, when the temperature conditions of the primer extension reaction such as the annealing temperature are set to be low, not only the desired nucleic acid, but also byproducts are amplified in a large amount. However, according to the present invention, it is possible to amplify the desired nucleic acid more specifically.

Further, in the above-described method of amplifying nucleic acids, it is possible to amplify nucleic acids in a sufficient amount as compared with the conventional method even if the amount of the DNA polymerase added to the reaction solution is suppressed to low levels.

As described above, in the method of amplifying nucleic acids according to the present invention, it is possible to amplify the desired nucleic acid more specifically.

Further, the method of amplifying nucleic acids according to any of those described above is preferably provided as a method of amplifying nucleic acids, characterized by adding ATP-γS to a reaction solution and carrying out PCR.

According to the present invention, the above-described homologous recombinant protein is mixed with a reaction solution, further ATP-γS is added and PCR is carried out.

By carrying out PCR as such, it is possible to amplify the desired nucleic acid more specifically. In addition, similarly to the addition of ATP-γS, addition of ATP is also assumed to increase the specificity of PCR. However, ATP is decomposed to ADP by the homologous recombinant protein, and ADP inhibits the homologous recombinant protein from binding to the primer DNAs and the like. Therefore, it is difficult to improve specificity of PCR by addition of ATP. Accordingly, as in the present invention, ATP-γS which is not decomposed to ADP, is preferably added to the reaction solution.

In addition, in preparing the PCR reaction solution, ATP-γS is preferably added before the addition of dNTP to the reaction solution to which T.th.RecA protein is already added. The reason for this is considered to be that if dNTP is added in advance, dNTP binds to T.th.RecA protein, and the ATP-γS added thereafter is difficult to bind to T.th.RecA protein.

Herein, the concentration of ATP-γS may be varied suitably depending on the purpose, but is usually 0.01 mM to 10 mM, and preferably 0.1 mM to 1 mM.

Further, the method of amplifying nucleic acids according to any of those described above is preferably provided as a method of amplifying nucleic acids, characterized by a template DNA having a region of an inhibitory or suppressive secondary structure.

According to the present invention, the template DNA has a region of an inhibitory or suppressive secondary structure. That is, the template DNA has a region of a secondary structure which inhibits or suppresses nucleic acid amplification when usual PCR is carried out. Accordingly, in the conventional PCR, it was difficult to amplify the desired nucleic acid which has such a region efficiently and specifically.

In contrast, in the present invention, it is possible to amplify the desired nucleic acid efficiently and specifically even when the template DNA has the region of the inhibitory or suppressive secondary structure since PCR is carried out by mixing the above-described homologous recombinant protein. The reason for this is considered to be that by binding of the homologous recombinant protein to the template DNA, the inhibitory or suppressive secondary structure is released.

Further, the method of amplifying nucleic acids according to any of those described above is preferably provided as a method of amplifying nucleic acids, characterized by adding KCl to the reaction solution and carrying out PCR.

According to the present invention, KCl is added to the reaction solution and PCR is carried out. By carrying out PCR as such, it is possible to amplify the desired nucleic acid more specifically.

Herein, the concentration of KCl may be varied suitably depending on the purpose, but is usually 1 mM to 1,000 mM, and preferably 10 mM to 100 mM.

Further, the method of amplifying nucleic acids according to any of those described above is preferably provided as a method of amplifying nucleic acids, characterized by adding $Mg^{2+}$ to the reaction solution and carrying out PCR.

According to the present invention, $Mg^{2+}$ is added to the reaction solution and PCR is carried out. By carrying out PCR as such, it is possible to amplify the desired nucleic acid more specifically. The reason for this is considered to be that by the addition of $Mg^{2+}$, affinity of the above-mentioned homologous recombinant protein for DNA is improved.

Herein, the concentration of $Mg^{2+}$ may be varied suitably depending on the purpose, but is usually 0.1 mM to 100 mM, and preferably 3 mM to 10 mM.

Further, the method of amplifying nucleic acids according to any of those described above is preferably provided as a method of amplifying nucleic acids, characterized by adding a plurality of sets of primer DNAs to the reaction solution and carrying out PCR.

According to the present invention, PCR is carried out in the reaction solution to which the plurality of sets of primer DNAs are added.

In the conventional methods of amplifying nucleic acids, it was difficult to add a plurality of sets of primer DNAs since it was difficult to amplify the desired nucleic acid unless the concentration of the primer DNAs was high to some degree.

In contrast, in the present invention, it is possible to specifically amplify the desired nucleic acid only while suppressing amplification of byproducts even if the DNA concentration of each primer DNA is reduced to low levels, by the addition of the above-described homologous recombinant protein. Accordingly, a plurality of sets of primer DNAs can be mixed, and further, even if PCR is carried out as such, it is possible to specifically amplify the desired nucleic acid only corresponding to each of the primer sets while suppressing amplification of byproducts.

Still another means for solving such problems is a reagent kit for amplifying nucleic acids by PCR, wherein the kit is characterized by comprising a DNA polymerase, four kinds of dNTPs, a buffer solution, and a homologous recombinant protein which comprises at least one of a RecA protein derived from *Thermus thermophilus* and a modified RecA protein obtained by modification of the RecA protein and having a function similar to that of the RecA protein.

The reagent kit for amplifying nucleic acids of the present invention comprises a DNA polymerase, four kinds of dNTPs, a buffer solution, and a homologous recombinant protein such as T.th.RecA protein and the like.

PCR can be easily carried out by using such a kit, by preparing a reaction solution to which the DNA polymerase, the four kinds of dNTPs, the buffer solution and the homologous recombinant protein such as T.th.RecA protein and the like are added, and by simply adding further the template DNA and the primer DNA prepared depending on the purpose to the reaction solution. Further, the presence of the homologous recombinant protein suppresses binding of the primer DNA to the non-specific region of the template DNA which causes primer extension reaction, and thus it is possible to suppress amplification of non-specific PCR products. Accordingly, the desired nucleic acid can be amplified more specifically by using the present kit.

In addition, the DNA polymerase, the four kinds of dNTPs, the buffer solution and the homologous recombinant protein such as T.th.RecA protein and the like described in the present invention are similar to those described above.

Herein, the reagent kit for amplifying nucleic acids according to the present invention is not limited if it comprises a DNA polymerase, four kinds of dNTPs, a buffer solution and a homologous recombinant protein such as T.th.RecA protein and the like. Accordingly, such components may be contained in separate vessels, or two or more components of them may be mixed in advance. It is the same for ATP-γS, KCl and $Mg^{2+}$, which will be described below.

Further, the reagent kit for amplifying nucleic acids according to the kit described above is preferably provided as a reagent kit for amplifying nucleic acids, characterized by containing ATP-γS.

If PCR is carried out by using such a kit with further adding ATP-γS, it is possible to amplify the desired nucleic acid more specifically.

Further, the reagent kit for amplifying nucleic acids according to any of those described above is preferably provided as a reagent kit for amplifying nucleic acids, characterized by containing KCl.

If PCR is carried out by using such a kit, it is possible to amplify the desired nucleic acid more specifically.

Further, the reagent kit for amplifying nucleic acids according to any of those described above is preferably provided as a reagent kit for amplifying nucleic acids, characterized by containing $Mg^{2+}$.

If PCR is carried out by using such a kit, it is possible to amplify the desired nucleic acid more specifically.

Still another means for solving such problems is a method of detecting single nucleotide polymorphism, wherein the method is characterized by admixing in a reaction solution, a homologous recombinant protein which comprises at least one of a RecA protein derived from *Thermus thermophilus*, and a modified RecA protein obtained by modification of the RecA protein and having a function similar to that of the RecA protein, and carrying out PCR, by using a primer DNA corresponding to the sequence comprising the base which forms single nucleotide polymorphism in a template DNA, to detect single nucleotide polymorphism by amplifying a desired nucleic acid.

According to the present invention, a primer DNA corresponding to a sequence comprising a base which forms single nucleotide polymorphism in the template DNA is used as one of the primer DNAs. Thus, PCR is carried out with the homologous recombinant protein such as T.th.RecA protein and the like mixed in the reaction solution. By carrying out PCR as such, it is possible to amplify the desired nucleic acid only when the template DNA is completely complementary to the primer DNA corresponding to a sequence comprising a base which forms single nucleotide polymorphism. On the other hand, when the template DNA is not completely complementary to the primer DNA corresponding to the sequence comprising the base which forms single nucleotide polymorphism, i.e., when the base which forms single nucleotide polymorphism is not complementary to the primer DNA, it is possible not to amplify or to inhibit amplification of the desired nucleic acid. Therefore, amplification of the desired nucleic acid by PCR allows detection of single nucleotide polymorphism.

Further, the method of detecting single nucleotide polymorphism according to the method described above is preferably provided as a method of detecting single nucleotide polymorphism, wherein the method is characterized by adding ATP-γS to a reaction solution and carrying out PCR.

According to the present invention, PCR is carried out by mixing the above-described homologous recombinant protein in the reaction solution, and further adding ATP-γS to the reaction solution. By carrying out PCR as such, it is possible to amplify the desired nucleic acid more specifically, allowing the detection of single nucleotide polymorphism more reliably.

Further, the method of detecting single nucleotide polymorphism according to any of those described above is preferably provided as a method of detecting single nucleotide polymorphism, wherein the method is characterized by adding KCl to the reaction solution and carrying out PCR.

By carrying out PCR as such, it is possible to amplify the desired nucleic acid more specifically, allowing the detection of single nucleotide polymorphism more reliably.

Further, the method of detecting single nucleotide polymorphism according to any of those described above is preferably provided as a method of detecting single nucleotide polymorphism, wherein the method is characterized by adding $Mg^{2+}$ to the reaction solution and carrying out PCR.

By carrying out PCR as such, it is possible to amplify the desired nucleic acid more specifically, allowing the detection of single nucleotide polymorphism more reliably.

Still another means for solving such problems is a reagent kit for detecting single nucleotide polymorphism, wherein the kit is characterized by comprising a DNA polymerase, four kinds of dNTPs, a buffer solution, and a homologous recombinant proteins which contains at least one of a RecA protein derived from *Thermus thermophilus* and a modified RecA protein obtained by modification of the RecA protein and having a function similar to that of the RecA protein.

The reagent kit for detecting single nucleotide polymorphism of the present invention comprises a DNA polymerase, four kinds of dNTPs, a buffer solution, and a homologous recombinant protein such as T.th.RecA protein and the like.

PCR can be easily carried out by using such a kit, by preparing a reaction solution, to which the DNA polymerase, the four kinds of dNTPs, the buffer solution and the homologous recombinant protein such as T.th.RecA protein and the like are added to the reaction solution, and by simply adding further the template DNA and the primer DNA prepared depending on the purpose to the reaction solution. By carrying out PCR as such, it is possible to amplify the desired nucleic acid only when the template DNA is completely complementary to the primer DNA corresponding to a sequence comprising a base which forms single nucleotide polymorphism. On the other hand, when the template DNA is not completely complementary to the primer DNA corresponding to the sequence comprising the base which forms single nucleotide polymorphism, i.e., when the base which forms single nucleotide polymorphism is not complementary to the primer DNA, it is possible not to amplify or to inhibit amplification of the desired nucleic acid. Therefore, amplification of the desired nucleic acid by PCR allows the detection of single nucleotide polymorphism.

Accordingly, single nucleotide polymorphism can be easily detected by using the reagent kit for detecting single nucleotide polymorphism of the present invention.

In addition, the DNA polymerase, the four kinds of dNTPs, the buffer solution and the homologous recombinant protein such as T.th.RecA protein and the like described in the present invention are similar to those described above.

Herein, the reagent kit for detecting single nucleotide polymorphism of the present invention is not limited if it comprises a DNA polymerase, four kinds of dNTPs, a buffer solution and a homologous recombinant protein such as T.th.RecA protein and the like. Accordingly, such components may be contained in separate vessels, or two or more components of them may be mixed in advance. It is the same for ATP-γS, KCl and $Mg^{2+}$, which will be described below.

Further, the reagent kit for detecting single nucleotide polymorphism according to the kit described above is preferably provided as a reagent kit for detecting single nucleotide polymorphism, wherein the kit is characterized by comprising ATP-γS.

If PCR is carried out by using such a kit with further adding ATP-γS, it is possible to detect single nucleotide polymorphism more precisely.

Further, the reagent kit for detecting single nucleotide polymorphism according to any of those described above is preferably provided as a reagent kit for detecting single nucleotide polymorphism, wherein the kit is characterized by comprising KCl.

If PCR is carried out by using such a kit, it is possible to detect single nucleotide polymorphism more precisely.

Further, the reagent kit for amplifying nucleic acids according to any of those described above is preferably provided as a reagent kit for amplifying nucleic acids, wherein the kit is characterized by comprising $Mg^{2+}$.

If PCR is carried out by using such a kit, it is possible to detect single nucleotide polymorphism more precisely.

BRIEF DESCRIPTION OF THE DRAWINGS

FIG. 2 is a photograph, instead of a drawing, which shows the results of the electrophoresis for the PCR reaction products with reference to Example 1. (A) is a photograph showing the case where PCR is carried out with the concentration of the primer DNAs of 0.06 µM, and (B) is a photograph showing the case where PCR is carried out with the concentration of the primer DNAs of 0.20 µM.

FIG. 7 is a photograph, instead of a drawing, which shows the results of the electrophoresis for the PCR reaction products with reference to Example 3. (A) is a photograph showing the case where PCR is carried out by changing the concentration of the primer DNAs, and (B) is a photograph showing the case where PCR is carried out by changing the concentration of the primer DNAs by using different primer DNAs.

FIG. 8 is a photograph, instead of a drawing, which shows the results of the electrophoresis for the PCR reaction products with reference to Example 3. (A) is a photograph showing the case where PCR is carried out by changing the concentration of the primer DNAs by using different primer DNAs, and (B) is a photograph showing the case where PCR is carried out by changing the concentration of the primer DNAs by using different primer DNAs.

FIG. 13 is a photograph, instead of a drawing, which shows the results of the electrophoresis for the PCR reaction products with reference to Example 5. (A) is a photograph showing the case where PCR is carried out with an annealing temperature of 60° C., and (B) is a photograph showing the case where PCR is carried out with an annealing temperature of 55° C.

FIG. 14 is a photograph, instead of a drawing, which shows the results of the electrophoresis for the PCR reaction products with reference to Example 5. (A) is a photograph showing the case where PCR is carried out with an annealing temperature of 50° C., and (B) is a photograph showing the case where PCR is carried out with an annealing temperature of 45° C.

FIG. 16 is a photograph, instead of a drawing, which shows the results of the electrophoresis for the PCR reaction products with reference to Example 6. (A) is a photograph showing the case where PCR is carried out using any of Oligonucleotides 37 to 44, and (B) is a photograph showing the case where PCR is carried out using any of Oligonucleotides 54 to 58.

FIG. 17 is a photograph, instead of a drawing, which shows the results of the electrophoresis for the PCR reaction products with reference to Example 7. (A) is a photograph showing the case where the primer DNA is added at the beginning and PCR is carried out, and (B) is a photograph showing the case where the primer DNA is added after 1 cycle and PCR is carried out.

FIG. 18 is a photograph, instead of a drawing, which shows the results of the electrophoresis for the PCR reaction products with reference to Example 7. (A) is a photograph showing the case where the primer DNA is added after 3 cycles and PCR is carried out, and (B) is a photograph showing the case where the primer DNA is added after 6 cycles and PCR is carried out.

FIG. 19 is a photograph, instead of a drawing, which shows the results of the electrophoresis for the PCR reaction products with reference to Example 7. (A) is a photograph showing the case where the primer DNA is added after 10 cycles and PCR is carried out, and (B) is a photograph showing the case where the primer DNA is added after 15 cycles and PCR is carried out.

FIG. 20 is a photograph, instead of a drawing, which shows the results of the electrophoresis for the PCR reaction products with reference to Example 8. (A) is a photograph showing the case where PCR is carried out with an initial temperature of 70° C., and (B) is a photograph showing the case where PCR is carried out with an initial temperature of 80° C.

FIG. 37 is a photograph, instead of a drawing, which shows the results of the electrophoresis for the PCR reaction products with reference to Example 16.

FIG. 47 is a photograph, instead of a drawing, which shows the results of the electrophoresis for the PCR reaction products with reference to Example 19.

DETAILED DESCRIPTION OF THE PREFERRED EMBODIMENTS

Examples of the present invention will be further illustrated below in reference to Drawings.

Example 1

Figure 1:
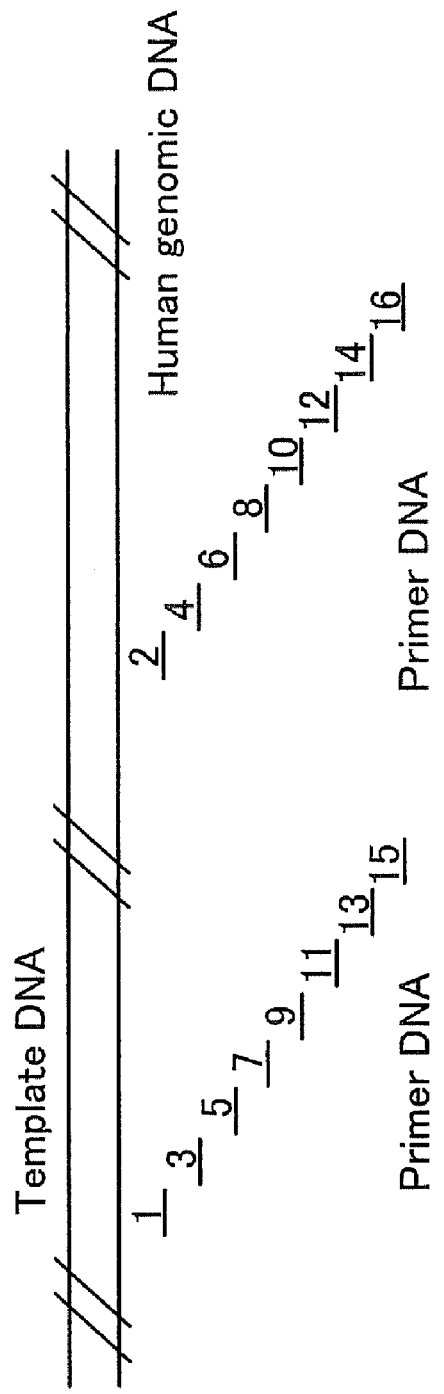
FIG. 1 is an illustrative view showing the relation between a template DNA and a primer DNA with reference to Example 1.

A human genome DNA (Promega) was prepared as a template DNA as shown in FIG. 1. Further, 16 kinds of oligonucleotides (Oligonucleotides 1 to 16) were prepared as the primer DNAs. Each primer DNA was designed with reference to *Homo sapiens* PAC clone from RP5-852P6 from 7p11.2-p21, complete sequence (Genbank accession no.; AC006454). The Genbank accession no.; number refers to an access number of Gene Bank (the same in the following). Since each primer DNA has possibility of any primer design, each of the positions was shifted to design the primer DNA. Each primer DNA consists of a 20 mer base sequence which is 100% complementary to the template DNA. Each primer DNA may be synthesized by a known method on the basis of the base sequence of the template DNA.

```
Oligonucleotide 1:
5'-ggtgcactcc atcatgctta-3'      (SEQ ID NO: 1)

Oligonucleotide 2:
5'-catcagt cagaggggct cac-3'     (SEQ ID NO: 2)

Oligonucleotide 3:
5'-cccacatccc tggcaggaat-3'      (SEQ ID NO: 3)
```

-continued

```
Oligonucleotide 4:
5'-tgcaggt gtgggcctag ctg-3'    (SEQ ID NO: 4)

Oligonucleotide 5:
5'-tgtcctgggc cccagcagga-3'     (SEQ ID NO: 5)

Oligonucleotide 6:
5'-ggggtct tgctgtgggc agg-3'    (SEQ ID NO: 6)

Oligonucleotide 7:
5'-gagatgcccc cccatactgc-3'     (SEQ ID NO: 7)

Oligonucleotide 8:
5'-atctgtc ccctctcctc ctg-3'    (SEQ ID NO: 8)

Oligonucleotide 9:
5'-aggtgtgcag agtgcaaagc-3'     (SEQ ID NO: 9)

Oligonucleotide 10:
5'-gcttcaa ggcagaggcc agg-3'    (SEQ ID NO: 10)

Oligonucleotide 11:
5'-tccaggtggc ccccaagcag-3'     (SEQ ID NO: 11)

Oligonucleotide 12:
5'-atctctc ttgccttggg gtg-3'    (SEQ ID NO: 12)

Oligonucleotide 13:
5'-gtgtgctggg aggaggggcc-3'     (SEQ ID NO: 13)

Oligonucleotide 14:
5'-gtcacta aacaggggct caa-3'    (SEQ ID NO: 14)

Oligonucleotide 15:
5'-cgtgtgggag gagcaggcag-3'     (SEQ ID NO: 15)

Oligonucleotide 16:
5'-gccagaa tgttcccctg gag-3'    (SEQ ID NO: 16)
```

In addition, a RecA protein of *Thermus thermophilus* was prepared as a homologous recombinant protein, and a DNA polymerase derived from *Thermus aquaticus* (TaKaRa Taq; Takara Bio, Inc.) was prepared as the DNA polymerase. In addition, four kinds of dNTPs, i.e., dATP, dCTP, dGTP and dTTP were prepared, and a buffer solution was prepared by adding potassium chloride and magnesium chloride as buffer to a pH-adjusted Tris buffer solution.

Here, it is convenient to have a DNA polymerase, four kinds of dNTPs, a buffer solution and a homologous recombinant protein such as T.th.RecA protein and the like prepared in advance as a reagent kit for amplifying nucleic acids. PCR can be easily carried out by using such a kit, by preparing a reaction solution to which the DNA polymerase, the four kinds of dNTPs, the buffer solution and the homologous recombinant protein such as T.th.RecA protein and the like are added, and by simply adding further the template DNA and the primer DNA prepared depending on the purpose to the reaction solution.

Then, nucleic acids were amplified by the PCR reaction. Specifically, 0.06 µM each (the final concentration) of two kinds of the oligonucleotides, 40 ng of the human genome DNA, 1.0 unit of Taq polymerase, 0.2 mM of the dNTP mixture solution and 1.2 µg of the T.th.RecA protein were mixed with 10 mM Tris-HCl Buffer (pH 8.3), 50 mM KCl and 1.5 mM $MgCl_2$ in 10 µl of a PCR reaction solution. Then, PCR was carried out with 1 cycle (at 70° C. for 10 minutes and at 94° C. for 1 minute), 30 cycles (at 94° C. for 30 seconds, at 60° C. for 30 seconds, and at 68° C. for 1 minute) and 1 cycle (at 68° C. for 7 minutes and at 4° C. for 1 minute).

Then, the reaction solution was subjected to electrophoresis with a 1% agarose gel, the agarose gel was soaked in an ethidium bromide solution to stain the DNA in the gel, and then the stained DNA was recorded by photography. The results are shown in FIG. 2.

Lane 1 shows the results when Oligonucleotide 1 and Oligonucleotide 2 were added as the primer DNAs.

Lane 2 shows the results when Oligonucleotide 3 and Oligonucleotide 4 were added as the primer DNAs.

Lane 3 shows the results when Oligonucleotide 5 and Oligonucleotide 6 were added as the primer DNAs.

Lane 4 shows the results when Oligonucleotide 7 and Oligonucleotide 8 were added as the primer DNAs.

Lane 5 shows the results when Oligonucleotide 9 and Oligonucleotide 10 were added as the primer DNAs.

Lane 6 shows the results when Oligonucleotide 11 and Oligonucleotide 12 were added as the primer DNAs.

Lane 7 shows the results when Oligonucleotide 13 and Oligonucleotide 14 were added as the primer DNAs.

Lane 8 shows the results when Oligonucleotide 15 and Oligonucleotide 16 were added as the primer DNAs.

Lane 9 shows the results when PCR was carried out in the same manner as in Lane 1 without adding the T.th.RecA protein.

Lane 10 shows the results when PCR was carried out in the same manner as in Lane 2 without adding the T.th.RecA protein.

Lane 11 shows the results when PCR was carried out in the same manner as in Lane 3 without adding the T.th.RecA protein.

Lane 12 shows the results when PCR was carried out in the same manner as in Lane 4 without adding the T.th.RecA protein.

Lane 13 shows the results when PCR was carried out in the same manner as in Lane 5 without adding the T.th.RecA protein.

Lane 14 shows the results when PCR was carried out in the same manner as in Lane 6 without adding the T.th.RecA protein.

Lane 15 shows the results when PCR was carried out in the same manner as in Lane 7 without adding the T.th.RecA protein.

Lane 16 shows the results when PCR was carried out in the same manner as in Lane 8 without adding the T.th.RecA protein.

Lane 17 shows the results when PCR was carried out in the same manner as in Lane 1 by increasing the concentration of each of the primer DNAs to 0.20 µM, respectively (the final concentration).

Lane 18 shows the results when PCR was carried out in the same manner as in Lane 2 by increasing the concentration of each of the primer DNAs to 0.20 µM, respectively (the final concentration).

Lane 19 shows the results when PCR was carried out in the same manner as in Lane 3 by increasing the concentration of each of the primer DNAs to 0.20 µM, respectively (the final concentration).

Lane 20 shows the results when PCR was carried out in the same manner as in Lane 4 by increasing the concentration of each of the primer DNAs to 0.20 µM, respectively (the final concentration).

Lane 21 shows the results when PCR was carried out in the same manner as in Lane 5 by increasing the concentration of each of the primer DNAs to 0.20 µM, respectively (the final concentration).

Lane 22 shows the results when PCR was carried out in the same manner as in Lane 6 by increasing the concentration of each of the primer DNAs to 0.20 µM, respectively (the final concentration).

Lane 23 shows the results when PCR was carried out in the same manner as in Lane 7 by increasing the concentration of each of the primer DNAs to 0.20 µM, respectively (the final concentration).

Lane 24 shows the results when PCR was carried out in the same manner as in Lane 8 by increasing the concentration of each of the primer DNAs to 0.20 µM, respectively (the final concentration).

Lane 25 shows the results when PCR was carried out in the same manner as in Lane 9 by increasing the concentration of each of the primer DNAs to 0.20 µM, respectively (the final concentration).

Lane 26 shows the results when PCR was carried out in the same manner as in Lane 10 by increasing the concentration of each of the primer DNAs to 0.20 µM, respectively (the final concentration).

Lane 27 shows the results when PCR was carried out in the same manner as in Lane 11 by increasing the concentration of each of the primer DNAs to 0.20 µM, respectively (the final concentration).

Lane 28 shows the results when PCR was carried out in the same manner as in Lane 12 by increasing the concentration of each of the primer DNAs to 0.20 µM, respectively (the final concentration).

Lane 29 shows the results when PCR was carried out in the same manner as in Lane 13 by increasing the concentration of each of the primer DNAs to 0.20 µM, respectively (the final concentration).

Lane 30 shows the results when PCR was carried out in the same manner as in Lane 14 by increasing the concentration of each of the primer DNAs to 0.20 µM, respectively (the final concentration).

Lane 31 shows the results when PCR was carried out in the same manner as in Lane 15 by increasing the concentration of each of the primer DNAs to 0.20 µM, respectively (the final concentration).

Lane 32 shows the results when PCR was carried out in the same manner as in Lane 16 by increasing the concentration of each of the primer DNAs to 0.20 µM, respectively (the final concentration).

As clearly shown in the results of FIG. 2(A), in Lanes 1 to 8 in which PCR was carried out with the addition of T.th.RecA protein, amplification of the desired nucleic acid (the right specific PCR product) was detected whereas byproducts (non-specific PCR products) were scarcely detected.

In contrast, in Lanes 9 to 16 in which PCR was carried out without adding the T.th.RecA protein, not only the desired nucleic acid but also byproducts were detected in a large amount. In addition, there were a few cases in which nucleic acid amplification was scarcely detected (Lanes 15, 16, etc.). The reason for this is considered to be that the region which has to be amplified in the template DNA has an inhibitory or suppressive secondary structure.

Also, as clearly shown in the results of FIG. 2(B), in Lanes 17 to 24 in which PCR was carried out with the addition of T.th.RecA protein and increasing the concentrations of the primer DNAs, amplification of the desired DNA was detected. However, as compared with the results of Lanes 1 to 8, there were many lanes in which byproducts were also slightly detected.

On other hand, in Lanes 25 to 32 in which PCR was carried out by increasing the concentrations of the primer DNAs but without adding the T.th.RecA protein, byproducts were detected in an amount larger than with the results of the corresponding Lanes 9 to 16.

From these facts, if the T.th.RecA protein is added and PCR is carried out, amplification of byproducts can be suppressed to low levels without decreasing the yield of the desired nucleic acid. In other words, by the presence of the T.th.RecA protein, the primer extension reaction caused by binding of the primer DNAs to a non-specific region of the template DNA is suppressed, and thus it is possible to suppress amplification of non-specific PCR products.

Further, if PCR is carried out with the addition of T.th.RecA protein, it is possible to amplify the desired nucleic acid efficiently and specifically even when the template DNA has the region of the inhibitory or suppressive secondary structure. The reason for this is considered to be that the inhibitory or suppressive secondary structure is released as the homologous recombinant protein binds to the template DNA.

Further, it is possible to amplify nucleic acids in a sufficient amount even when the concentration of the primer DNAs added to the reaction solution is reduced to low levels (0.06 µM), and by reducing the concentration of the primer DNAs to low levels, it is possible to specifically amplify the desired nucleic acid only while suppressing amplification of byproducts.

Example 2

Next, Example 2 will be explained. Explanation of the parts which are similar to those of the Example 1 will be omitted or simplified.

Figure 3:
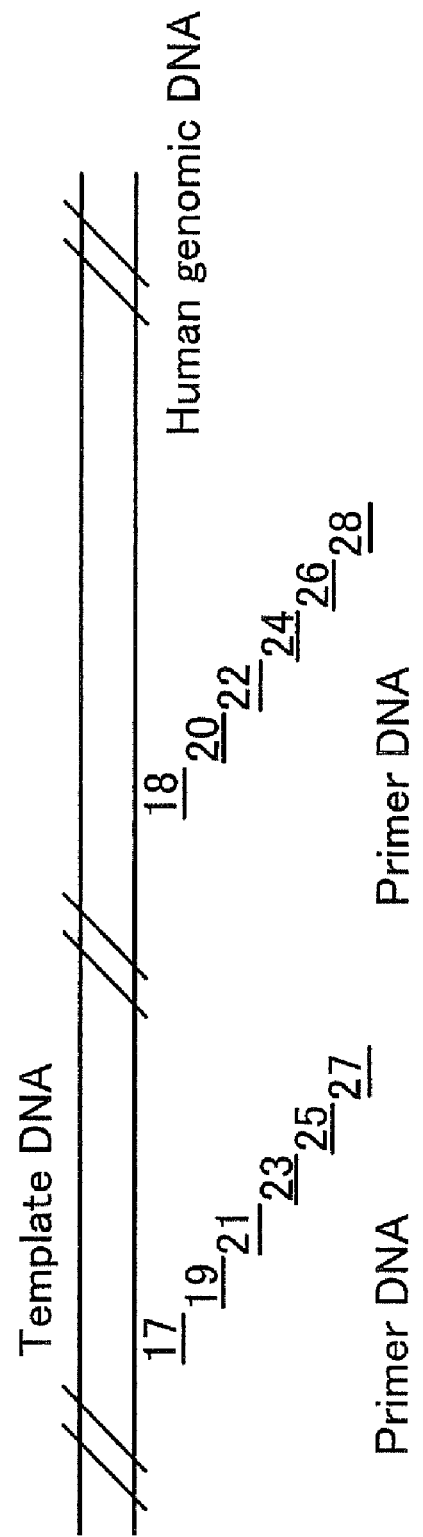
FIG. 3 is an illustrative view showing the relation between a template DNA and a primer DNA with reference to Example 2.

In this Example, as shown in FIG. 3, a human genome DNA was prepared as a template DNA, and 12 kinds of oligonucleotides (Oligonucleotides 17 to 28) were prepared as the primer DNAs. Each primer DNA was designed with reference to Homo sapiens BAC clone from RP11-16P10 from 7, complete sequence (Genbank accession no.; AC093734, AC011786). Since each primer DNA has possibility of any primer design, each position was shifted to design the primer DNA. Each primer DNA consists of a 20 mer base sequence which is 100% complementary to the template DNA.

```
Oligonucleotide 17:
5'-cgggtgc acacaaaggc tgg-3'        (SEQ ID NO: 17)

Oligonucleotide 18:
5'-tctctggcca ggtgcctggc-3'         (SEQ ID NO: 18)

Oligonucleotide 19:
5'-cgccccg acaaccctga ccc-3'        (SEQ ID NO: 19)

Oligonucleotide 20:
5'-cttgggaaga tcctgagact-3'         (SEQ ID NO: 20)

Oligonucleotide 21:
5'-tcggtaa acgctggctc ccg-3'        (SEQ ID NO: 21)

Oligonucleotide 22:
5'-caaaacgccc cccaccgccc-3'         (SEQ ID NO: 22)

Oligonucleotide 23:
5'-ggtttac cagcacctgg gga-3'        (SEQ ID NO: 23)

Oligonucleotide 24:
5'-cccatcgtgg tctaggggat-3'         (SEQ ID NO: 24)

Oligonucleotide 25:
5'-gaagtgg cccggaagac ggt-3'        (SEQ ID NO: 25)

Oligonucleotide 26:
5'-gcagcgccct tcccacccct-3'         (SEQ ID NO: 26)
```

-continued

```
Oligonucleotide 27:
5'-gcacacg ccttgtagac agc-3'      (SEQ ID NO: 27)

Oligonucleotide 28:
5'-ctgattctcc agggtgggct-3'       (SEQ ID NO: 28)
```

Then, PCR was carried out under the same conditions as those of Lane 1, etc. of the above-mentioned Example 1. Subsequently, the reaction solution was subjected to electrophoresis with a 1% agarose gel, and the results were recorded by photography and shown in FIG. 4, in the same manner as in the above-mentioned Example 1.

Lane 1 shows the results when Oligonucleotide 17 and Oligonucleotide 18 were added as the primer DNAs.

Lane 2 shows the results when Oligonucleotide 19 and Oligonucleotide 20 were added as the primer DNAs.

Lane 3 shows the results when Oligonucleotide 21 and Oligonucleotide 22 were added as the primer DNAs.

Lane 4 shows the results when Oligonucleotide 23 and Oligonucleotide 24 are added as the primer DNA.

Lane 5 shows the results when Oligonucleotide 25 and Oligonucleotide 26 were added as the primer DNAs.

Lane 6 shows the results when Oligonucleotide 27 and Oligonucleotide 28 are added as the primer DNA.

Lane 7 shows the results when PCR was carried out in the same manner as in Lane 1 without adding the T.th.RecA protein.

Lane 8 shows the results when PCR was carried out in the same manner as in Lane 2 without adding the T.th.RecA protein.

Lane 9 shows the results when PCR was carried out in the same manner as in Lane 3 without adding the T.th.RecA protein.

Lane 10 shows the results when PCR was carried out in the same manner as in Lane 4 without adding the T.th.RecA protein.

Lane 11 shows the results when PCR was carried out in the same manner as in Lane 5 without adding the T.th.RecA protein.

Lane 12 shows the results when PCR was carried out in the same manner as in Lane 6 without adding the T.th.RecA protein.

Figure 4:
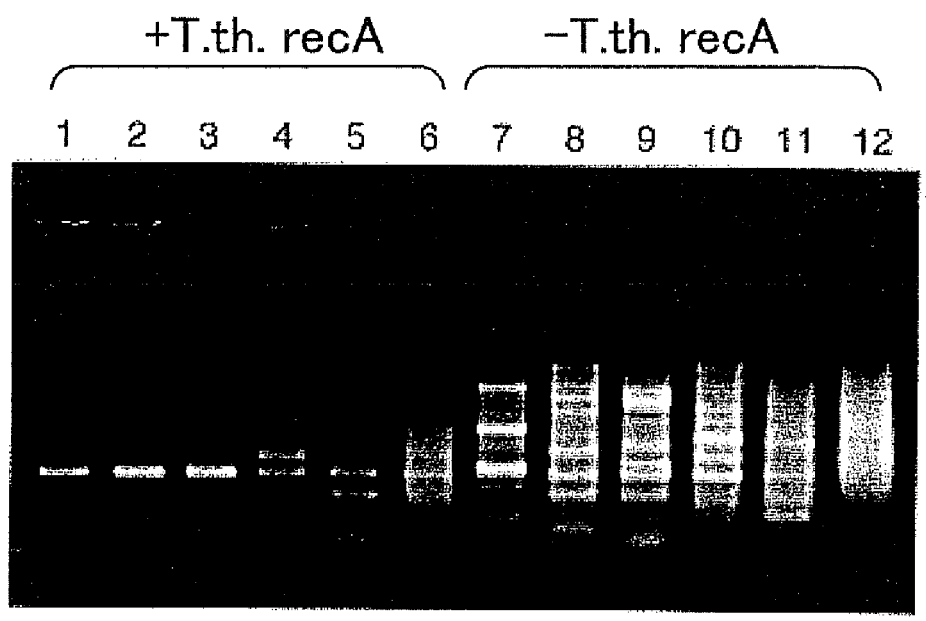
FIG. 4 is a photograph, instead of a drawing, which shows the results of the electrophoresis for the PCR reaction products with reference to Example 2.

As clearly shown in the results of FIG. 4, in Lanes 1 to 6 in which PCR was carried out with the addition of T.th.RecA protein, amplification of the desired nucleic acid (the right specific PCR product) was detected while byproducts (non-specific PCR products) were scarcely detected in many of these lanes. Further, even in the lanes where byproducts were detected, production of the byproducts were largely suppressed, as compared with the lanes in which PCR was carried out without adding the T.th.RecA protein.

In contrast, in Lanes 7 to 12 in which PCR was carried out without adding the T.th.RecA protein, not only the desired nucleic acid but also byproducts were detected in a large amount.

From these results, if PCR is carried out with the addition of T.th.RecA protein, amplification of byproducts can be suppressed to low levels without decreasing the yield of the desired nucleic acid. In other words, by the presence of the T.th.RecA protein, the primer extension reaction caused by binding of the primer DNAs to a non-specific region of the template DNA is suppressed, and thus it is possible to suppress amplification of non-specific PCR products.

Further, it is possible to amplify nucleic acids in a sufficient amount even when the concentration of the primer DNAs added to the reaction solution is reduced to low levels (0.06 μM), and by reducing the concentration of the primer DNAs to low levels, it is possible to specifically amplify the desired nucleic acid only while suppressing amplification of byproducts.

Example 3

Next, Example 3 will be explained. Explanation of the parts which are similar to those of each of the above-mentioned Examples will be omitted or simplified.

Figure 5:
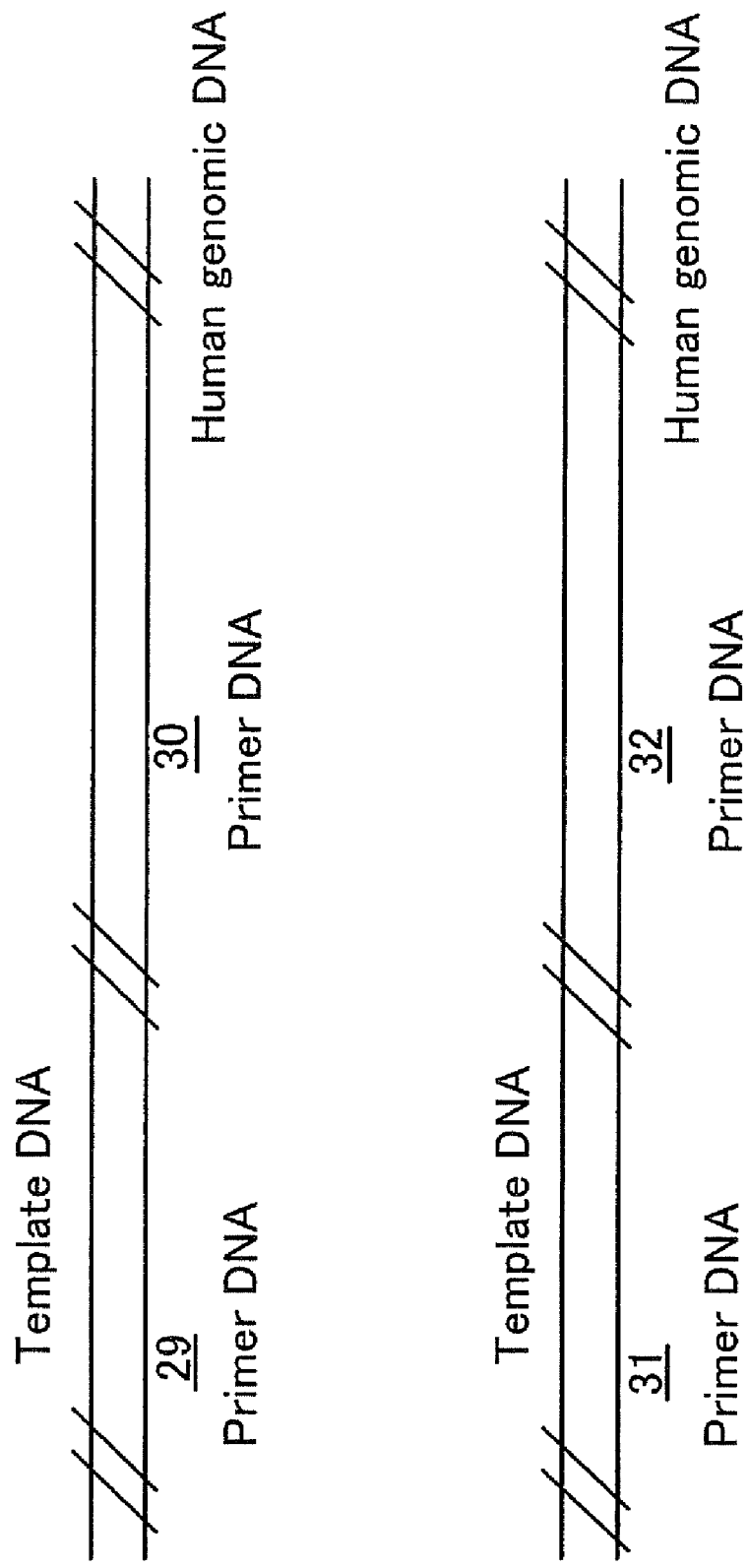
FIG. 5 is an illustrative view showing the relation between a template DNA and a primer DNA with reference to Example 3.
Figure 6:
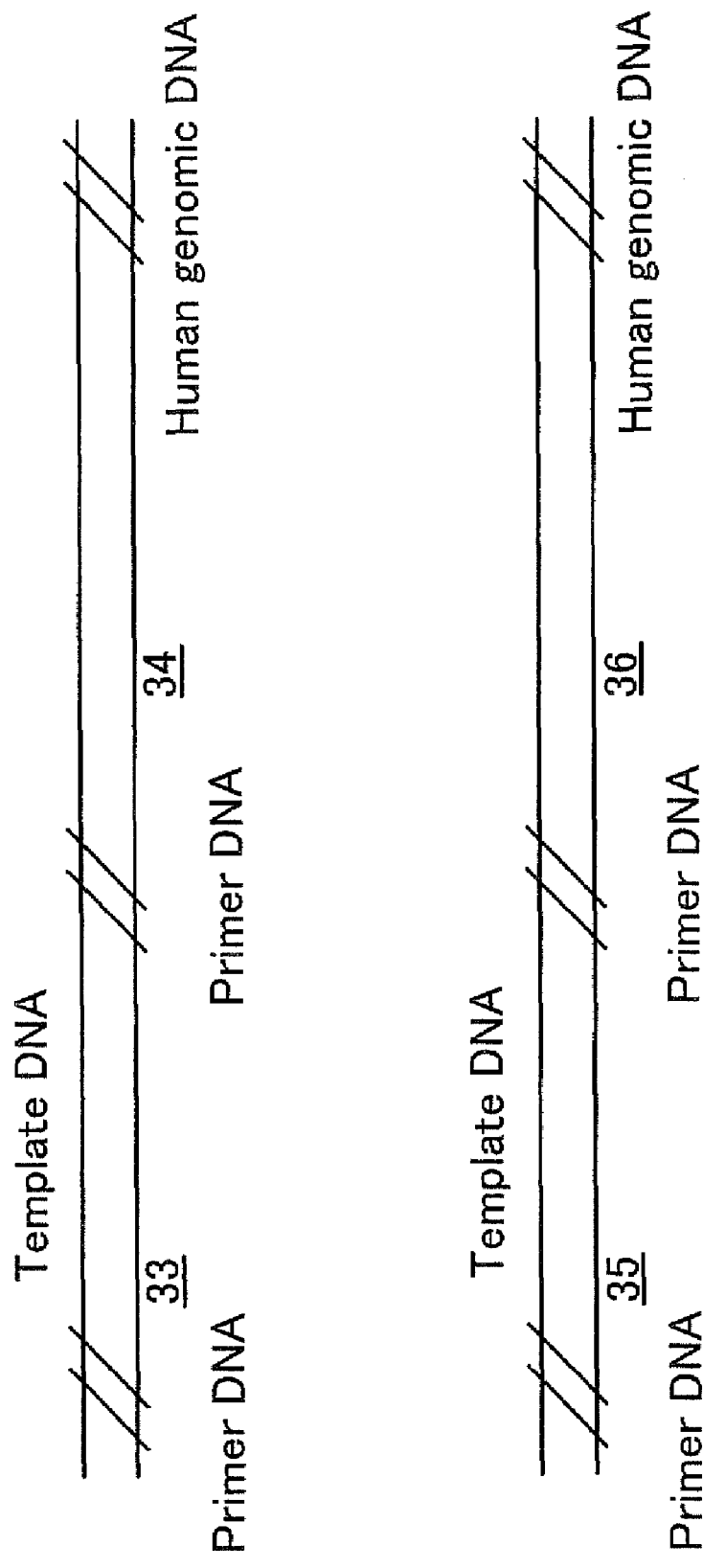
FIG. 6 is an illustrative view showing the relation between the template DNA and the primer DNA with reference to Example 3.

As shown in FIG. 5 and FIG. 6, a human genome DNA was prepared as a template DNA, and 8 kinds of oligonucleotides (Oligonucleotides 29 to 36) were prepared as the primer DNAs. Each primer DNA was designed with reference to the Human DNA sequence from clone RP5-1013A22 on chromosome 20 Contains the HNF4A (hepatic nuclear factor 4, alpha) gene, part of a novel gene encoding a protein similar to cellular retinaldehyde-binding protein, a RPL37A (ribosomal protein L37a) pseudogene, parts of 2 novel genes, ESTs, STSs and GSSs, complete sequence (Genbank accession no.; AL132772). Further, Oligonucleotide 31 and Oligonucleotide 32 were designed with reference to Homo sapiens 3q BAC RP11-529F4 (Roswell Park Cancer Institute Human BAC Library) complete sequence (Genbank accession no.; AC080007). Further, Oligonucleotide 33 and Oligonucleotide 34 were designed with reference to Homo sapiens genomic beta globin region on chromosome 11 (Genbank accession no.; NG000007). Further, Oligonucleotide 35 and Oligonucleotide 36 were designed with reference to Homo sapiens HPFH60R gene for olfactory receptor (Genbank accession no.; X81445, X91835). Each primer DNA consists of a base sequence from a 20 mer to a 25 mer, which is 100% complementary to the template DNA.

```
Oligonucleotide 29:
5'-gcatctgggg cctgggattt ag-3'    (SEQ ID NO: 29)

Oligonucleotide 30:
5'-tacaaggcag gcatcatgac tcacg-3' (SEQ ID NO: 30)

Oligonucleotide 31:
5'-aggagcttag gaggggagg t-3'      (SEQ ID NO: 31)

Oligonucleotide 32:
5'-cattgacagg acaggagaag gga-3'   (SEQ ID NO: 32)

Oligonucleotide 33:
5'-cttttgttc ccccagacac tc-3'     (SEQ ID NO: 33)

Oligonucleotide 34:
5'-gcactggctt aggagttgga ct-3'    (SEQ ID NO: 34)

Oligonucleotide 35:
5'-gttaataccc aaggctctac tgca-3'  (SEQ ID NO: 35)

Oligonucleotide 36:
5'-aggcaatggc ggcacccatc-3'       (SEQ ID NO: 36)
```

Then, a reaction solution was prepared under the same conditions as those of the above-mentioned Example 1 and the like except the concentration of the primer DNAs. Subsequently, PCR was carried out with 1 cycle (at 94° C. for 1 minute), 30 cycles (at 94° C. for 30 seconds, at 60° C. for 30 seconds, and at 68° C. for 1 minute) and 1 cycle (at 68° C. for 7 minutes and at 4° C. for 1 minute). Then, the reaction solution was subjected to electrophoresis with a 1% agarose gel, and the results were recorded by photography and shown in FIG. 7 and FIG. 8, in the same manner as in the above-mentioned Example 1, etc.

Lane 1 shows the results when 0.3 μM (the final concentration) of Oligonucleotide 29 and 0.3 μM (the final concentration) of Oligonucleotide 30 were added as the primer DNAs.

Lane 2 shows the results when PCR was carried out in the same manner as in Lane 1 without adding the T.th.RecA protein.

Lane 3 shows the results when PCR was carried out in the same manner as in Lane 1 by reducing the concentration of each of Oligonucleotide 29 and Oligonucleotide 30 to 0.1 μM (the final concentration), respectively.

Lane 4 shows the results when PCR was carried out in the same manner as in Lane 3 without adding the T.th.RecA protein.

Lane 5 shows the results when PCR was carried out in the same manner as in Lane 1 by reducing the concentration of each of Oligonucleotide 29 and Oligonucleotide 30 to 0.03 μM (the final concentration), respectively.

Lane 6 shows the results when PCR was carried out in the same manner as in Lane 5 without adding the T.th.RecA protein.

Lane 7 shows the results when PCR was carried out in the same manner as in Lane 1 by reducing the concentration of each of Oligonucleotide 29 and Oligonucleotide 30 to 0.01 μM (the final concentration), respectively.

Lane 8 shows the results when PCR was carried out in the same manner as in Lane 7 without adding the T.th.RecA protein.

Lane 9 shows the results when PCR was carried out in the same manner as in Lane 1 by reducing the concentration of each of Oligonucleotide 29 and Oligonucleotide 30 to 0.003 μM (the final concentration), respectively.

Lane 10 shows the results when PCR was carried out in the same manner as in Lane 9 without adding the T.th.RecA protein.

Lane 11 shows the results when 0.3 μM (the final concentration) of Oligonucleotide 31 and 0.3 μM (the final concentration) of Oligonucleotide 32 were added as the primer DNAs.

Lane 12 shows the results when PCR was carried out in the same manner as in Lane 11 without adding the T.th.RecA protein.

Lane 13 shows the results when PCR was carried out in the same manner as in Lane 11 by reducing the concentration of each of Oligonucleotide 31 and Oligonucleotide 32 to 0.1 μM (the final concentration), respectively.

Lane 14 shows the results when PCR was carried out in the same manner as in Lane 13 without adding the T.th.RecA protein.

Lane 15 shows the results when PCR was carried out in the same manner as in Lane 11 by reducing the concentration of each of Oligonucleotide 31 and Oligonucleotide 32 to 0.03 μM (the final concentration), respectively.

Lane 16 shows the results when PCR was carried out in the same manner as in Lane 15 without adding the T.th.RecA protein.

Lane 17 shows the results when PCR was carried out in the same manner as in Lane 11 by reducing the concentration of each of Oligonucleotide 31 and Oligonucleotide 32 to 0.01 μM (the final concentration), respectively.

Lane 18 shows the results when PCR was carried out in the same manner as in Lane 17 without adding the T.th.RecA protein.

Lane 19 shows the results when PCR was carried out in the same manner as in Lane 11 by reducing the concentration of each of Oligonucleotide 31 and Oligonucleotide 32 to 0.003 μM (the final concentration), respectively.

Lane 20 shows the results when PCR was carried out in the same manner as in Lane 19 without adding the T.th.RecA protein.

Lane 21 shows the results when 0.3 μM (the final concentration) of Oligonucleotide 33 and 0.3 μM (the final concentration) of Oligonucleotide 34 were added as the primer DNAs.

Lane 22 shows the results when PCR was carried out in the same manner as in Lane 21 without adding the T.th.RecA protein.

Lane 23 shows the results when PCR was carried out in the same manner as in Lane 21 by reducing the concentration of each of Oligonucleotide 33 and Oligonucleotide 34 to 0.1 μM (the final concentration), respectively.

Lane 24 shows the results when PCR was carried out in the same manner as in Lane 23 without adding the T.th.RecA protein.

Lane 25 shows the results when PCR was carried out in the same manner as in Lane 21 by reducing the concentration of each of Oligonucleotide 33 and Oligonucleotide 34 to 0.03 μM (the final concentration), respectively.

Lane 26 shows the results when PCR was carried out in the same manner as in Lane 25 without adding the T.th.RecA protein.

Lane 27 shows the results when PCR was carried out in the same manner as in Lane 21 by reducing the concentration of each of Oligonucleotide 33 and Oligonucleotide 34 to 0.01 μM (the final concentration), respectively.

Lane 28 shows the results when PCR was carried out in the same manner as in Lane 27 without adding the T.th.RecA protein.

Lane 29 shows the results when PCR was carried out in the same manner as in Lane 21 by reducing the concentration of each of Oligonucleotide 33 and Oligonucleotide 34 to 0.003 μM (the final concentration), respectively.

Lane 30 shows the results when PCR was carried out in the same manner as in Lane 29 without adding the T.th.RecA protein.

Lane 31 shows the results when 0.3 μM (the final concentration) of Oligonucleotide 35 and 0.3 μM (the final concentration) of Oligonucleotide 36 were added as the primer DNAs.

Lane 32 shows the results when PCR was carried out in the same manner as in Lane 31 without adding the T.th.RecA protein.

Lane 33 shows the results when PCR was carried out in the same manner as in Lane 31 by reducing the concentration of each of Oligonucleotide 35 and Oligonucleotide 36 to 0.1 μM (the final concentration), respectively.

Lane 34 shows the results when PCR was carried out in the same manner as in Lane 33 without adding the T.th.RecA protein.

Lane 35 shows the results when PCR was carried out in the same manner as in Lane 31 by reducing the concentration of each of Oligonucleotide 35 and Oligonucleotide 36 to 0.03 μM (the final concentration), respectively.

Lane 36 shows the results when PCR was carried out in the same manner as in Lane 35 without adding the T.th.RecA protein.

Lane 37 shows the results when PCR was carried out in the same manner as in Lane 31 by reducing the concentration of each of Oligonucleotide 35 and Oligonucleotide 36 to 0.01 μM (the final concentration), respectively.

Lane 38 shows the results when PCR was carried out in the same manner as in Lane 37 without adding the T.th.RecA protein.

Lane 39 shows the results when PCR was carried out in the same manner as in Lane 31 by reducing the concentration of each of Oligonucleotide 35 and Oligonucleotide 36 to 0.003 µM (the final concentration), respectively.

Lane 40 shows the results when PCR was carried out in the same manner as in Lane 39 without adding the T.th.RecA protein.

As clearly shown in the results of FIG. 7(A), among Lanes 1, 3, 5, 7 and 9 in which PCR was carried out with the addition of T.th.RecA protein, except in Lane 9, amplification of the desired nucleic acid (the right specific PCR product) was detected whereas byproducts (non-specific PCR products) were scarcely detected. Particularly, as the concentration of the primer DNAs was lower, the production of the byproducts tended to be suppressed. In Lane 9, amplification of DNA was hardly detected, possibly due to the too low concentration of the primer DNAs. Further, if the concentration of the primer DNAs was the same, the amount of amplification of the desired nucleic acid tended to be increased as compared with the cases in which PCR was carried out without adding the T.th.RecA protein.

In contrast, among Lanes 2, 4, 6, 8 and 10 in which PCR was carried out without adding the T.th.RecA protein, except in Lane 10, not only the desired nucleic acid but also byproducts were detected. In Lane 10, amplification of DNA was hardly detected, possibly due to the too low concentration of the primer DNAs.

As clearly shown in the results of FIG. 7(B), among Lanes 11, 13, 15, 17 and 19 in which PCR was carried out with the addition of T.th.RecA protein, except in Lane 19, amplification of the desired nucleic acid was detected whereas byproducts were scarcely detected. Particularly, as the concentration of the primer DNAs was lower, the production of the byproducts tended to be suppressed. In Lane 19, amplification of DNA was hardly detected, possibly due to the too low concentration of the primer DNAs. Further, if the concentration of the primer DNAs was the same, the amount of amplification of the desired nucleic acid tended to be increased as compared with the cases in which PCR was carried out without adding the T.th.RecA protein.

In contrast, among Lanes 12, 14, 16, 18 and 20 in which PCR was carried out without adding the T.th.RecA protein, except in Lane 20, not only the desired nucleic acid but also byproducts were detected. In Lane 20, amplification of DNA was hardly detected, possibly due to the too low concentration of the primer DNAs.

As clearly shown in the results of FIG. 8(A), among Lanes 21, 23, 25, 27 and 29 in which PCR was carried out with the addition of T.th.RecA protein, except in Lane 29, amplification of the desired nucleic acid was detected whereas byproducts were scarcely detected. Particularly, as the concentration of the primer DNAs was lower, the production of the byproducts tended to be suppressed. In Lane 29, amplification of DNA was hardly detected, possibly due to the too low concentration of the primer DNAs. Further, if the concentration of the primer DNAs was the same, the amount of amplification of the desired nucleic acid tended to increase as compared with the cases in which PCR was carried out without adding the T.th.RecA protein.

In contrast, among Lanes 22, 24, 26, 28 and 30 in which PCR was carried out without adding the T.th.RecA protein, in Lanes 22, 24 and 26, not only the desired nucleic acid but also byproducts were detected. In Lanes 28 and 30, amplification of DNA was hardly detected, possibly due to the too low concentration of the primer DNAs.

As clearly shown in the results of FIG. 8(B), among Lanes 31, 33, 35, 37 and 39 in which PCR was carried out with the addition of T.th.RecA protein, except in Lane 39, amplification of the desired nucleic acid was detected whereas byproducts were scarcely detected. Particularly, as the concentration of the primer DNAs was lower, the production of the byproducts tended to be suppressed. In Lane 39, amplification of DNA was hardly detected, possibly due to the too low concentration of the primer DNAs. Further, if the concentration of the primer DNAs was the same, the amount of amplification of the desired nucleic acid tended to be increased as compared with the cases in which PCR was carried out without adding the T.th.RecA protein.

In contrast, among Lanes 32, 34, 36, 38 and 40 in which PCR was carried out without adding the T.th.RecA protein, except in Lane 40, not only the desired nucleic acid but also byproducts were detected. In Lane 40, amplification of DNA was hardly detected, possibly due to the too low concentration of the primer DNAs.

From these results, if PCR is carried out with the addition of T.th.RecA protein, amplification of byproducts can be suppressed to low levels without decreasing the yield of the desired nucleic acid. In other words, by the presence of the T.th.RecA protein, the primer extension reaction caused by binding of the primer DNAs to a non-specific region of the template DNA is suppressed, and thus it is possible to suppress amplification of non-specific PCR products.

Further, it is possible to amplify nucleic acids in a sufficient amount even if the concentration of the primer DNAs added to the reaction solution is reduced to low levels, and by reducing the concentration of the primer DNAs to low levels, it is possible to specifically amplify the desired nucleic acid only while suppressing amplification of byproducts.

Example 4

Next, Example 4 will be explained. Explanation of the parts which are similar to those of each of the above-mentioned Examples will be omitted or simplified.

Figure 9:
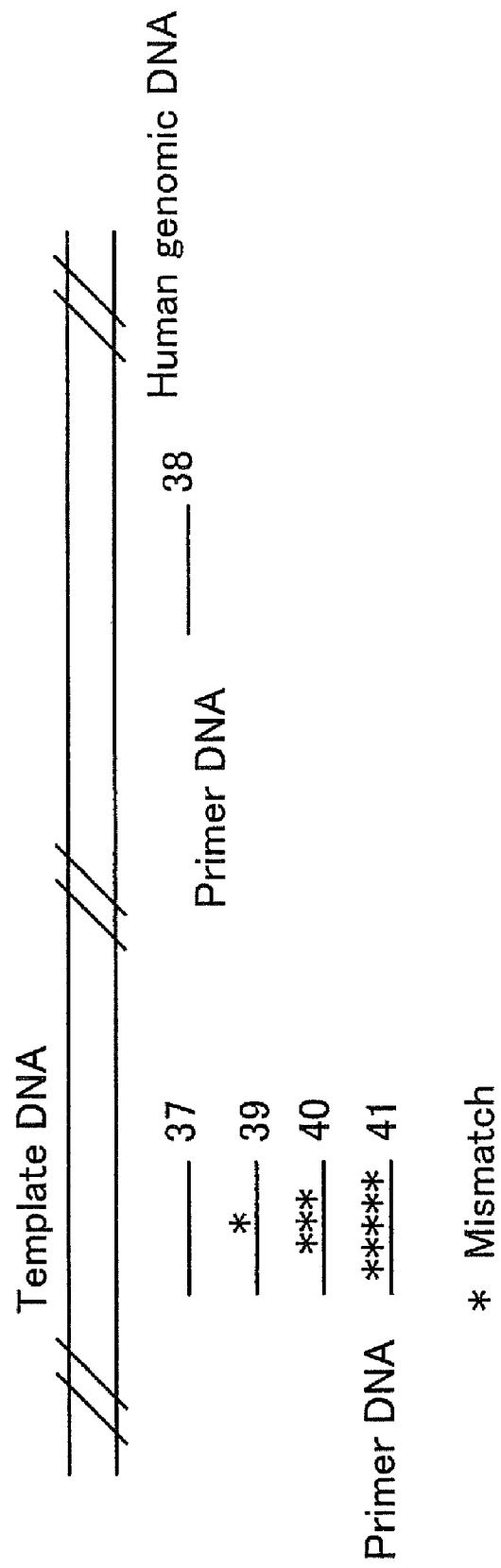
FIG. 9 is an illustrative view showing the relation between a template DNA and a primer DNA with reference to Example 4.

As shown in FIG. 9, a human genome DNA was prepared as a template DNA, and 5 kinds of oligonucleotides (Oligonucleotides 37 to 41) were prepared as the primer DNAs. Each primer DNA was designed with reference to *Homo sapiens* PAC clone RP5-1142J19 from 7q35-q36, complete sequence (Genbank accession no.; AC004975).

Among the primer DNAs, Oligonucleotides 37 and 38 consist of a 20 mer or a 21 mer base sequence, which is 100% complementary to the template DNA. On the other hand, Oligonucleotide 39 consists of a base sequence which is different by 1 base from the template DNA, while the rest is the same as Oligonucleotide 37. Further, Oligonucleotide 40 consists of a base sequence which is different by 3 base from the template DNA, while the rest is the same as Oligonucleotide 37. Further, Oligonucleotide 41 consists of a base sequence which is different by 5 base from the template DNA, while the rest is the same as Oligonucleotide 37.

```
Oligonucleotide 37:
5'-gcaggcacca agaactactg c-3'     (SEQ ID NO: 37)

Oligonucleotide 38:
5'-gcctaaggtc acgttgtccc-3'       (SEQ ID NO: 38)

Oligonucleotide 39:
5'-gcaggcacca ggaactactg c-3'     (SEQ ID NO: 39)
```

-continued

```
Oligonucleotide 40:
5'-gcaggcgcca ggaagtactg c-3'      (SEQ ID NO: 40)

Oligonucleotide 41:
5'-gcgggcgcca ggaagtacgg c-3'      (SEQ ID NO: 41)
```

Then, nucleic acids were amplified by PCR reaction in the same manner as in the above-mentioned Example 3 except that the concentration of each of the primer DNAs was set to 0.3 µM, (the final concentration). Subsequently, the reaction solution was subjected to electrophoresis with a 1% agarose gel, and the results were recorded by photography and shown in FIG. 10, in the same manner as the above-mentioned Example 1, etc.

Lane 1 shows the results when Oligonucleotide 37 and Oligonucleotide 38 were added as the primer DNAs.

Lane 2 shows the results when Oligonucleotide 39 and Oligonucleotide 38 were added as the primer DNAs.

Lane 3 shows the results when Oligonucleotide 40 and Oligonucleotide 38 were added as the primer DNAs.

Lane 4 shows the results when Oligonucleotide 41 and Oligonucleotide 38 were added as the primer DNAs.

Lane 5 shows the results when PCR was carried out in the same manner as in Lane 1 by further adding 1 mM (the final concentration) ATP-γS (Roche).

Lane 6 shows the results when PCR was carried out in the same manner as in Lane 2 by further adding 1 mM (the final concentration) ATP-γS (Roche).

Lane 7 shows the results when PCR was carried out in the same manner as in Lane 3 by further adding 1 mM (the final concentration) ATP-γS (Roche).

Lane 8 shows the results when PCR was carried out in the same manner as in Lane 4 by further adding 1 mM (the final concentration) ATP-γS (Roche).

Figure 10:
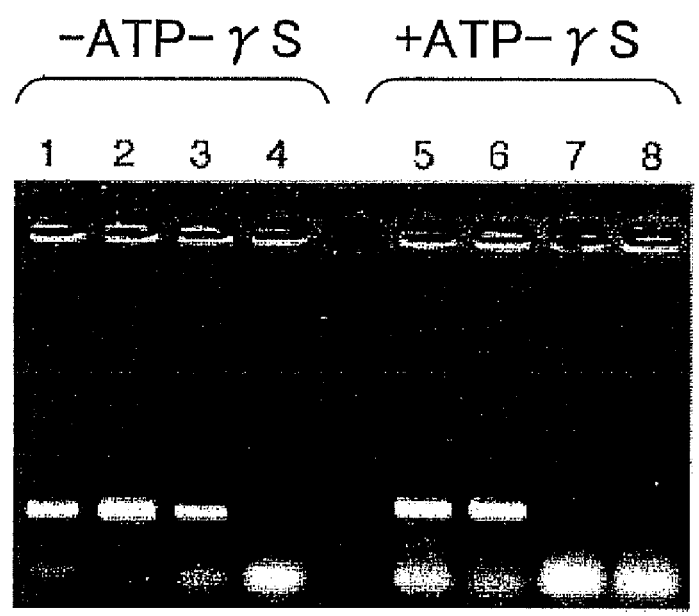
FIG. 10 is a photograph, instead of a drawing, which shows the results of the electrophoresis for the PCR reaction products with reference to Example 4.

As clearly shown in the results of FIG. 10, among Lanes 1 to 4 in which PCR was carried out without adding ATP-γS, in Lanes 1 to 3, amplification of the desired nucleic acid (the right specific PCR product) was detected whereas byproducts (non-specific PCR products) were scarcely detected. In Lane 4, amplification of DNA was scarcely detected.

In contrast, among Lanes 5 to 8 in which PCR was carried out by adding the ATP-γS, in Lanes 5 and 6, amplification of the desired DNA was detected whereas byproducts were scarcely detected. In Lane 7 and Lane 8, amplification of DNA was scarcely detected.

From these results, if PCR is carried out with the addition of T.th.RecA protein, amplification of byproducts can be suppressed to low levels without decreasing the yield of the desired nucleic acid. In other words, by the presence of the homologous recombinant protein, the primer extension reaction caused by binding of the primer DNAs to a non-specific region of the template DNA is suppressed, and thus it is possible to suppress amplification of non-specific PCR products.

Specifically, in the absence of ATP-γS, it is possible to amplify nucleic acids specifically only if there is a mismatch of 3 bases or less between the primer DNA and the template DNA. Accordingly, by adding T.th.RecA protein to the reaction solution, it is possible to amplify the desired nucleic acid more specifically.

On the other hand, in the presence of ATP-γS, it is possible to amplify nucleic acids specifically only if there is a mismatch of 1 base or less between the primer DNA and the template DNA. Accordingly, by adding ATP-γS to the reaction solution, it is possible to amplify the desired nucleic acid further specifically.

In addition, when a reagent kit for amplifying nucleic acids is prepared with a DNA polymerase, four kinds of dNTPs, a buffer solution and a homologous recombinant protein such as T.th.RecA protein and the like, it is preferable to add ATP-γS to such a kit. The reason for this is that, as clearly shown in the above-mentioned Example 4, if ATP-γS was added and PCR was carried out, it is possible to amplify the desired nucleic acid more specifically.

Further, from the results of the above-mentioned Example 4, it is possible to detect single nucleotide polymorphism. In other words, if PCR is carried out by using a primer DNA corresponding to a sequence comprising a base which forms single nucleotide polymorphism in the template DNA as one of the primer DNAs, it is possible to amplify the desired nucleic acid only when the template DNA is completely complementary to the primer DNA corresponding to a sequence comprising a base which forms single nucleotide polymorphism. On the other hand, when the template DNA is not completely complementary to the primer DNA corresponding to a sequence comprising a base which forms single nucleotide polymorphism, i.e., when the base which forms single nucleotide polymorphism is not complementary to the primer DNA, it is possible not to amplify or to inhibit amplification of the desired nucleic acid. Therefore, amplification of the desired nucleic acid by PCR allows detection of single nucleotide polymorphism.

Further, since it is possible to amplify the desired nucleic acid more specifically if ATP-γS is added, by amplification of the desired DNA, it is possible to detect single nucleotide polymorphism more reliably.

In addition, it is convenient to have a DNA polymerase, four kinds of dNTPs, a buffer solution and a homologous recombinant protein such as T.th.RecA protein and the like as a reagent kit prepared in advance for detecting single nucleotide polymorphism. By using such a kit, it is possible to detect easily single nucleotide polymorphism by PCR, just by adding the DNA polymerase, the four kinds of dNTPs, the buffer solution and the homologous recombinant protein such as T.th.RecA protein and the like to a reaction solution, and further adding the template DNA and the primer DNA prepared depending on the purpose to the reaction solution.

Further, ATP-γS is preferably also added to the above-mentioned kit. As clearly shown in the above-mentioned Example 4, if ATP-γS was added and PCR was carried out, it is possible to amplify the desired nucleic acid more specifically, and thus it is possible to detect single nucleotide polymorphism more reliably.

Example 5

Next, Example 5 will be explained. Explanation of the parts which are similar to those of each of the above-mentioned Examples will be omitted or simplified.

Figure 11:
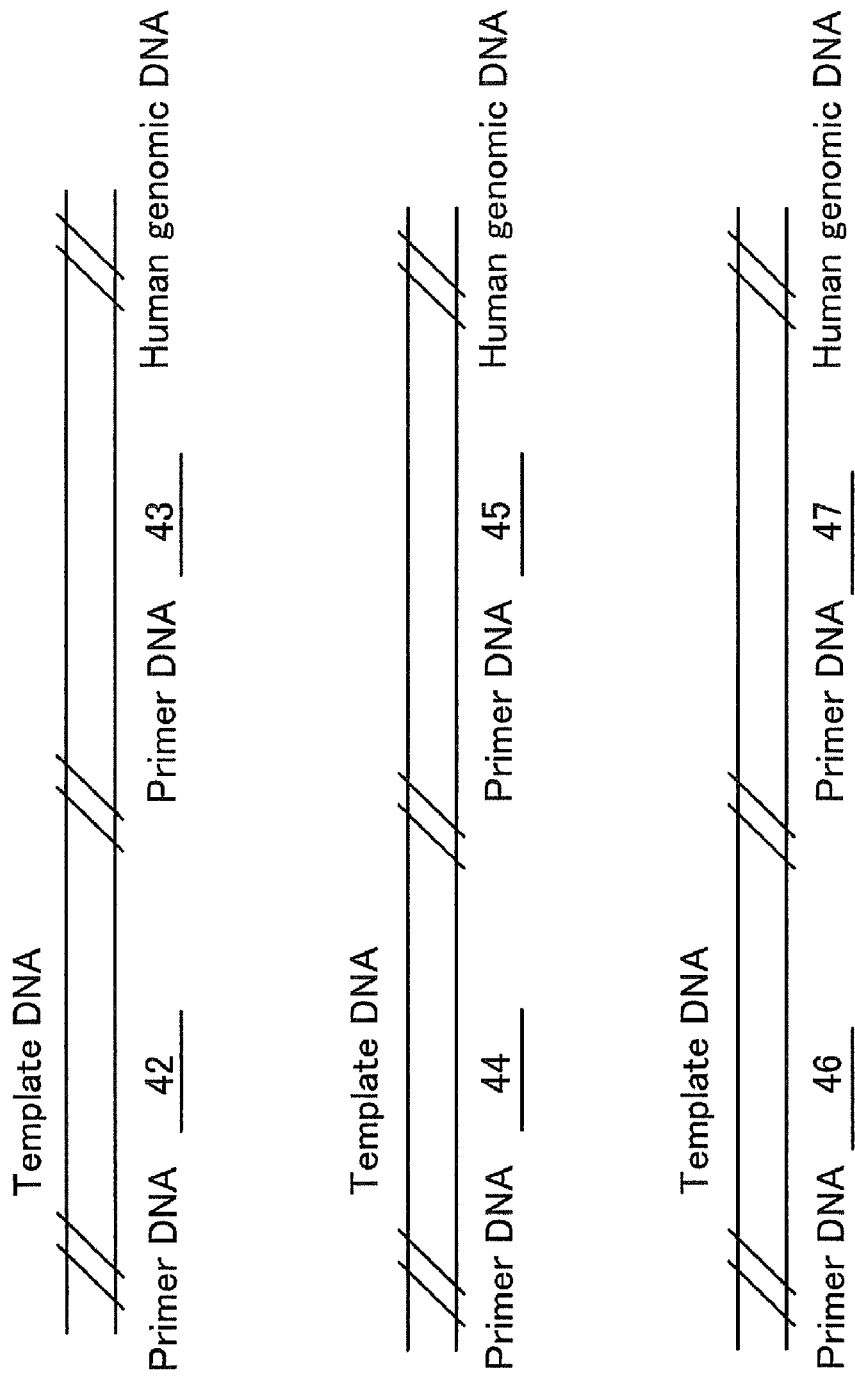
FIG. 11 is an illustrative view showing the relation between a template DNA and a primer DNA with reference to Example 5.
Figure 12:
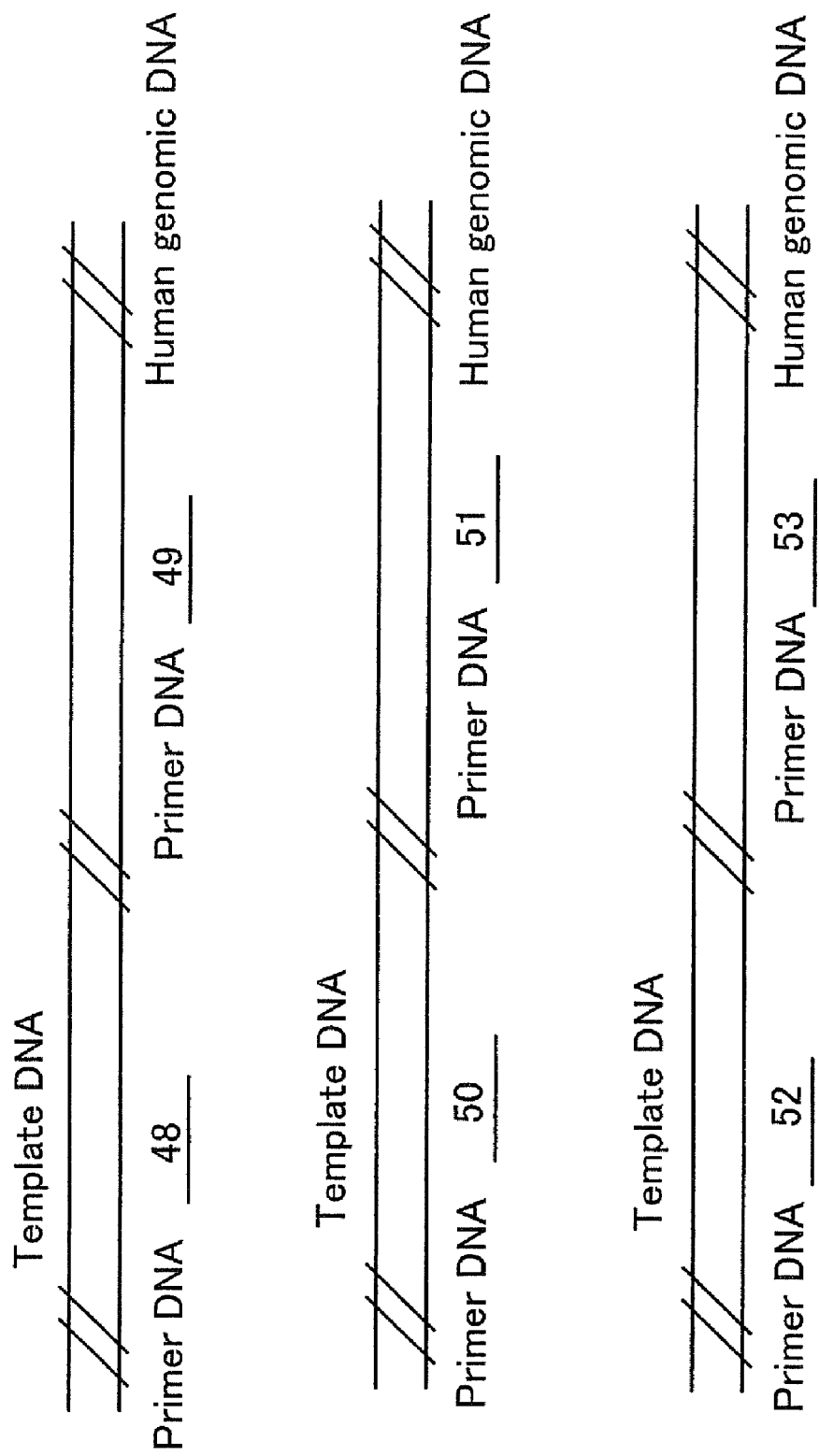
FIG. 12 is an illustrative view showing the results of the electrophoresis for the PCR reaction products with reference to Example 5.

As shown in FIG. 11 and FIG. 12, a human genome DNA was prepared as a template DNA, and 12 kinds of oligonucleotides (Oligonucleotides 42 to 53) were prepared as the primer DNAs. Specifically, Oligonucleotides 42 and 43 were designed with reference to *Homo sapiens* PAC clone RP5-1142J19 from 7q35-q36, complete sequence (Genbank accession no.; AC004975). Oligonucleotides 44 and 45 were designed with reference to *Homo sapiens* PAC clone RP5-852P6 from 7p11.2-p21, complete sequence (Genbank accession no.; AC006454). Oligonucleotides 46 and 47 were designed with reference to *Homo sapiens* PAC clone RP5-

91213 from 7, complete sequence (Genbank accession no.; AC008060). Oligonucleotides 48 and 49 were designed with reference to *Homo sapiens* BAC clone RP11-16P10 from 7, complete sequence (Genbank accession no.; AC093734, AC011786). Oligonucleotides 50 and 51 were designed with reference to *Homo sapiens* BAC clone CTB-135C18 from 7q11.2-q22, complete sequence (Genbank accession no.; AC005164). Oligonucleotides 52 and 53 were designed with reference to *Homo sapiens* PAC clone RP5-852P6 from 7p11.2-p21, complete sequence (Genbank accession no.; AC006454). Each primer DNA consists of a base sequence from a 18 mer to a 22 mer, which is 100% complementary to the template DNA.

```
Oligonucleotide 42:
5'-gcaggcacca agaactactg c-3'      (SEQ ID NO: 42)

Oligonucleotide 43:
5'-gcctaaggtc acgttgtccc-3'        (SEQ ID NO: 43)

Oligonucleotide 44:
5'-catggcacct gctctgagac-3'        (SEQ ID NO: 44)

Oligonucleotide 45:
5'-ggcactttgt gcctctctcc-3'        (SEQ ID NO: 45)

Oligonucleotide 46:
5'-ccgagtcgca tgggtgag-3'          (SEQ ID NO: 46)

Oligonucleotide 47:
5'-tttgtgcaag gaattgtggg-3'        (SEQ ID NO: 47)

Oligonucleotide 48:
5'-atctgtgtgg ttcggctctg-3'        (SEQ ID NO: 48)

Oligonucleotide 49:
5'-ctcccttaac agcagcctcc-3'        (SEQ ID NO: 49)

Oligonucleotide 50:
5'-caaagctact ttcacagcct cc-3'     (SEQ ID NO: 50)

Oligonucleotide 51:
5'-ggcatattca gccaaggatt tc-3'     (SEQ ID NO: 51)

Oligonucleotide 52:
5'-tttctggaag ggactgggtc-3'        (SEQ ID NO: 52)

Oligonucleotide 53:
5'-tcccaggatc catggagaag-3'        (SEQ ID NO: 53)
```

Then, PCR was carried out under the same conditions as those of Example 4 to amplify nucleic acids. Subsequently, the reaction solution was subjected to electrophoresis with a 1% agarose gel, and the results were recorded by photography and shown in FIG. 13 and FIG. 14, in the same manner as in Example 1, etc.

The PCR temperature condition was set to 1 cycle (at 94° C. for 1 minute), 30 cycles (at 94° C. for 30 seconds, at 60° C. for 30 seconds, and at 68° C. for 1 minute) and 1 cycle (at 68° C. for 7 minutes, and at 4° C. for 1 minute), which is referred to as Temperature Condition 1. The annealing temperature was 60° C.

Lane 1 shows the results when Oligonucleotide 42 and Oligonucleotide 43 were added as the primer DNAs.

Lane 2 shows the results when Oligonucleotide 44 and Oligonucleotide 45 were added as the primer DNAs.

Lane 3 shows the results when Oligonucleotide 46 and Oligonucleotide 47 were added as the primer DNAs.

Lane 4 shows the results when Oligonucleotide 48 and Oligonucleotide 49 were added as the primer DNAs.

Lane 5 shows the results when Oligonucleotide 50 and Oligonucleotide 51 were added as the primer DNAs.

Lane 6 shows the results when Oligonucleotide 52 and Oligonucleotide 53 were added as the primer DNAs.

Lane 7 shows the results when PCR was carried out in the same manner as in Lane 1 without adding the T.th.RecA protein.

Lane 8 shows the results when PCR was carried out in the same manner as in Lane 2 without adding the T.th.RecA protein.

Lane 9 shows the results when PCR was carried out in the same manner as in Lane 3 without adding the T.th.RecA protein.

Lane 10 shows the results when PCR was carried out in the same manner as in Lane 4 without adding the T.th.RecA protein.

Lane 11 shows the results when PCR was carried out in the same manner as in Lane 5 without adding the T.th.RecA protein.

Lane 12 shows the results when PCR was carried out in the same manner as in Lane 6 without adding the T.th.RecA protein.

For Lanes 13 to 24, the PCR temperature condition was set to 1 cycle (at 94° C. for 1 minute), 30 cycles (at 94° C. for 30 seconds, at 55° C. for 30 seconds, and at 68° C. for 1 minute) and 1 cycle (at 68° C. for 7 minutes, and at 4° C. for 1 minute), which is referred to as Temperature Condition 2. The annealing temperature was 55° C.

Lane 13 shows the results when PCR was carried out in the same manner as in Lane 1 except for the above-mentioned Temperature Condition 2.

Lane 14 shows the results when PCR was carried out in the same manner as in Lane 2 except for the above-mentioned Temperature Condition 2.

Lane 15 shows the results when PCR was carried out in the same manner as in Lane 3 except for the above-mentioned Temperature Condition 2.

Lane 16 shows the results when PCR was carried out in the same manner as in Lane 4 except for the above-mentioned Temperature Condition 2.

Lane 17 shows the results when PCR was carried out in the same manner as in Lane 5 except for the above-mentioned Temperature Condition 2.

Lane 18 shows the results when PCR was carried out in the same manner as in Lane 6 except for the above-mentioned Temperature Condition 2.

Lane 19 shows the results when PCR was carried out in the same manner as in Lane 7 except for the above-mentioned Temperature Condition 2.

Lane 20 shows the results when PCR was carried out in the same manner as in Lane 8 except for the above-mentioned Temperature Condition 2.

Lane 21 shows the results when PCR was carried out in the same manner as in Lane 9 except for the above-mentioned Temperature Condition 2.

Lane 22 shows the results when PCR was carried out in the same manner as in Lane 10 except for the above-mentioned Temperature Condition 2.

Lane 23 shows the results when PCR was carried out in the same manner as in Lane 11 except for the above-mentioned Temperature Condition 2.

Lane 24 shows the results when PCR was carried out in the same manner as in Lane 12 except for the above-mentioned Temperature Condition 2.

For Lanes 25 to 36, the PCR temperature condition was set to 1 cycle (at 94° C. for 1 minute), 30 cycles (at 94° C. for 30 seconds, at 50° C. for 30 seconds, and at 68° C. for 1 minute)

and 1 cycle (at 68° C. for 7 minutes, and at 4° C. for 1 minute), which is referred to as Temperature Condition 3. The annealing temperature was 50° C.

Lane 25 shows the results when PCR was carried out in the same manner as in Lane 1 except for the above-mentioned Temperature Condition 3.

Lane 26 shows the results when PCR was carried out in the same manner as in Lane 2 except for the above-mentioned Temperature Condition 3.

Lane 27 shows the results when PCR was carried out in the same manner as in Lane 3 except for the above-mentioned Temperature Condition 3.

Lane 28 shows the results when PCR was carried out in the same manner as in Lane 4 except for the above-mentioned Temperature Condition 3.

Lane 29 shows the results when PCR was carried out in the same manner as in Lane 5 except for the above-mentioned Temperature Condition 3.

Lane 30 shows the results when PCR was carried out in the same manner as in Lane 6 except for the above-mentioned Temperature Condition 3.

Lane 31 shows the results when PCR was carried out in the same manner as in Lane 7 except for the above-mentioned Temperature Condition 3.

Lane 32 shows the results when PCR was carried out in the same manner as in Lane 8 except for the above-mentioned Temperature Condition 3.

Lane 33 shows the results when PCR was carried out in the same manner as in Lane 9 except for the above-mentioned Temperature Condition 3.

Lane 34 shows the results when PCR was carried out in the same manner as in Lane 10 except for the above-mentioned Temperature Condition 3.

Lane 35 shows the results when PCR was carried out in the same manner as in Lane 11 except for the above-mentioned Temperature Condition 3.

Lane 36 shows the results when PCR was carried out in the same manner as in Lane 12 except for the above-mentioned Temperature Condition 3.

For Lanes 37 to 48, the PCR temperature condition was set to 1 cycle (at 94° C. for 1 minute), 30 cycles (at 94° C. for 30 seconds, at 45° C. for 30 seconds, and at 68° C. for 1 minute) and 1 cycle (at 68° C. for 7 minutes, and at 4° C. for 1 minute), which is referred to as Temperature Condition 4. The annealing temperature was 45° C.

Lane 37 shows the results when PCR was carried out in the same manner as in Lane 1 except for the above-mentioned Temperature Condition 4.

Lane 38 shows the results when PCR was carried out in the same manner as in Lane 2 except for the above-mentioned Temperature Condition 4.

Lane 39 shows the results when PCR was carried out in the same manner as in Lane 3 except for the above-mentioned Temperature Condition 4.

Lane 40 shows the results when PCR was carried out in the same manner as in Lane 4 except for the above-mentioned Temperature Condition 4.

Lane 41 shows the results when PCR was carried out in the same manner as in Lane 5 except for the above-mentioned Temperature Condition 4.

Lane 42 shows the results when PCR was carried out in the same manner as in Lane 6 except for the above-mentioned Temperature Condition 4.

Lane 43 shows the results when PCR was carried out in the same manner as in Lane 7 except for the above-mentioned Temperature Condition 4.

Lane 44 shows the results when PCR was carried out in the same manner as in Lane 8 except for the above-mentioned Temperature Condition 4.

Lane 45 shows the results when PCR was carried out in the same manner as in Lane 9 except for the above-mentioned Temperature Condition 4.

Lane 46 shows the results when PCR was carried out in the same manner as in Lane 10 except for the above-mentioned Temperature Condition 4.

Lane 47 shows the results when PCR was carried out in the same manner as in Lane 11 except for the above-mentioned Temperature Condition 4.

Lane 48 shows the results when PCR was carried out in the same manner as in Lane 12 except for the above-mentioned Temperature Condition 4.

As clearly shown in the results of FIG. 13(A), in Lanes 1 to 6 in which PCR was carried out with the addition of T.th.RecA protein at the annealing temperature of 60° C., amplification of the desired nucleic acid (the right specific PCR product) was detected whereas byproducts (non-specific PCR products) were scarcely detected.

In contrast, in some lanes among Lanes 7 to 12 in which PCR was carried out without adding the T.th.RecA protein, not only the desired nucleic acid but also byproducts were slightly detected. In addition, in some other lanes, nucleic acid amplification was scarcely detected. The reason is considered to be that the amplification region among the template DNA has an inhibitory or suppressive secondary structure.

Further, as clearly shown in the results of FIG. 13(B), in Lanes 13 to 18 in which PCR was carried out with the addition of T.th.RecA protein at the annealing temperature of 55° C., amplification of the desired nucleic acid was detected whereas byproducts were scarcely detected.

In contrast, in some lanes among Lanes 19 to 24 in which PCR was carried out without adding the T.th.RecA protein, not only the desired nucleic acid but also byproducts were slightly detected. In addition, in some other lanes, nucleic acid amplification was scarcely detected. The reason is considered to be that the amplification region among the template DNA has an inhibitory or suppressive secondary structure.

As clearly shown in the results of FIG. 14(A), in some lanes among Lanes 25 to 30 in which PCR was carried out with the addition of T.th.RecA protein at the annealing temperature of 50° C., amplification of the desired nucleic acid was detected whereas byproducts were scarcely detected. Further, in some other lanes, not only the desired nucleic acid but also byproducts were detected. However, the amount of amplification of the byproducts was smaller than in the cases in which PCR was carried out without adding the T.th.RecA protein.

In contrast, in some lanes among Lanes 31 to 36 in which PCR was carried out without adding the T.th.RecA protein, not only the desired nucleic acid but also byproducts were detected in a large amount. In addition, in some other lanes, nucleic acid amplification was scarcely detected. The reason is considered to be that the amplification region among the template DNA has an inhibitory or suppressive secondary structure.

Further, as clearly shown in the results of FIG. 14(B), in Lanes 37 to 42 in which PCR was carried out with the addition of T.th.RecA protein at the annealing temperature of 45° C., amplification of the desired nucleic acid was observed and byproducts were also detected. However, the amount of amplification of the byproducts was smaller than in the cases in which PCR was carried out without adding the T.th.RecA protein.

In contrast, in some lanes among Lanes 43 to 48 in which PCR was carried out without adding the T.th.RecA protein, not only the desired nucleic acid but also byproducts were detected in a large amount. In addition, in some other lanes, nucleic acid amplification was scarcely detected. The reason is considered to be that the amplification region among the template DNA has an inhibitory or suppressive secondary structure.

From these results, if PCR is carried out with the addition of T.th.RecA protein, amplification of byproducts can be suppressed to low levels without decreasing the yield of the desired nucleic acid. In other words, by the presence of the homologous recombinant protein, the primer extension reaction caused by binding of the primer DNAs to a non-specific region of the template DNA is suppressed, and thus it is possible to suppress amplification of non-specific PCR products.

Further, if PCR is carried out with the addition of T.th.RecA protein, it is possible to amplify the desired nucleic acid efficiently and specifically even when the template DNA has a region of the inhibitory or suppressive secondary structure. The reason is considered to be that the inhibitory or suppressive secondary structure is released by binding of the homologous recombinant protein to the template DNA.

Further, since the PCR specificity is high, it is possible to specifically amplify the desired nucleic acid even when the temperature conditions of the primer extension reaction (the annealing temperature) are changed. That is, in the cases in which PCR is carried out without adding the T.th.RecA protein, when the temperature conditions of the primer extension reaction (the annealing temperature) are set to be low, not only the desired nucleic acid, but also byproducts are amplified in a large amount. However, if PCR is carried out with the addition of T.th.RecA protein, it is possible to amplify the desired nucleic acid more specifically.

Example 6

Next, Example 6 will be explained. Explanation of the parts which are similar to those of each of the above-mentioned Examples will be omitted or simplified.

Figure 15:
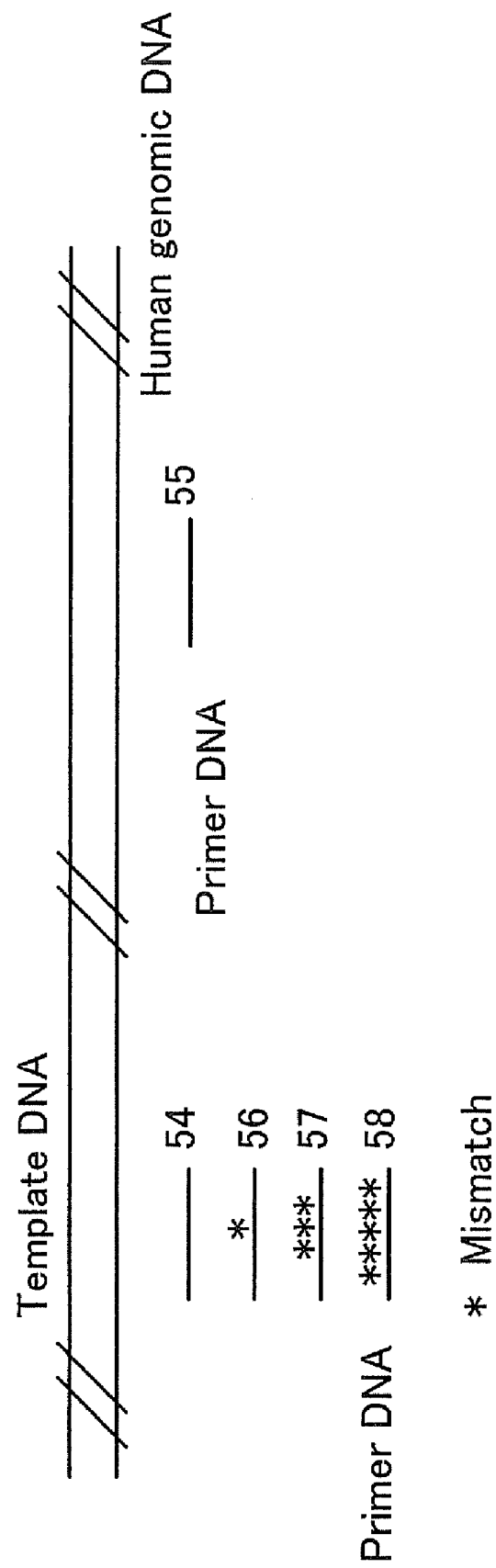
FIG. 15 is an illustrative view showing the relation between a template DNA and a primer DNA with reference to Example 6.

A human genome DNA was prepared as a template DNA, and 5 kinds of oligonucleotides (Oligonucleotides 37 to 41) which are the same as those of Example 4 (see FIG. 9), and 5 kinds of oligonucleotides (Oligonucleotides 54 to 58) as shown in FIG. 15, were prepared as the primer DNAs.

As shown in FIG. 15, the latter 5 kinds of the primer DNAs were designed with reference to *Homo sapiens* BAC clone CTB-135C18 (Genbank accession no.; AC005164). Among these primer DNAs, Oligonucleotides 54 and 55 consist of a 22 mer base sequence which is 100% complementary to the template DNA. Oligonucleotide 56 consists of a base sequence which is different by 1 base from the template DNA, while other parts are the same as Oligonucleotide 54. Oligonucleotide 57 consists of a base sequence which is different by 3 bases from the template DNA, while other parts are the same as Oligonucleotide 54. Oligonucleotide 58 consists of a base sequence which is different by 5 bases from the template DNA, while other parts are the same as Oligonucleotide 54.

```
Oligonucleotide 54:
5'-caaagctact ttcacagcct cc-3'      (SEQ ID NO: 54)

Oligonucleotide 55:
5'-ggcatattca gccaaggatt tc-3'      (SEQ ID NO: 55)

Oligonucleotide 56:
5'-caaagctact tgcacagcct cc-3'      (SEQ ID NO: 56)

Oligonucleotide 57:
5'-caaagctgct tgcacggcct cc-3'      (SEQ ID NO: 57)

Oligonucleotide 58:
5'-caaggctgct tgcacggccg cc-3'      (SEQ ID NO: 58)
```

Then, PCR was carried out under the same conditions as those of Example 4, etc. to amplify nucleic acids. Subsequently, the reaction solution was subjected to electrophoresis with a 1% agarose gel, and the results were recorded by photography and shown in FIG. 16 in the same manner as in Example 1, etc.

Lane 5 shows the results when Oligonucleotide 37 and Oligonucleotide 38 were added as the primer DNAs.

Lane 6 shows the results when Oligonucleotide 39 and Oligonucleotide 38 were added as the primer DNAs.

Lane 7 shows the results when Oligonucleotide 40 and Oligonucleotide 38 were added as the primer DNAs.

Lane 8 shows the results when Oligonucleotide 41 and Oligonucleotide 38 were added as the primer DNAs.

Lane 9 shows the results when PCR was carried out in the same manner as in Lane 5 by further adding 1 mM (the final concentration) ATP-γS.

Lane 10 shows the results when PCR was carried out in the same manner as in Lane 6 by further adding 1 mM (the final concentration) ATP-γS.

Lane 11 shows the results when PCR was carried out in the same manner as in Lane 7 by further adding 1 mM (the final concentration) ATP-γS.

Lane 12 shows the results when PCR was carried out in the same manner as in Lane 8 by further adding 1 mM (the final concentration) ATP-γS.

Lane 1 shows the results when PCR was carried out in the same manner as in Lane 5, except that 1 mM (the final concentration) ATP-γS was added without adding the T.th.RecA protein.

Lane 2 shows the results when PCR was carried out in the same manner as in Lane 6, except that 1 mM (the final concentration) ATP-γS was added without adding the T.th.RecA protein.

Lane 3 shows the results when PCR was carried out in the same manner as in Lane 7, except that 1 mM (the final concentration) ATP-γS was added without adding the T.th.RecA protein.

Lane 4 shows the results when PCR was carried out in the same manner as in Lane 8, except that 1 mM (the final concentration) ATP-γS was added without adding the T.th.RecA protein.

Lane 17 shows the results when Oligonucleotide 54 and Oligonucleotide 55 were added as the primer DNAs.

Lane 18 shows the results when Oligonucleotide 56 and Oligonucleotide 55 were added as the primer DNAs.

Lane 19 shows the results when Oligonucleotide 57 and Oligonucleotide 55 were added as the primer DNAs.

Lane 20 shows the results when Oligonucleotide 58 and Oligonucleotide 55 were added as the primer DNAs.

Lane 21 shows the results when 1 mM (the final concentration) ATP-γS was further added and PCR was carried out in the same manner as in Lane 17.

Lane 22 shows the results when 1 mM (the final concentration) ATP-γS was further added and PCR was carried out in the same manner as in Lane 18.

Lane 23 shows the results when 1 mM (the final concentration) ATP-γS was further added and PCR was carried out in the same manner as in Lane 19.

Lane 24 shows the results when 1 mM (the final concentration) ATP-γS was further added and PCR was carried out in the same manner as in Lane 20.

Lane 13 shows the results when PCR was carried out in the same manner as in Lane 17 except that 1 mM (the final concentration) ATP-γS was added without adding the T.th.RecA protein.

Lane 14 shows the results when PCR was carried out in the same manner as in Lane 18 except that 1 mM (the final concentration) ATP-γS was added without adding the T.th.RecA protein.

Lane 15 shows the results when PCR was carried out in the same manner as in Lane 19 except that 1 mM (the final concentration) ATP-γS was added without adding the T.th.RecA protein.

Lane 16 shows the results when PCR was carried out in the same manner as in Lane 20 except that 1 mM (the final concentration) ATP-γS was added without adding the T.th.RecA protein.

As clearly shown in the results of FIG. 16(A), in Lanes 5 to 8 in which PCR was carried out with the addition of T.th.RecA protein but without adding ATP-γS, amplification of the desired DNA (the right specific PCR product) was detected whereas byproducts (non-specific PCR products) were scarcely detected. Further, in Lane 7, amplification of the desired nucleic acid was smaller than those of Lane 5 and Lane 6, and further, in Lane 8, amplification of the desired nucleic acid was small.

In contrast, among Lanes 9 to 12 in which PCR was carried out with the addition of T.th.RecA protein and the ATP-γS, in Lanes 9 to 11, amplification of the desired DNA was detected whereas byproducts were hardly detected. On the other hand, in Lane 12, nucleic acid amplification was not detected. Also, in Lane 11, amplification of the desired nucleic acid was smaller than those of Lanes 9 and 10. Further, in Lane 11, amplification of the desired nucleic acid was smaller than that of the above-mentioned Lane 7.

On the other hand, in Lanes 1 to 4 in which PCR was carried out with the addition of ATP-γS but without the addition of T.th.RecA protein, amplification of not only the desired DNA but also byproducts was detected in a large amount.

Further, as clearly shown in the results of FIG. 16(B), among Lanes 17 to 20 in which PCR was carried out with the addition of T.th.RecA protein but without the addition of ATP-γS, in Lanes 17 to 19, amplification of the desired nucleic acid was detected whereas byproducts were scarcely detected. In Lane 20, amplification of the desired nucleic acid was scarcely detected. Further, in Lane 19, amplification of the desired nucleic acid was smaller than in that of Lane 17 and Lane 18.

In contrast, among Lanes 21 to 24 in which PCR was carried out with the addition of T.th.RecA protein and ATP-γS, in Lane 21, amplification of the desired nucleic acid was detected, whereas byproducts were scarcely detected. On the other hand, in Lanes 22 to 24, nucleic acid amplification was scarcely detected.

On the other hand, in Lanes 13 to 16 in which PCR was carried out with the addition of ATP-γS but without adding the T.th.RecA protein, amplification of not only the desired nucleic acid but also byproducts was detected in a large amount.

From these results, if PCR is carried out with the addition of T.th.RecA protein, amplification of byproducts can be suppressed to low levels without decreasing the yield of the desired nucleic acid. In other words, by the presence of the homologous recombinant protein, the primer extension reaction caused by binding of the primer DNAs to a non-specific region of the template DNA is suppressed, and thus it is possible to suppress amplification of non-specific PCR products.

Specifically, in the absence of ATP-γS, it is possible to amplify nucleic acids specifically only if there is a mismatch of 3 bases or less between the primer DNA and the template DNA. Accordingly, by adding T.th.RecA protein to the reaction solution, it is possible to amplify the desired nucleic acid more specifically.

On the other hand, in the presence of ATP-γS, it is possible to amplify nucleic acids specifically only if there is a mismatch of 1 base or less between the primer DNA and the template DNA. Accordingly, by adding ATP-γS to the reaction solution, it is possible to amplify the desired nucleic acid further specifically.

Further, it can be said that ATP-γS can increase the specificity of PCR when T.th.RecA protein is added, but ATP-γS alone in the absence of T.th.RecA protein cannot increase the specificity of PCR.

Further, from the results of this Example, it is possible to detect single nucleotide polymorphism. In other words, if PCR is carried out by using a primer DNA corresponding to a sequence comprising a base which forms single nucleotide polymorphism in the template DNA as one of the primer DNAs, it is possible to amplify the desired nucleic acid only when the template DNA is completely complementary to the primer DNA corresponding to the sequence comprising the base which forms single nucleotide polymorphism. On the other hand, when the template DNA is not completely complementary to the primer DNA corresponding to the sequence comprising the base which forms single nucleotide polymorphism, i.e., when the base which forms single nucleotide polymorphism is not complementary to the primer DNA, it is possible not to amplify or to inhibit amplification of the desired nucleic acid. Therefore, amplification of the desired nucleic acid by PCR allows detection of single nucleotide polymorphism.

Further, since it is possible to amplify the desired nucleic acid more specifically if ATP-γS is added, by amplification of the desired DNA, it is possible to detect single nucleotide polymorphism more reliably.

Example 7

Next, Example 7 will be explained. Explanation of the parts which are similar to those of each of the above-mentioned Examples will be omitted or simplified.

A human genome DNA was prepared as a template DNA, and some of the oligonucleotides (Oligonucleotides 38 to 40) which were used in Example 4, were prepared as the primer DNAs (see FIG. 9).

Then, PCR was carried out under the same conditions as those of Example 4, etc. to amplify nucleic acids. Subsequently, the reaction solution was subjected to electrophoresis with a 1% agarose gel, and the results were recorded by photography and shown in FIG. 17 to FIG. 19, in the same manner as in Example 1, etc.

Lane 1 shows the results when Oligonucleotide 39 and Oligonucleotide 38 were added as the primer DNAs.

Lane 2 shows the results when PCR was carried out in the same manner as in Lane 1 except that the RecA protein of *E. coli* was added instead of the T.th.RecA protein.

Lane 3 shows the results when PCR was carried out in the same manner as in Lane 1 except that the T.th.SSB protein was added instead of the T.th.RecA protein.

Lane 4 shows the results when PCR was carried out in the same manner as in Lane 1 except that the T.th.RecA protein was not added.

Lane 5 shows the results when Oligonucleotide 40 and Oligonucleotide 38 were added as the primer DNAs.

Lane 6 shows the results when PCR was carried out in the same manner as in Lane 5 except that the RecA protein of *E. coli* was added instead of the T.th.RecA protein.

Lane 7 shows the results when PCR was carried out in the same manner as in Lane 5 except that the T.th.SSB protein was added instead of the T.th.RecA protein.

Lane 8 shows the results when PCR was carried out in the same manner as in Lane 5 except that the T.th.RecA protein was not added.

Lane 9 shows the results when PCR was carried out in the same manner as in Lane 1 except that the primer DNAs were added after completing the first 1 cycle of the primer extension reaction, and then 30 cycles of the primer extension reaction was carried out.

Lane 10 shows the results when PCR was carried out in the same manner as in Lane 2 except that the primer DNAs were added after completing the first 1 cycle of the primer extension reaction, and then 30 cycles of the primer extension reaction was carried out.

Lane 11 shows the results when PCR was carried out in the same manner as in Lane 3 except that the primer DNAs were added after completing the first 1 cycle of the primer extension reaction, and then 30 cycles of the primer extension reaction was carried out.

Lane 12 shows the results when PCR was carried out in the same manner as in Lane 4 except that the primer DNAs were added after completing the first 1 cycle of the primer extension reaction, and then 30 cycles of the primer extension reaction was carried out.

Lane 13 shows the results when PCR was carried out in the same manner as in Lane 5 except that the primer DNAs were added after completing the first 1 cycle of the primer extension reaction, and then 30 cycles of the primer extension reaction was carried out.

Lane 14 shows the results when PCR was carried out in the same manner as in Lane 6 except that the primer DNAs were added after completing the first 1 cycle of the primer extension reaction, and then 30 cycles of the primer extension reaction was carried out.

Lane 15 shows the results when PCR was carried out in the same manner as in Lane 7 except that the primer DNAs were added after completing the first 1 cycle of the primer extension reaction, and then 30 cycles of the primer extension reaction was carried out.

Lane 16 shows the results when PCR was carried out in the same manner as in Lane 8 except that the primer DNAs were added after completing the first 1 cycle of the primer extension reaction, and then 30 cycles of the primer extension reaction was carried out.

Lane 17 shows the results when PCR was carried out in the same manner as in Lane 1 except that the primer DNAs were added after completing the first 3 cycles of the primer extension reaction, and then 30 cycles of the primer extension reaction was carried out.

Lane 18 shows the results when PCR was carried out in the same manner as in Lane 2 except that the primer DNAs were added after completing the first 3 cycles of the primer extension reaction, and then 30 cycles of the primer extension reaction was carried out.

Lane 19 shows the results when PCR was carried out in the same manner as in Lane 3 except that the primer DNAs were added after completing the first 3 cycles of the primer extension reaction, and then 30 cycles of the primer extension reaction was carried out.

Lane 20 shows the results when PCR was carried out in the same manner as in Lane 4 except that the primer DNAs were added after completing the first 3 cycles of the primer extension reaction, and then 30 cycles of the primer extension reaction was carried out.

Lane 21 shows the results when PCR was carried out in the same manner as in Lane 5 except that the primer DNAs were added after completing the first 3 cycles of the primer extension reaction, and then 30 cycles of the primer extension reaction was carried out.

Lane 22 shows the results when PCR was carried out in the same manner as in Lane 6 except that the primer DNAs were added after completing the first 3 cycles of the primer extension reaction, and then 30 cycles of the primer extension reaction was carried out.

Lane 23 shows the results when PCR was carried out in the same manner as in Lane 7 except that the primer DNAs were added after completing the first 3 cycles of the primer extension reaction, and then 30 cycles of the primer extension reaction was carried out.

Lane 24 shows the results when PCR was carried out in the same manner as in Lane 8 except that the primer DNAs were added after completing the first 3 cycles of the primer extension reaction, and then 30 cycles of the primer extension reaction was carried out.

Lane 25 shows the results when PCR was carried out in the same manner as in Lane 1 except that the primer DNAs were added after completing the first 6 cycles of the primer extension reaction, and then 30 cycles of the primer extension reaction was carried out.

Lane 26 shows the results when PCR was carried out in the same manner as in Lane 2 except that the primer DNAs were added after completing the first 6 cycles of the primer extension reaction, and then 30 cycles of the primer extension reaction was carried out.

Lane 27 shows the results when PCR was carried out in the same manner as in Lane 3 except that the primer DNAs were added after completing the first 6 cycles of the primer extension reaction, and then 30 cycles of the primer extension reaction was carried out.

Lane 28 shows the results when PCR was carried out in the same manner as in Lane 4 except that the primer DNAs were added after completing the first 6 cycles of the primer extension reaction, and then 30 cycles of the primer extension reaction was carried out.

Lane 29 shows the results when PCR was carried out in the same manner as in Lane 5 except that the primer DNAs were added after completing the first 6 cycles of the primer extension reaction, and then 30 cycles of the primer extension reaction was carried out.

Lane 30 shows the results when PCR was carried out in the same manner as in Lane 6 except that the primer DNAs were added after completing the first 6 cycles of the primer extension reaction, and then 30 cycles of the primer extension reaction was carried out.

Lane 31 shows the results when PCR was carried out in the same manner as in Lane 7 except that the primer DNAs were added after completing the first 6 cycles of the primer extension reaction, and then 30 cycles of the primer extension reaction was carried out.

Lane 32 shows the results when PCR was carried out in the same manner as in Lane 8 except that the primer DNAs were added after completing the first 6 cycles of the primer extension reaction, and then 30 cycles of the primer extension reaction was carried out.

Lane 33 shows the results when PCR was carried out in the same manner as in Lane 1 except that the primer DNAs were added after completing the first 10 cycles of the primer extension reaction, and then 30 cycles of the primer extension reaction was carried out.

Lane 34 shows the results when PCR was carried out in the same manner as in Lane 2 except that the primer DNAs were added after completing the first 10 cycles of the primer extension reaction, and then 30 cycles of the primer extension reaction was carried out.

Lane 35 shows the results when PCR was carried out in the same manner as in Lane 3 except that the primer DNAs were added after completing the first 10 cycles of the primer extension reaction, and then 30 cycles of the primer extension reaction was carried out.

Lane 36 shows the results when PCR was carried out in the same manner as in Lane 4 except that the primer DNAs were added after completing the first 10 cycles of the primer extension reaction, and then 30 cycles of the primer extension reaction was carried out.

Lane 37 shows the results when PCR was carried out in the same manner as in Lane 5 except that the primer DNAs were added after completing the first 10 cycles of the primer extension reaction, and then 30 cycles of the primer extension reaction was carried out.

Lane 38 shows the results when PCR was carried out in the same manner as in Lane 6 except that the primer DNAs were added after completing the first 10 cycles of the primer extension reaction, and then 30 cycles of the primer extension reaction was carried out.

Lane 39 shows the results when PCR was carried out in the same manner as in Lane 7 except that the primer DNAs were added after completing the first 10 cycles of the primer extension reaction, and then 30 cycles of the primer extension reaction was carried out.

Lane 40 shows the results when PCR was carried out in the same manner as in Lane 8 except that the primer DNAs were added after completing the first 10 cycles of the primer extension reaction, and then 30 cycles of the primer extension reaction was carried out.

Lane 41 shows the results when PCR was carried out in the same manner as in Lane 1 except that the primer DNAs were added after completing the first 15 cycles of the primer extension reaction, and then 30 cycles of the primer extension reaction was carried out.

Lane 42 shows the results when PCR was carried out in the same manner as in Lane 2 except that the primer DNAs were added after completing the first 15 cycles of the primer extension reaction, and then 30 cycles of the primer extension reaction was carried out.

Lane 43 shows the results when PCR was carried out in the same manner as in Lane 3 except that the primer DNAs were added after completing the first 15 cycles of the primer extension reaction, and then 30 cycles of the primer extension reaction was carried out.

Lane 44 shows the results when PCR was carried out in the same manner as in Lane 4 except that the primer DNAs were added after completing the first 15 cycles of the primer extension reaction, and then 30 cycles of the primer extension reaction was carried out.

Lane 45 shows the results when PCR was carried out in the same manner as in Lane 5 except that the primer DNAs were added after completing the first 15 cycles of the primer extension reaction, and then 30 cycles of the primer extension reaction was carried out.

Lane 46 shows the results when PCR was carried out in the same manner as in Lane 6 except that the primer DNAs were added after completing the first 15 cycles of the primer extension reaction, and then 30 cycles of the primer extension reaction was carried out.

Lane 47 shows the results when PCR was carried out in the same manner as in Lane 7 except that the primer DNAs were added after completing the first 15 cycles of the primer extension reaction, and then 30 cycles of the primer extension reaction was carried out.

Lane 48 shows the results when PCR was carried out in the same manner as in Lane 8 except that the primer DNAs were added after completing the first 15 cycles of the primer extension reaction, and then 30 cycles of the primer extension reaction was carried out.

As clearly shown in the results of FIG. 17(A), in Lane 1 in which PCR was carried out with the addition of T.th.RecA protein, amplification of the desired DNA (the right specific PCR product) was detected whereas byproducts (non-specific PCR products) were scarcely detected. In contrast, in Lane 2, amplification of the desired nucleic acid was observed, but byproducts were also observed in some amount. Further, in Lane 3, nucleic acid amplification was scarcely detected. Further, in Lane 4, amplification of the desired DNA was observed, but byproducts were amplified in a large amount.

Similarly, in Lane 5 in which PCR was carried out with the addition of T.th.RecA protein, amplification of the desired DNA was detected whereas byproducts were scarcely detected. In contrast, in Lane 6, amplification of the desired DNA was observed, but amplification of byproducts was also observed. Further, in Lane 7, nucleic acid amplification was scarcely detected. Further, in Lane 8, amplification of the desired DNA was observed, but byproducts were also amplified in a large amount.

As clearly shown in the results of FIG. 17(B), when the primer DNAs were added after completing the first 1 cycle of the primer extension reaction, in Lane 9 in which PCR was carried out with the addition of T.th.RecA protein, amplification of the desired DNA was detected whereas byproducts were scarcely detected. In contrast, in Lane 10, amplification of the desired DNA was observed, but amplification of byproducts was also observed. Further, in Lane 11, nucleic acid amplification was detected slightly. Further, in Lane 12, amplification of the desired DNA was observed, but byproducts were also amplified in a large amount.

Similarly, in Lane 13 in which PCR was carried out with the addition of T.th.RecA protein, amplification of the desired DNA was detected whereas byproducts were scarcely detected. In contrast, in Lane 14, amplification of the desired DNA was observed, but amplification of byproducts was also observed. Further, in Lane 15, nucleic acid amplification was scarcely detected. Further, in Lane 16, amplification of the desired DNA was observed, but byproducts were also amplified in a large amount.

As clearly shown in the results of FIG. 18(A), when the primer DNAs were added after completing the first 3 cycles of the primer extension reaction, in Lane 17 in which PCR was carried out with the addition of T.th.RecA protein, amplification of the desired DNA was detected whereas byproducts were scarcely detected. In contrast, in Lane 18, amplification of the desired DNA was observed, but amplification of byproducts was also observed. Further, in Lane 19, amplification of the desired DNA was detected slightly. Further, in Lane 20, amplification of the desired nucleic acid was observed, but byproducts were also amplified in a large amount.

On the other hand, in Lane 21 in which PCR was carried out with the addition of T.th.RecA protein, amplification of the desired DNA was detected while byproducts were scarcely detected. In contrast, in Lane 22, amplification of the desired DNA was observed, but amplification of byproducts was also observed in some amount. Further, in Lane 23, nucleic acid amplification was scarcely detected. Further, in Lane 24, amplification of the desired DNA was observed, but byproducts were also amplified in a large amount.

As clearly shown in the results of FIG. 18(B), when the primer DNAs were added after completing the first 6 cycles of the primer extension reaction, in Lane 25 in which PCR was carried out with the addition of T.th.RecA protein, amplification of the desired DNA was detected whereas byproducts were scarcely detected. In contrast, in Lane 26, amplification of the desired DNA was observed, but amplification of byproducts was also observed. Further, in Lane 27, amplification of the desired DNA was observed whereas byproducts were scarcely detected. Further, in Lane 28, amplification of the desired DNA was observed, but byproducts were also amplified in a large amount.

On the other hand, in Lane 29 in which PCR was carried out with the addition of T.th.RecA protein, amplification of the desired DNA was detected whereas byproducts were scarcely detected. In contrast, in Lane 30, amplification of the desired DNA was observed, but amplification of byproducts was also observed. Further, in Lane 31, amplification of the desired DNA was observed whereas byproducts were scarcely detected. Further, in Lane 32, amplification of the desired DNA was observed, but byproducts were also amplified in a large amount.

As clearly shown in the results of FIG. 19(A), when the primer DNAs were added after completing the first 10 cycles of the primer extension reaction, in Lane 33 in which PCR was carried out with the addition of T.th.RecA protein, amplification of the desired DNA was detected whereas byproducts were scarcely detected. In contrast, in Lane 34, amplification of the desired DNA was observed, but amplification of byproducts was also detected slightly. Further, in Lane 35, amplification of the desired DNA was scarcely detected. Further, in Lane 36, amplification of the desired DNA was observed, but byproducts were also amplified in a large amount.

On the other hand, in Lane 37 in which PCR was carried out with the addition of T.th.RecA protein, amplification of the desired DNA was detected whereas byproducts were scarcely detected. In contrast, in Lane 38, amplification of the desired DNA was observed, but amplification of byproducts was also observed. Further, in Lane 39, amplification of the desired DNA was observed, but byproducts were scarcely detected. Further, in Lane 40, amplification of the desired DNA was observed, but byproducts were also amplified in a large amount.

Further, as clearly shown in the results of FIG. 19(B), when the primer DNAs were added after completing the first 15 cycles of the primer extension reaction, in Lane 41 in which PCR was carried out with the addition of T.th.RecA protein, amplification of the desired DNA was detected whereas byproducts were scarcely detected. In contrast, in Lane 42, amplification of the desired DNA was observed, but amplification of byproducts was also slightly observed. Further, in Lane 43, amplification of the desired DNA was observed whereas byproducts were scarcely detected. Further, in Lane 44, amplification of the desired DNA was observed, but byproducts were also amplified in a large amount.

On the other hand, in Lane 45 in which PCR was carried out with the addition of T.th.RecA protein, amplification of the desired DNA was detected whereas byproducts were scarcely detected. In contrast, in Lane 46, amplification of the desired DNA was observed, but amplification of byproducts was also slightly observed. Further, in Lane 47, amplification of the desired DNA was observed whereas byproducts were scarcely detected. Further, in Lane 48, amplification of the desired DNA was observed, but byproducts were also amplified in a large amount.

Firstly, from the results of FIG. 17(A), amplification of byproducts can be suppressed to low levels without decreasing the yield of the desired nucleic acid. In other words, by the presence of the homologous recombinant protein, the primer extension reaction caused by binding of the primer DNAs to a non-specific region of the template DNA is suppressed, and thus it is possible to suppress amplification of non-specific PCR products.

On the other hand, in the case where PCR was carried out with the addition of E. coli RecA protein, although the PCR specificity increased compared with that in the absence of the E. coli RecA protein, the PCR specificity did not increase as much as the case where the T.th.RecA protein was added, due to a slight production of byproducts.

Further, E. coli RecA protein is easily denatured by heat applied in the PCR cycles. For this reason, the effects of the E. coli RecA protein are considered to be easily reduced. If heat denaturation occurs as the E. coli RecA protein binds to a denatured (single-stranded) template DNA, the E. coli RecA protein remains not separated from the template DNA. As a result, the PCR reaction is inhibited. Also, in the case where the E. coli SSB protein is added, it is considered that PCR is inhibited by the phenomena similar thereto.

On the other hand, even in the case where PCR was carried out in the presence of a T.th.SSB protein, the desired nucleic acid is not amplified.

Secondly, from the results of FIG. 17(B), FIG. 18 and FIG. 19, even when the primer DNAs were added following repeated primer extension reaction cycles, i.e., even when the reaction solution was repeatedly exposed to a state of high temperature before adding the primer DNAs, the PCR specificity was not deteriorated in the case where PCR was carried out by adding T.th.RecA protein. Accordingly, it is considered that T.th.RecA protein is stable without being inactivated at high temperature.

Example 8

Next, Example 8 will be explained. Explanation of the parts which are similar to those of each of the above-mentioned Examples will be omitted or simplified.

A human genome DNA was prepared as a template DNA, and 5 kinds of the oligonucleotides (Oligonucleotides 37 to 41), in the same manner as in Example 4, were prepared as the primer DNAs (see FIG. 9).

Then, nucleic acids were amplified by PCR in the same manner as in Example 1 except that the concentration of the primer DNAs was set to 0.3 µM. The PCR temperature condition was set to 1 cycle (at 70° C. for 10 minutes, and at 94° C. for 1 minute), 30 cycles (at 94° C. for 30 seconds, at 60° C. for 30 seconds, and at 68° C. for 1 minute) and 1 cycle (at 68° C. for 7 minutes, and at 4° C. for 1 minute), which is referred to as Temperature Condition 5. The first temperature of the first cycle (the initial temperature) was 70° C. Subsequently, the reaction solution was subjected to electrophoresis with a 1% agarose gel, and the results were recorded by photography and shown in FIG. 20, in the same manner as in Example 1, etc.

Lane 5 shows the results when Oligonucleotide 37 and Oligonucleotide 38 were added as the primer DNAs.

Lane 6 shows the results when Oligonucleotide 39 and Oligonucleotide 38 were added as the primer DNAs.

Lane 7 shows the results when Oligonucleotide 40 and Oligonucleotide 38 were added as the primer DNAs.

Lane 8 shows the results when Oligonucleotide 41 and Oligonucleotide 38 are added as the primer DNA.

Lane 1 shows the results when PCR was carried out in the same manner as in Lane 5 except that the T.th.RecA protein was not added.

Lane 2 shows the results when PCR was carried out in the same manner as in Lane 6 except that the T.th.RecA protein was not added.

Lane 3 shows the results when PCR was carried out in the same manner as in Lane 7 except that the T.th.RecA protein was not added.

Lane 4 shows the results when PCR was carried out in the same manner as in Lane 8 except that the T.th.RecA protein was not added.

Lane 9 shows the results when PCR was carried out in the same manner as in Lane 5 except that the RecA protein of *E. coli* was added instead of the T.th.RecA protein.

Lane 10 shows the results when PCR was carried out in the same manner as in Lane 6 except that the RecA protein of *E. coli* was added instead of the T.th.RecA protein.

Lane 11 shows the results when PCR was carried out in the same manner as in Lane 7 except that the RecA protein of *E. coli* was added instead of the T.th.RecA protein.

Lane 12 shows the results when PCR was carried out in the same manner as in Lane 8 except that the RecA protein of *E. coli* was added instead of the T.th.RecA protein.

For Lanes 13 to 24, the PCR temperature condition was set to 1 cycle (at 80° C. for 10 minutes, and at 94° C. for 1 minute), 30 cycles (at 94° C. for 30 seconds, at 60° C. for 30 seconds, and at 68° C. for 1 minute) and 1 cycle (at 68° C. for 7 minutes, and at 4° C. for 1 minute), which is referred to as Temperature Condition 6. The first temperature of the first cycle (the initial temperature) was 80° C.

Lane 13 shows the results when PCR was carried out in the same manner as in Lane 1 except for the above-mentioned Temperature Condition 6.

Lane 14 shows the results when PCR was carried out in the same manner as in Lane 2 except for the above-mentioned Temperature Condition 6.

Lane 15 shows the results when PCR was carried out in the same manner as in Lane 3 except for the above-mentioned Temperature Condition 6.

Lane 16 shows the results when PCR was carried out in the same manner as in Lane 4 except for the above-mentioned Temperature Condition 6.

Lane 17 shows the results when PCR was carried out in the same manner as in Lane 5 except for the above-mentioned Temperature Condition 6.

Lane 18 shows the results when PCR was carried out in the same manner as in Lane 6 except for the above-mentioned Temperature Condition 6.

Lane 19 shows the results when PCR was carried out in the same manner as in Lane 7 except for the above-mentioned Temperature Condition 6.

Lane 20 shows the results when PCR was carried out in the same manner as in Lane 8 except for the above-mentioned Temperature Condition 6.

Lane 21 shows the results when PCR was carried out in the same manner as in Lane 9 except for the above-mentioned Temperature Condition 6.

Lane 22 shows the results when PCR was carried out in the same manner as in Lane 10 except for the above-mentioned Temperature Condition 6.

Lane 23 shows the results when PCR was carried out in the same manner as in Lane 11 except for the above-mentioned Temperature Condition 6.

Lane 24 shows the results when PCR was carried out in the same manner as in Lane 12 except for the above-mentioned Temperature Condition 6.

As clearly shown in the results of FIG. 20(A), when the initial temperature was set at 70° C., in Lanes 5 to 7 among Lanes 5 to 8 in which PCR was carried out with the addition of T.th.RecA protein, amplification of the desired DNA (the right specific PCR product) was detected whereas byproducts (non-specific PCR products) were scarcely detected. In contrast, in Lane 8, nucleic acid amplification was scarcely detected.

In contrast, in Lanes 9 to 11 among Lanes 9 to 12 in which PCR was carried out with the addition of *E. coli* RecA protein, amplification of the desired nucleic acid was observed, but byproducts were also observed. In Lane 12, nucleic acid amplification was scarcely detected.

On the other hand, in Lanes 1 to 4 in which PCR was carried out without adding the RecA protein, amplification of the desired DNA was observed, but amplification of byproducts was also detected in a large amount.

In addition, in the case where PCR was carried out with the addition of *E. coli* RecA protein and with the initial temperature set at 70° C., byproducts were detected in a large amount, as compared with the case where the initial temperature was not applied. Accordingly, it is considered that *E. coli* RecA protein is inactivated at 70° C.

On the other hand, in the case where PCR was carried out with the addition of T.th.RecA protein and with the initial temperature set at 70° C., byproducts were scarcely detected similarly to the case where the initial temperature was not applied. Accordingly, it is considered that T.th.RecA protein is not inactivated at 70° C.

As clearly shown in the results of FIG. 20(B), when the initial temperature was 80° C., in Lanes 17 to 19 among Lanes 17 to 20 in which PCR was carried out by adding T.th.RecA protein, amplification of the desired DNA was observed, but byproducts were detected slightly. In Lane 20, nucleic acid amplification was scarcely detected.

In contrast, in Lanes 21 to 23 among Lanes 21 to 24 in which PCR was carried out with the addition of *E. coli* RecA protein, amplification of the desired nucleic acid was observed, but byproducts were also detected. The amount of the byproducts was larger than that in the case where the T.th.RecA protein was added. In Lane 24, nucleic acid amplification was scarcely detected.

On the other hand, in Lanes 13 to 16 in which PCR was carried out without adding the RecA protein, amplification of the desired DNA was observed, but byproducts were also detected in a large amount.

Firstly, from the results of FIG. 20(A), if PCR was carried out with the addition of T.th.RecA protein, amplification of byproducts can be suppressed to low levels without decreasing the yield of the desired nucleic acid. In other words, by the presence of the homologous recombinant protein, the primer extension reaction caused by binding of the primer DNAs to a non-specific region of the template DNA is suppressed, and thus it is possible to suppress amplification of non-specific PCR products.

On the other hand, in the case where PCR was carried out with the addition of E. coli RecA protein, although the PCR specificity increased compared with that in the absence of the E. coli RecA protein, the PCR specificity did not increase as much as in the case where the T.th.RecA protein was added, due to a slight production of byproducts.

Secondly, from the results of FIG. 20(B), when the initial temperature was elevated to 80° C., even if T.th.RecA protein was added when performing PCR, the PCR specificity decreased slightly. Accordingly, it is considered that by elevating the initial temperature to 80° C., a part of the T.th.RecA proteins is inactivated.

Example 9

Next, Example 9 will be explained. Explanation of the parts which are similar to those of each of the above-mentioned Examples will be omitted or simplified.

Figure 21:
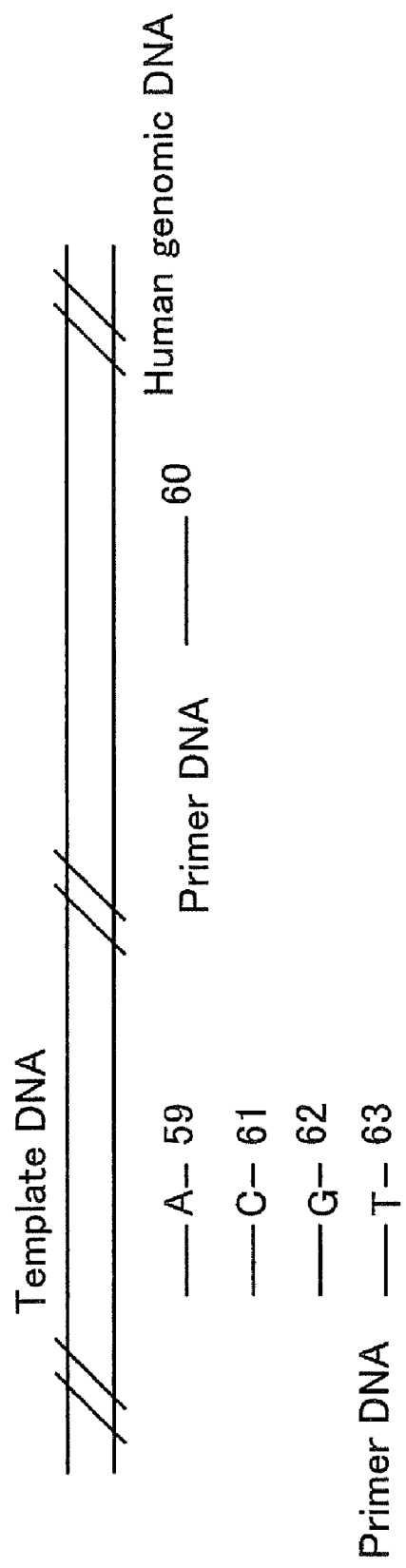
FIG. 21 is an illustrative view showing the relation between a template DNA and a primer DNA with reference to Example 9.

As shown in FIG. 21, a human genome DNA was prepared as a template DNA, and 5 kinds of oligonucleotides (Oligonucleotides 59 to 63) were prepared as the primer DNAs. Each primer DNA was designed with reference to *Homo sapiens* BAC clone CTB-135C18 from 7q11.2-q22, complete sequence (Genbank accession no.; AC005164).

Among these primer DNAs, Oligonucleotides 60 and 61 consist of a 22 mer base sequence which is 100% complementary to the template DNA. Oligonucleotide 59 is the same as Oligonucleotide 61 except that one base is changed from C to A. Oligonucleotide 62 is the same as Oligonucleotide 61 except that one base is changed from C to G. Oligonucleotide 63 is the same as Oligonucleotide 61 except that one base is changed from C to T.

```
Oligonucleotide 59:
5'-caaagctact tgcacagcct cc-3'      (SEQ ID NO: 59)

Oligonucleotide 60:
5'-ggcatattca gccaaggatt tc-3'      (SEQ ID NO: 60)

Oligonucleotide 61:
5'-caaagctact ttcacagcct cc-3'      (SEQ ID NO: 61)

Oligonucleotide 62:
5'-caaagctact tacacagcct cc-3'      (SEQ ID NO: 62)

Oligonucleotide 63:
5'-caaagctact tccacagcct cc-3'      (SEQ ID NO: 63)
```

Then, nucleic acids were amplified by PCR reaction under the same conditions as those of Example 4. Subsequently, the reaction solution was subjected to electrophoresis with a 1% agarose gel, and the results were recorded by photography and shown in FIG. 22 in the same manner as in Example 1, etc.

Lane 1 shows the results when Oligonucleotide 59 and Oligonucleotide 60 were added as the primer DNAs.

Lane 2 shows the results when Oligonucleotide 61 and Oligonucleotide 60 were added as the primer DNAs.

Lane 3 shows the results when Oligonucleotide 62 and Oligonucleotide 60 were added as the primer DNAs.

Lane 4 shows the results when Oligonucleotide 63 and Oligonucleotide 60 were added as the primer DNAs.

Lane 5 shows the results when PCR was carried out in the same manner as in Lane 1 with further adding 1 mM (the final concentration) ATP-γS.

Lane 6 shows the results when PCR was carried out in the same manner as in Lane 2 with further adding 1 mM (the final concentration) ATP-γS.

Lane 7 shows the results when PCR was carried out in the same manner as in Lane 3 with further adding 1 mM (the final concentration) ATP-γS.

Lane 8 shows the results when PCR was carried out in the same manner as in Lane 4 with further adding 1 mM (the final concentration) ATP-γS.

Figure 22:
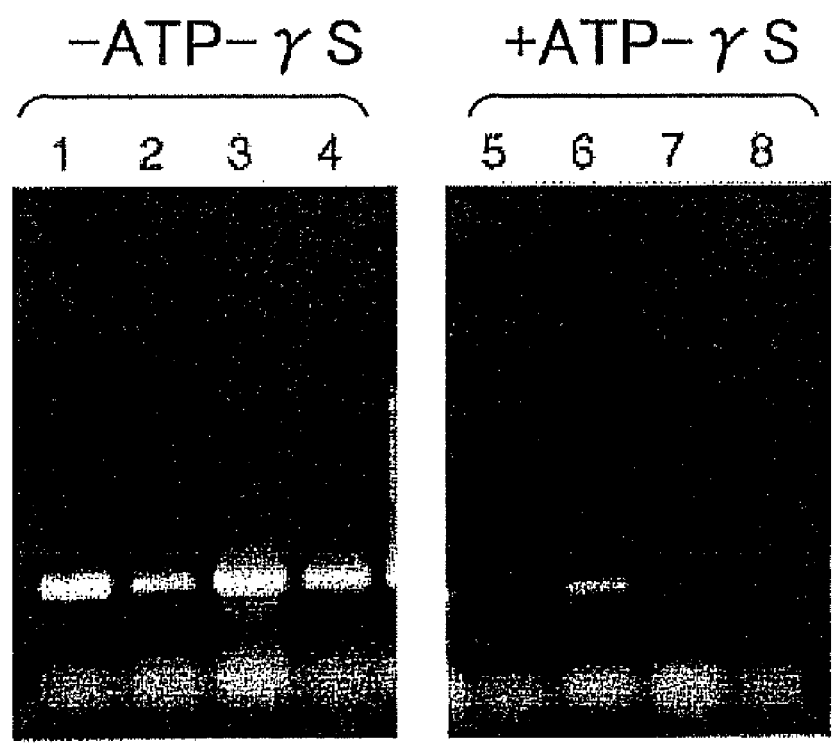
FIG. 22 is a photograph, instead of a drawing, which shows the results of the electrophoresis for the PCR reaction products with reference to Example 9. (A) is a photograph showing the case where PCR is carried out in the absence of ATP-γS, and (B) is a photograph showing the case where PCR is carried out in the presence of ATP-γS.

As clearly shown in the results of FIG. 22, in all the lanes of Lanes 1 to 4 in which PCR was carried out without adding ATP-γS, amplification of the desired DNA (the right specific PCR product) was detected whereas byproducts (non-specific PCR products) were scarcely detected.

On the other hand, in Lane 6 among Lanes 5 to 8 in which PCR was carried out by adding ATP-γS, amplification of the desired DNA was detected whereas byproducts were scarcely detected. In contrast, in Lanes 5, 7 and 8, nucleic acid amplification was scarcely detected.

From these results, if PCR is carried out with the addition of T.th.RecA protein, amplification of byproducts can be suppressed to low levels without decreasing the yield of the desired nucleic acid. In other words, by the presence of the homologous recombinant protein, the primer extension reaction caused by binding of the primer DNAs to a non-specific region of the template DNA is suppressed, and thus it is possible to suppress amplification of non-specific PCR products.

Further, in the presence of ATP-γS, it is possible to amplify nucleic acids specifically only if the primer DNAs are 100% complementary to the template DNA. Accordingly, by adding ATP-γS to the reaction solution, it is possible to amplify the desired nucleic acid further specifically.

Further, from the results of this Example, it is possible to detect single nucleotide polymorphism. In other words, if PCR is carried out by using a primer DNA corresponding to a sequence comprising a base which forms single nucleotide polymorphism in the template DNA as one of the primer DNAs, it is possible to amplify the desired nucleic acid only when the template DNA is completely complementary to the primer DNA corresponding to the sequence comprising the base which forms single nucleotide polymorphism. On the other hand, when the template DNA is not completely complementary to the primer DNA corresponding to the sequence comprising the base which forms single nucleotide polymorphism, i.e., when the base which forms single nucleotide polymorphism is not complementary to the primer DNA, it is possible not to amplify or to inhibit amplification of the desired nucleic acid. Therefore, amplification of the desired nucleic acid by PCR allows detection of single nucleotide polymorphism.

Example 10

Next, Example 10 will be explained. Explanation of the parts which are similar to those of each of the above-mentioned Examples will be omitted or simplified.

Figure 23:
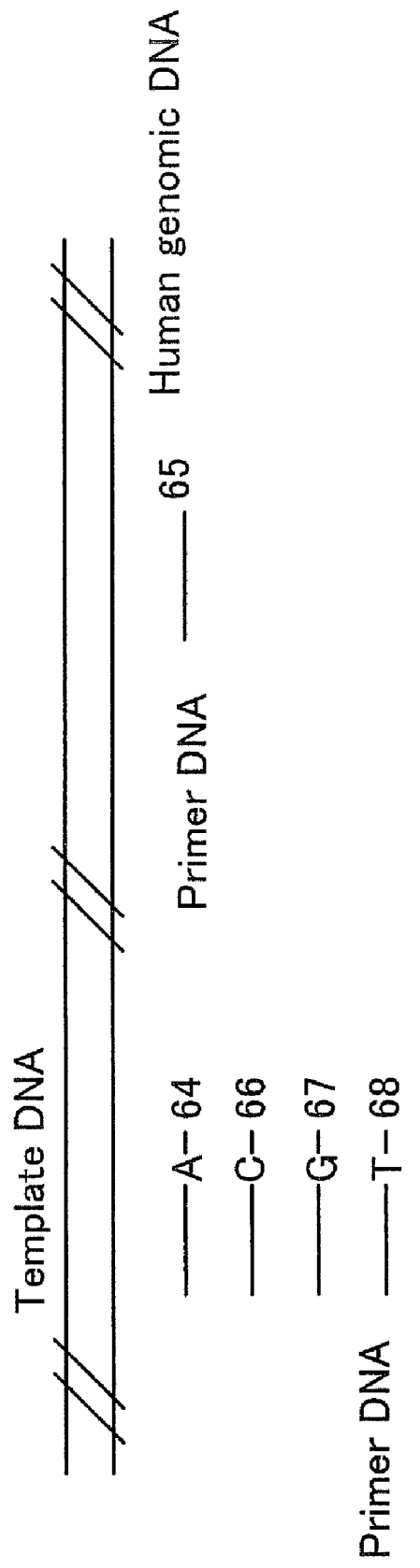
FIG. 23 is an illustrative view showing the relation between a template DNA and a primer DNA with reference to Example 10.

As shown in FIG. 23, a human genome DNA was prepared as a template DNA, and 5 kinds of oligonucleotides (Oligonucleotides 64 to 68) were prepared as the primer DNAs. Each primer DNA was designed with reference to *Homo sapiens* PAC clone RP5-1142J19 from 7q35-q36, complete sequence (Genbank accession no.; AC004975). Among these primer DNAs, Oligonucleotides 65 and 68 consist of a 20 mer or a 21 mer base sequence 100% complementary to the template DNA. Oligonucleotide 64 is the same as Oligonucleotide 68 except that the third base from the 3' end is changed from T to A. Oligonucleotide 66 is the same as Oligonucleotide 68 except that the third base from the 3' end is changed from T to C. Oligonucleotide 67 is the same as Oligonucleotide 68 except that the third base from the 3' end is changed from T to G.

```
Oligonucleotide 64:
5'-gcaggcacca agaactacag c-3'      (SEQ ID NO: 64)

Oligonucleotide 65:
5'-gcctaaggtc acgttgtccc-3'        (SEQ ID NO: 65)

Oligonucleotide 66:
5'-gcaggcacca agaactaccg c-3'      (SEQ ID NO: 66)

Oligonucleotide 67:
5'-gcaggcacca agaactacgg c-3'      (SEQ ID NO: 67)

Oligonucleotide 68:
5'-gcaggcacca agaactactg c-3'      (SEQ ID NO: 68)
```

Figure 24:
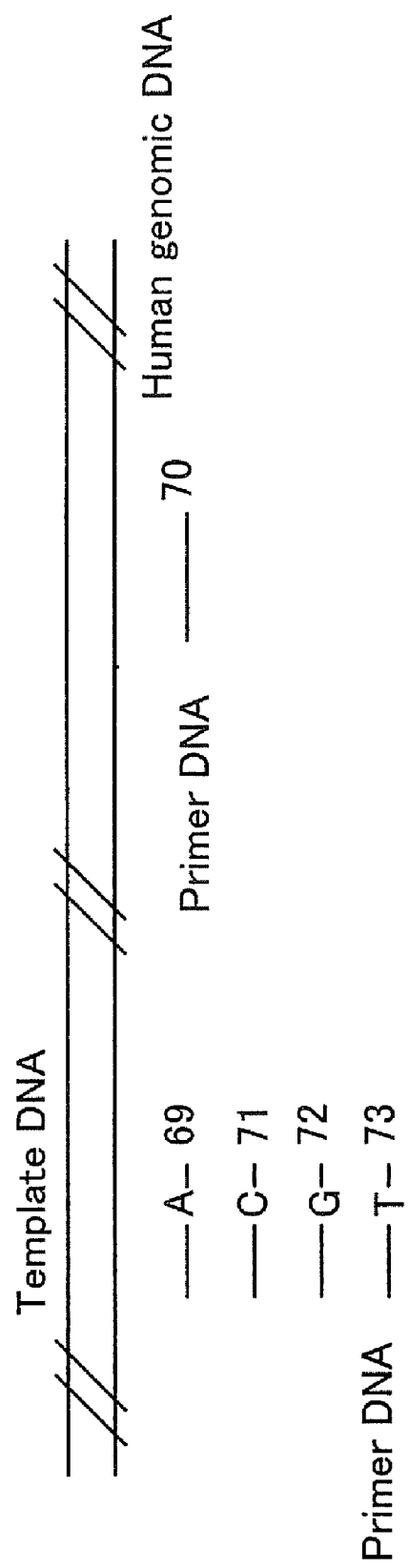
FIG. 24 is an illustrative view showing the relation between a template DNA and a primer DNA with reference to Example 10.

Further, as shown in FIG. 24, a human genome DNA was prepared as a template DNA, and 5 kinds of oligonucleotides (Oligonucleotides 69 to 73) were prepared as the primer DNAs. Each primer DNA was designed with reference to *Homo sapiens* BAC clone CTB-135C18 (Genbank accession no.; AC005164).

Among these primer DNAs, Oligonucleotides 70 and 71 consist of a 22 mer base sequence which is 100% complementary to the template DNA. Oligonucleotide 69 is the same as Oligonucleotide 71 except that the fourth base from the 3' end is changed from C to A. Oligonucleotide 72 is the same as Oligonucleotide 71 except that the fourth base from the 3' end is changed from C to G. Oligonucleotide 73 is the same as Oligonucleotide 71 except that the fourth base from the 3' end is changed from C to T.

```
Oligonucleotide 69:
5'-caaagctact ttcacagcat cc-3'     (SEQ ID NO: 69)

Oligonucleotide 70:
5'-ggcatattca gccaaggatt tc-3'     (SEQ ID NO: 70)

Oligonucleotide 71:
5'-caaagctact ttcacagcct cc-3'     (SEQ ID NO: 71)

Oligonucleotide 72:
5'-caaagctact ttcacagcgt cc-3'     (SEQ ID NO: 72)

Oligonucleotide 73:
5'-caaagctact ttcacagctt cc-3'     (SEQ ID NO: 73)
```

Figure 25:
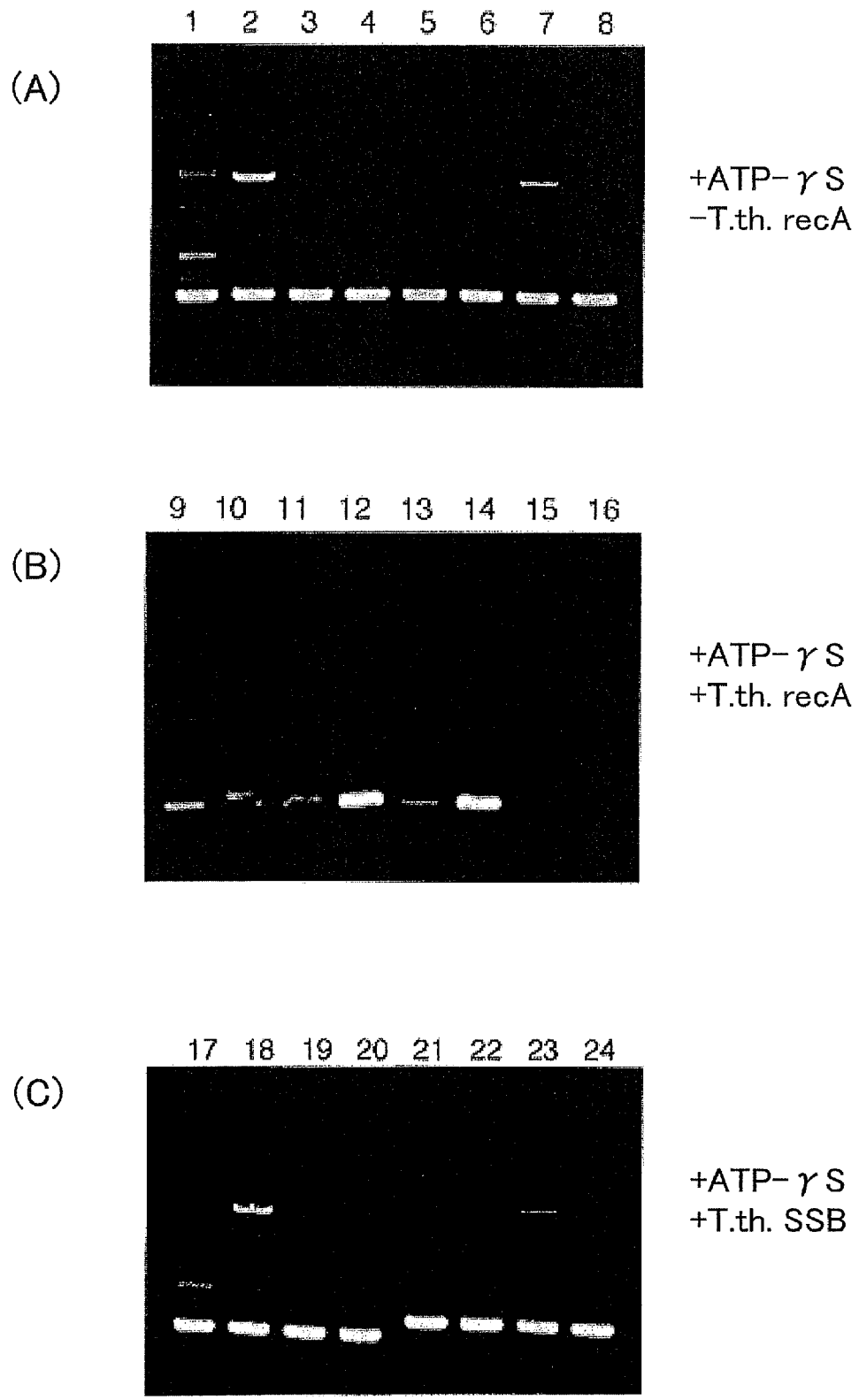
FIG. 25 is a photograph, instead of a drawing, which shows the results of the electrophoresis for the PCR reaction products with reference to Example 10. (A) is a photograph showing the case where PCR is carried out in the absence of the T.th.RecA protein, (B) is a photograph showing the case where PCR is carried out in the presence of the T.th.RecA protein, and (C) is a photograph showing the case where PCR is carried out in the presence of SSB protein.

Then, nucleic acids were amplified by PCR reaction under the same conditions as those of Example 4, etc. except that Ex Taq (Takara Bio, Inc.) was used as the DNA polymerase instead of Taq polymerase (Takara Bio, Inc.), and 1 mM (the final concentration) of ATP-γS was further added. The ExTaq is one which is known not to recognize the base sequence at the 3' end of a primer DNA. Subsequently, the reaction solution was subjected to electrophoresis with a 1% agarose gel, and the results were recorded by photography and shown in FIG. 25 in the same manner as in Example 1, etc.

Lane 9 shows the results when Oligonucleotide 64 and Oligonucleotide 65 were added as the primer DNAs.

Lane 10 shows the results when Oligonucleotide 66 and Oligonucleotide 65 were added as the primer DNAs.

Lane 11 shows the results when Oligonucleotide 67 and Oligonucleotide 65 were added as the primer DNAs.

Lane 12 shows the results when Oligonucleotide 68 and Oligonucleotide 65 were added as the primer DNAs.

Lane 13 shows the results when Oligonucleotide 69 and Oligonucleotide 70 were added as the primer DNAs.

Lane 14 shows the results when Oligonucleotide 71 and Oligonucleotide 70 were added as the primer DNAs.

Lane 15 shows the results when Oligonucleotide 72 and Oligonucleotide 70 were added as the primer DNAs.

Lane 16 shows the results when Oligonucleotide 73 and Oligonucleotide 70 were added as the primer DNAs.

Lane 1 shows the results when PCR was carried out in the same manner as in Lane 9 except that the T.th.RecA protein was not added.

Lane 2 shows the results when PCR was carried out in the same manner as in Lane 10 except that the T.th.RecA protein was not added.

Lane 3 shows the results when PCR was carried out in the same manner as in Lane 11 except that the T.th.RecA protein was not added.

Lane 4 shows the results when PCR was carried out in the same manner as in Lane 12 except that the T.th.RecA protein was not added.

Lane 5 shows the results when PCR was carried out in the same manner as in Lane 13 except that the T.th.RecA protein was not added.

Lane 6 shows the results when PCR was carried out in the same manner as in Lane 14 except that the T.th.RecA protein was not added.

Lane 7 shows the results when PCR was carried out in the same manner as in Lane 15 except that the T.th.RecA protein was not added.

Lane 8 shows the results when PCR was carried out in the same manner as in Lane 16 except that the T.th.RecA protein was not added.

Lane 17 shows the results when PCR was carried out in the same manner as in Lane 9 except that the T.th.SSB protein was added instead of the T.th.RecA protein.

Lane 18 shows the results when PCR was carried out in the same manner as in Lane 10 except that the T.th.SSB protein was added instead of the T.th.RecA protein.

Lane 19 shows the results when PCR was carried out in the same manner as in Lane 11 except that the T.th.SSB protein was added instead of the T.th.RecA protein.

Lane 20 shows the results when PCR was carried out in the same manner as in Lane 12 except that the T.th.SSB protein was added instead of the T.th.RecA protein.

Lane 21 shows the results when PCR was carried out in the same manner as in Lane 13 except that the T.th.SSB protein was added instead of the T.th.RecA protein.

Lane 22 shows the results when PCR was carried out in the same manner as in Lane 14 except that the T.th.SSB protein was added instead of the T.th.RecA protein.

Lane 23 shows the results when PCR was carried out in the same manner as in Lane 15 except that the T.th.SSB protein was added instead of the T.th.RecA protein.

Lane 24 shows the results when PCR was carried out in the same manner as in Lane 16 except that the T.th.SSB protein was added instead of the T.th.RecA protein.

As clearly shown in the results of FIG. 25(B), when T.th.RecA protein and ATP-γS were added, firstly, in Lane 12 among Lanes 9 to 12, amplification of the desired DNA was detected whereas byproducts were scarcely detected. In contrast, in Lanes 9 to 11, amplification of DNA was scarcely detected. Further, the image appearing in the photographs was considered as background. Secondly, among Lanes 13 to 16, in Lane 14, amplification of the desired DNA was detected whereas byproducts were scarcely detected. In contrast, in Lane 13 and in Lanes 15 and 16, amplification of DNAs was scarcely detected.

On the other hand, as clearly shown in the results of FIG. 25(A), when T.th.RecA protein was not added, in Lanes 1 to 4 and also in Lanes 5 to 8, amplification of DNAs corresponding to the primer DNAs was detected, and also byproducts were detected.

Further, as clearly shown in the results of FIG. 25(C), when T.th.SSB protein was added instead of the T.th.RecA protein, in Lanes 17 to 20 and also in Lanes 21 to 24, amplification of DNA corresponding to the primer DNAs was detected, and also byproducts were detected.

From these results, if PCR is carried out with the addition of T.th.RecA protein, amplification of byproducts can be suppressed to low levels without decreasing the yield of the desired nucleic acid. In other words, by the presence of the homologous recombinant protein, the primer extension reaction caused by binding of the primer DNAs to a non-specific region of the template DNA is suppressed, and thus it is possible to suppress amplification of non-specific PCR products.

Further, in the presence of ATP-γS, it is possible to amplify nucleic acids specifically only if primer DNAs are 100% complementary to the template DNA. Accordingly, by adding ATP-γS to the reaction solution, it is possible to amplify the desired nucleic acid further specifically.

Further, from the results of this Example, it is possible to detect single nucleotide polymorphism. In other words, if PCR is carried out using a primer DNA corresponding to a sequence comprising a base which forms single nucleotide polymorphism in the template DNA as one of the primer DNAs, it is possible to amplify the desired nucleic acid only when the template DNA is completely complementary to the primer DNA corresponding to the sequence comprising the base which forms single nucleotide polymorphism. On the other hand, when the template DNA is not completely complementary to the primer DNA corresponding to the sequence comprising the base which forms single nucleotide polymorphism, i.e., when the base which leads single nucleotide polymorphism is not complementary to the primer DNA, it is possible not to amplify or to inhibit amplification of the desired nucleic acid. Therefore, amplification of the desired nucleic acid by PCR allows detection of single nucleotide polymorphism.

Example 11

Next, Example 11 will be explained. Explanation of the parts which are similar to those of each of the above-mentioned Examples will be omitted or simplified.

Figure 26:
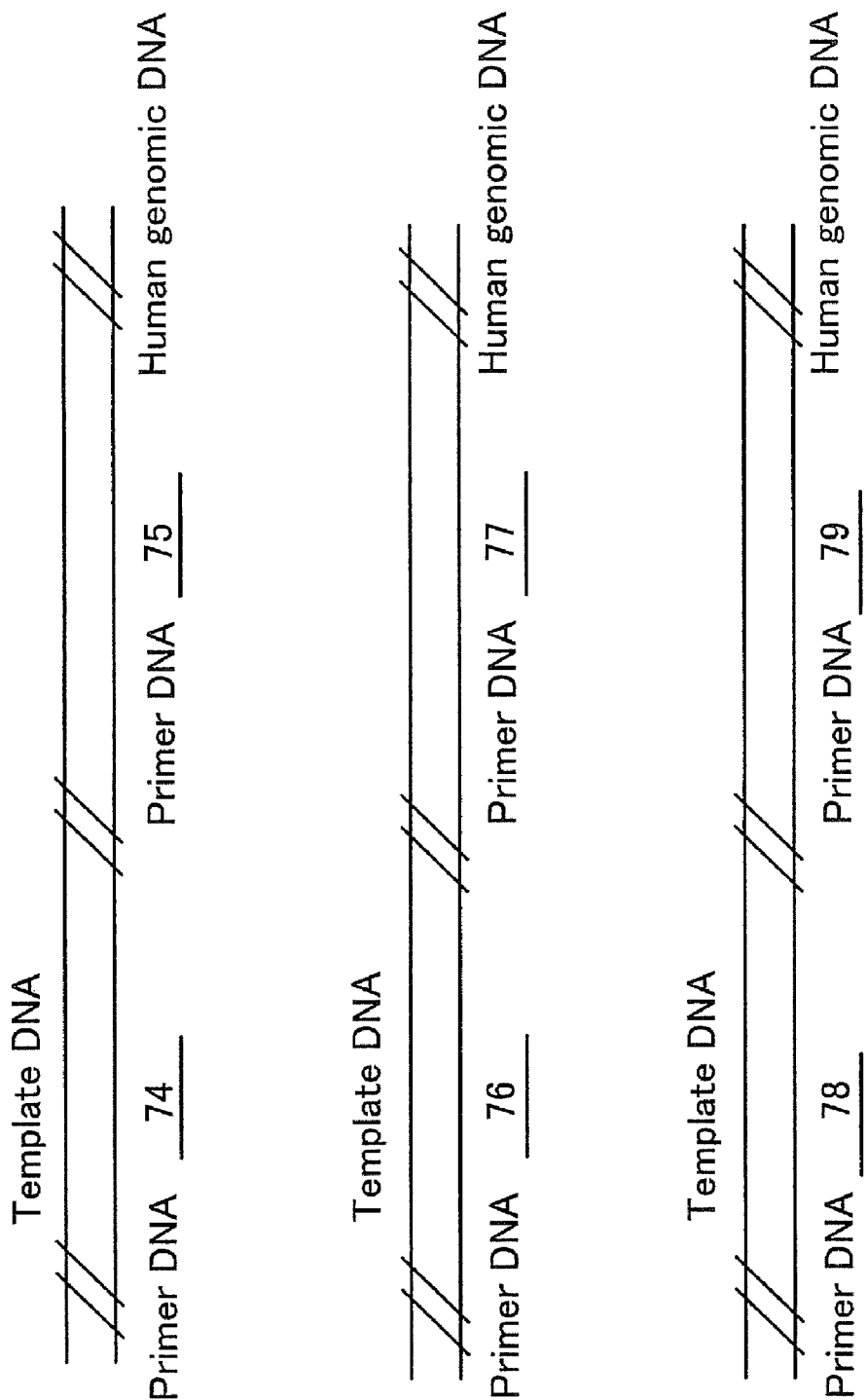
FIG. 26 is an illustrative view showing the relation between a template DNA and a primer DNA with reference to Example 11.

In this Example, as shown in FIG. 26, a human genome DNA (Promega) was prepared as a template DNA, and 6 kinds of oligonucleotides (Oligonucleotides 74 to 79) were prepared as the primer DNAs. Oligonucleotides 74 and 75 were designed with reference to Human S100 protein beta-subunit gene (Genbank accession no.; M59486, J05600). Oligonucleotides 76 and 77 were designed with reference to Homo sapiens blue cone opsin gene (Genbank accession no.; L32835). Oligonucleotides 78 and 79 were designed with reference to Homo sapiens beta globin region (Genbank accession no.; NG000007). Each primer DNA consists of a base sequence from a 20-mer to a 25-mer, which is 100% complementary to the template DNA.

```
Oligonucleotide 74:
5'-gactactctagcgactgtccatctc-3'    (SEQ ID NO: 74)

Oligonucleotide 75:
5'-gacagccaccagatccaatc-3'         (SEQ ID NO: 75)
```

```
-continued
Oligonucleotide 76:
5'-ggcagctttcatgggcactgt-3'        (SEQ ID NO: 76)

Oligonucleotide 77:
5'-gacagggctggactgacatttg-3'       (SEQ ID NO: 77)

Oligonucleotide 78:
5'-ctgctgaaagagatgcggtgg-3'        (SEQ ID NO: 78)

Oligonucleotide 79:
5'-aggaaaacagcccaagggacag-3'       (SEQ ID NO: 79)
```

Then, nucleic acids were amplified by PCR reaction. Specifically, 0.5 μM each (the final concentration) of two kinds of the oligonucleotides, 200 ng of the human genome DNA (Promega), 1.0 unit of a ExTaq-HS polymerase (Takara Bio, Inc.), 0.2 mM of a dNTP mixture solution, and 1.0 μg of the T.th.RecA protein, were mixed with 1XExTaq Buffer (Takara Bio, Inc.) in 50 μl of a PCR reaction solution. Then, PCR was carried out with 1 cycle (at 90° C. for 30 seconds), 30 cycles (at 94° C. for 15 seconds, at 55° C. for 30 seconds, and at 72° C. for 1 minute) and 1 cycle (at 72° C. for 7 minutes, and at 4° C. for 1 minute).

Figure 27:
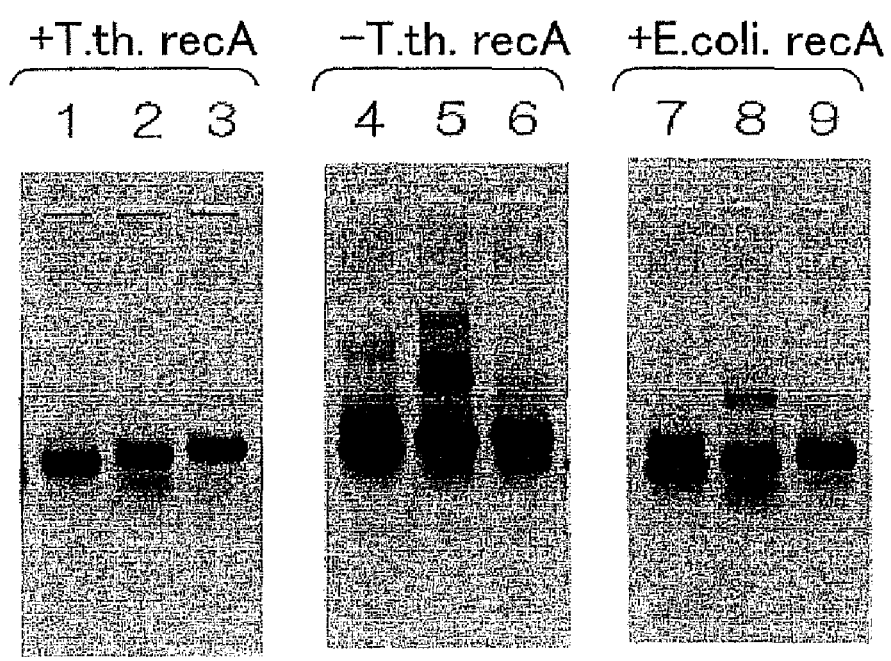
FIG. 27 is a photograph, instead of a drawing, which shows the results of the electrophoresis for the PCR reaction products with reference to Example 11.

Subsequently, 1 μl of the reaction solution was subjected to electrophoresis with a 1% agarose gel, the agarose gel was soaked in an ethidium bromide solution to stain the DNA in the gel, and then the stained DNA was recorded by photography. The results are shown in FIG. 27.

Lane 1 shows the results when Oligonucleotide 74 and Oligonucleotide 75 were added as the primer DNAs.

Lane 2 shows the results when Oligonucleotide 76 and Oligonucleotide 77 were added as the primer DNAs.

Lane 3 shows the results when Oligonucleotide 78 and Oligonucleotide 79 are added as the primer DNA.

Lane 4 shows the results when PCR was carried out in the same manner as in Lane 1 without adding the T.th.RecA protein.

Lane 5 shows the results when PCR was carried out in the same manner as in Lane 2 without adding the T.th.RecA protein.

Lane 6 shows the results when PCR was carried out in the same manner as in Lane 3 without adding the T.th.RecA protein.

Lane 7 shows the results when PCR was carried out in the same manner as in Lane 1 except that the E. coli RecA protein was added in the same amount instead of the T.th.RecA protein.

Lane 8 shows the results when PCR was carried out in the same manner as in Lane 2 except that the E. coli RecA protein was added in the same amount instead of the T.th.RecA protein.

Lane 9 shows the results when PCR was carried out in the same manner as in Lane 3 except that the E. coli RecA protein was added in the same amount instead of the T.th.RecA protein.

As clearly shown in the results of FIG. 27, in Lanes 1 to 3 in which PCR was carried out with the addition of T.th.RecA protein, amplification of the desired nucleic acid (the right specific PCR product) was detected whereas byproducts (non-specific PCR products) were scarcely detected.

In contrast, in Lanes 4 to 6 in which PCR was carried out without adding the T.th.RecA protein, not only the desired nucleic acid but byproducts were also detected in a large amount.

Further, in Lanes 7 to 9 in which PCR was carried out by adding the E. coli RecA protein instead of the T.th.RecA protein, in addition to the desired nucleic acid, byproducts were also detected although the amount is not as much as that in Lanes 4 to 6.

From these results, if PCR is carried out with the addition of T.th.RecA protein, amplification of byproducts can be suppressed to low levels without decreasing the yield of the desired nucleic acid. In other words, by the presence of the T.th.RecA protein, the primer extension reaction caused by binding of the primer DNAs to a non-specific region of the template DNA is suppressed, and thus it is possible to suppress amplification of non-specific PCR products.

On the other hand, in the case where PCR was carried out with the addition of *E. coli* RecA protein, although the PCR specificity increased compared with that in the absence of the *E. coli* RecA protein, the PCR specificity did not increase as much as in the case where the T.th.RecA protein was added, due to a slight production of byproducts.

Example 12

Next, Example 12 will be explained. Explanation of the parts which are similar to those of each of the above-mentioned Examples will be omitted or simplified.

Figure 28:
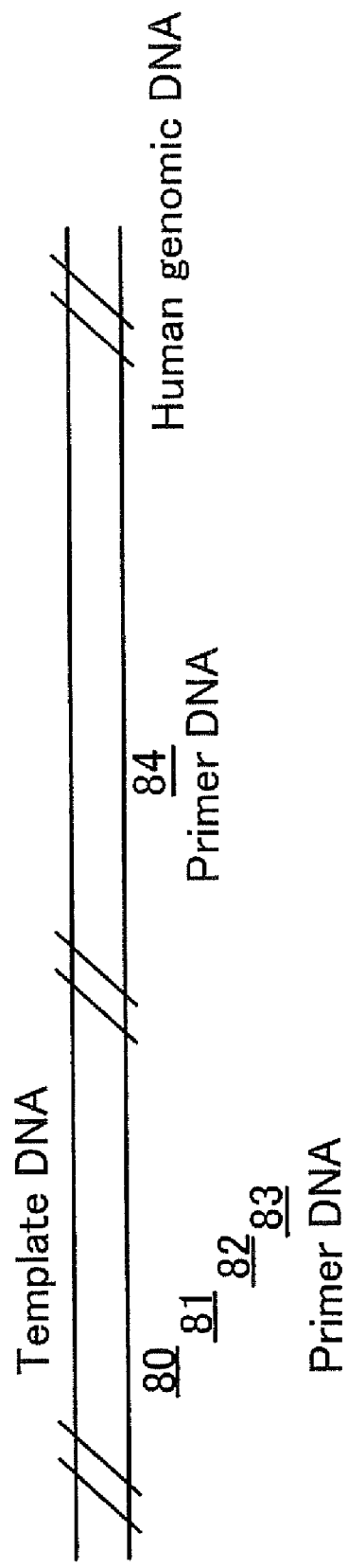
FIG. 28 is an illustrative view showing the relation between a template DNA and a primer DNA with reference to Example 12.

In this Example, as shown in FIG. 28, a human genome DNA (Promega) was prepared as a template DNA, and 5 kinds of oligonucleotides (Oligonucleotides 80 to 84) were prepared as the primer DNAs. Each primer DNA was designed with reference to *Homo sapiens* BAC clone CTB-135C18 (Genbank accession no.; AC005164) and *Homo sapiens* chromosome 19 clone CTD-2166J9 (Genbank Accession; AC010412). The primer DNAs on the forward side (Oligonucleotides 80 to 83) were designed with the respective positions staggered due to possibility of arbitrary primer design. On the other hand, the primer DNAs on the reverse side (Oligonucleotide 84) were common ones. Each primer DNA consists of a 22-mer base sequence which is 100% complementary to the template DNA.

```
Oligonucleotide 80:
5'-caaagctactttcacagcctcc-3'     (SEQ ID NO: 80)

Oligonucleotide 81:
5'-caaagctactgtcacagcctcc-3'     (SEQ ID NO: 81)

Oligonucleotide 82:
5'-caaagcgactgtcagagcctcc-3'     (SEQ ID NO: 82)

Oligonucleotide 83:
5'-cagagcgactgtcagagcgtcc-3'     (SEQ ID NO: 83)

Oligonucleotide 84:
5'-ggcatattcagccaaggatttc-3'     (SEQ ID NO: 84)
```

Then, PCR was carried out under the same conditions as those of Lane 1 of Example 11 and the like. Subsequently, the reaction solution was subjected to electrophoresis with a 1% agarose gel, and the results were recorded by photography and shown in FIG. 29, in the same manner as in Example 1 and the like.

Lane 1 shows the results when Oligonucleotide 80 and Oligonucleotide 84 were added as the primer DNAs.

Lane 2 shows the results when Oligonucleotide 81 and Oligonucleotide 84 were added as the primer DNAs.

Lane 3 shows the results when Oligonucleotide 82 and Oligonucleotide 84 were added as the primer DNAs.

Lane 4 shows the results when Oligonucleotide 83 and Oligonucleotide 84 were added as the primer DNAs.

Lane 5 shows the results when PCR was carried out in the same manner as in Lane 1 without adding the T.th.RecA protein.

Lane 6 shows the results when PCR was carried out in the same manner as in Lane 2 without adding the T.th.RecA protein.

Lane 7 shows the results when PCR was carried out in the same manner as in Lane 3 without adding the T.th.RecA protein.

Lane 8 shows the results when PCR was carried out in the same manner as in Lane 4 without adding the T.th.RecA protein.

Lane 9 shows the results when PCR was carried out in the same manner as in Lane 1 except that the *E. coli* RecA protein was added in the same amount instead of the T.th.RecA protein.

Lane 10 shows the results when PCR was carried out in the same manner as in Lane 2 except that the *E. coli* RecA protein was added in the same amount instead of the T.th.RecA protein.

Lane 11 shows the results when PCR was carried out in the same manner as in Lane 3 except that the *E. coli* RecA protein was added in the same amount instead of the T.th.RecA protein.

Lane 12 shows the results when PCR was carried out in the same manner as in Lane 4 except that the *E. coli* RecA protein was added in the same amount instead of the T.th.RecA protein.

Figure 29:
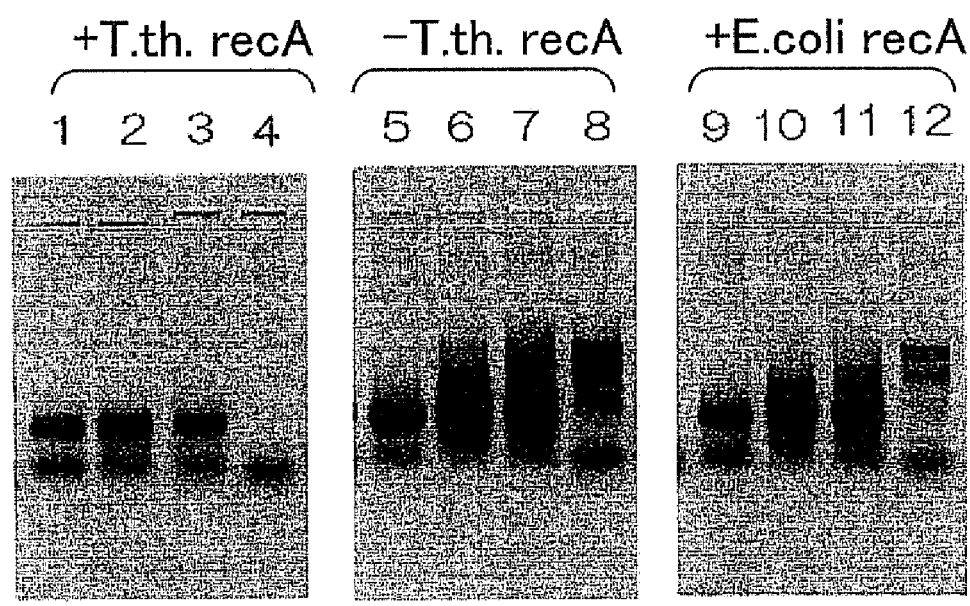
FIG. 29 is a photograph, instead of a drawing, which shows the results of the electrophoresis for the PCR reaction products with reference to Example 12.

As clearly shown in the results of FIG. 29, in Lanes 1 to 4 in which PCR was carried out with the addition of T.th.RecA protein, amplification of the desired nucleic acid (the right specific PCR product) was detected whereas byproducts (non-specific PCR products) were scarcely detected.

In contrast, in Lanes 5 to 8 in which PCR was carried out without adding the T.th.RecA protein, not only the desired nucleic acid but also byproducts were detected in a large amount.

Further, in Lanes 9 to 12 in which PCR was carried out with the addition of *E. coli* RecA protein instead of the T.th.RecA protein, in addition to the desired nucleic acid, byproducts were also detected although the amount is not as much as that in Lanes 5 to 8.

From these results, if PCR is carried out with the addition of T.th.RecA protein, amplification of byproducts can be suppressed to low levels without decreasing the yield of the desired nucleic acid. In other words, by the presence of the T.th.RecA protein, the primer extension reaction caused by binding of the primer DNAs to a non-specific region of the template DNA is suppressed, and thus it is possible to suppress amplification of non-specific PCR products.

On the other hand, in the case where PCR was carried out with the addition of *E. coli* RecA protein, although the PCR specificity increased compared with that in the absence of the *E. coli* RecA protein, the PCR specificity did not increase as much as in the case where the T.th.RecA protein was added, due to a slight production of byproducts.

Example 13

Next, Example 13 will be explained. Explanation of the parts which are similar to those of each of the above-mentioned Examples will be omitted or simplified.

Figure 30:
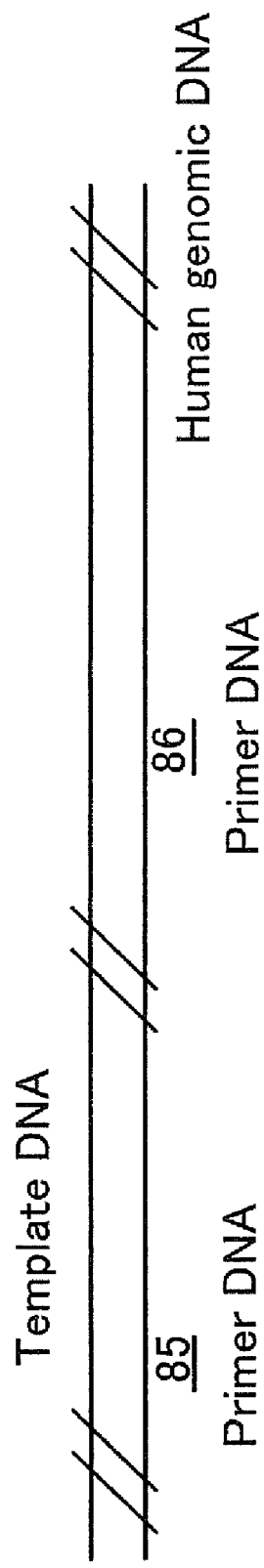
FIG. 30 is an illustrative view showing the relation between a template DNA and a primer DNA with reference to Example 13.

In this Example, as shown in FIG. 30, a human genome DNA (Promega) was prepared as a template DNA, and Oligonucleotides 85 and 86 were prepared as the primer DNAs. Each primer DNA was designed with respect to a single copy gene of the human genome DNA. Specifically, they were designed with reference to *Homo sapiens* PAC clone RP5-1142J19 (Genbank accession no.; AC004975). Each primer DNA consists of a 20 mer or a 21 mer base sequence, which is 100% complementary to the template DNA.

```
Oligonucleotide 85:
5'-gcaggcaccaagaactactgc-3'        (SEQ ID NO:85)

Oligonucleotide 86:
5'-gcctaaggtcacgttgtccc-3'         (SEQ ID NO:86)
```

Then, nucleic acids were amplified by PCR reaction. Specifically, 1.0 µM each (the final concentration) of two kinds of the oligonucleotides, 200 ng of the human genome DNA (Promega), 1.0 unit of ExTaq-HS (Takara Bio, Inc.), 0.2 mM of a dNTP mixture solution and 1.0 µg of the T.th.RecA protein, were mixed with 10 mM Tris-HCl Buffer (pH 8.3), 50 mM KCl and 1.5 mM $MgCl_2$ in 50 µl of a PCR reaction solution. Then, PCR was carried out with 1 cycle (at 90° C. for 1 minute), 30 cycles (at 94° C. for 30 seconds, at 60° C. for 30 seconds, and at 68° C. for 1 minute) and 1 cycle (at 68° C. for 7 minutes, and at 4° C. for 1 minute).

Figure 31:
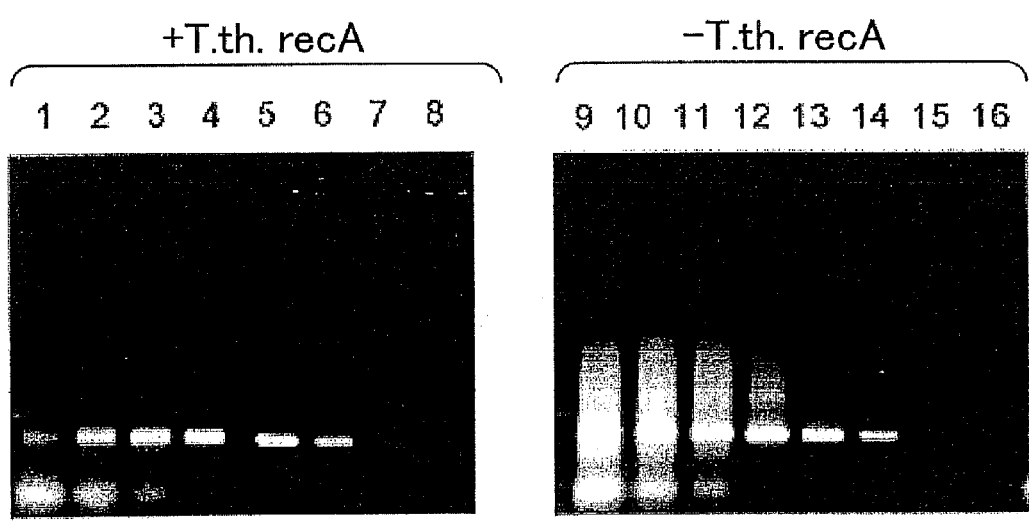
FIG. 31 is a photograph, instead of a drawing, which shows the results of the electrophoresis for the PCR reaction products with reference to Example 13.

Subsequently, the reaction solution was subjected to electrophoresis with a 1% agarose gel, the agarose gel was soaked in an ethidium bromide solution to stain DNA in the gel, and then the stained DNA was recorded by photography. The results are shown in FIG. 31.

Lane 1 shows the results when PCR was carried out with the concentration of each of the primer DNAs at 1.0 µM (the final concentration), as described above.

Lane 2 shows the results when PCR was carried out in the same manner as in Lane 1 by reducing the concentration of each of the primer DNAs to 0.3 µM (the final concentration).

Lane 3 shows the results when PCR was carried out in the same manner as in Lane 1 by reducing the concentration of each of the primer DNAs to 0.1 µM (the final concentration).

Lane 4 shows the results when PCR was carried out in the same manner as in Lane 1 by reducing the concentration of each of the primer DNAs to 0.03 µM (the final concentration).

Lane 5 shows the results when PCR was carried out in the same manner as in Lane 1 by reducing the concentration of each of the primer DNAs to 0.01 µM (the final concentration).

Lane 6 shows the results when PCR was carried out in the same manner as in Lane 1 by reducing the concentration of each of the primer DNAs to 0.003 µM (the final concentration).

Lane 7 shows the results when PCR was carried out in the same manner as in Lane 1 by reducing the concentration of each of the primer DNAs to 0.00 µM (the final concentration).

Lane 8 shows the results when PCR was carried out in the same manner as in Lane 1 by reducing the concentration of each of the primer DNAs to 0.0003 µM (the final concentration).

Lane 9 shows the results when PCR was carried out in the same manner as in Lane 1 without adding the T.th.RecA protein.

Lane 10 shows the results when PCR was carried out in the same manner as in Lane 2 without adding the T.th.RecA protein.

Lane 11 shows the results when PCR was carried out in the same manner as in Lane 3 without adding the T.th.RecA protein.

Lane 12 shows the results when PCR was carried out in the same manner as in Lane 4 without adding the T.th.RecA protein.

Lane 13 shows the results when PCR was carried out in the same manner as in Lane 5 without adding the T.th.RecA protein.

Lane 14 shows the results when PCR was carried out in the same manner as in Lane 6 without adding the T.th.RecA protein.

Lane 15 shows the results when PCR was carried out in the same manner as in Lane 7 without adding the T.th.RecA protein.

Lane 16 shows the results when PCR was carried out in the same manner as in Lane 8 without adding the T.th.RecA protein.

As clearly shown in the results of FIG. 31, in Lanes 1 to 6 among Lanes 1 to 8 in which PCR was carried out with the addition of T.th.RecA protein, amplification of the desired nucleic acid (the right specific PCR product) was detected whereas byproducts (non-specific PCR products) were scarcely detected. In Lanes 7 and 8, amplification of DNA was hardly detected, possibly due to the too low concentration of the primer DNAs.

In contrast, in Lanes 9 to 12 among Lanes 9 to 16 in which PCR was carried out without adding the T.th.RecA protein, not only the desired nucleic acid but also byproducts were detected. In Lanes 13 and 14, amplification of the desired nucleic acid was detected whereas byproducts were scarcely detected. In Lanes 15 and 16, amplification of DNA was hardly detected, possibly due to the too low concentration of the primer DNAs.

From these results, if PCR is carried out with the addition of T.th.RecA protein, amplification of byproducts can be suppressed to low levels without decreasing the yield of the desired nucleic acid. In other words, by the presence of the T.th.RecA protein, the primer extension reaction caused by binding of the primer DNAs to a non-specific region of the template DNA is suppressed, and thus it is possible to suppress amplification of non-specific PCR products.

Example 14

Next, Example 14 will be explained. Explanation of the parts which are similar to those of each of the above-mentioned Examples will be omitted or simplified.

Figure 32:
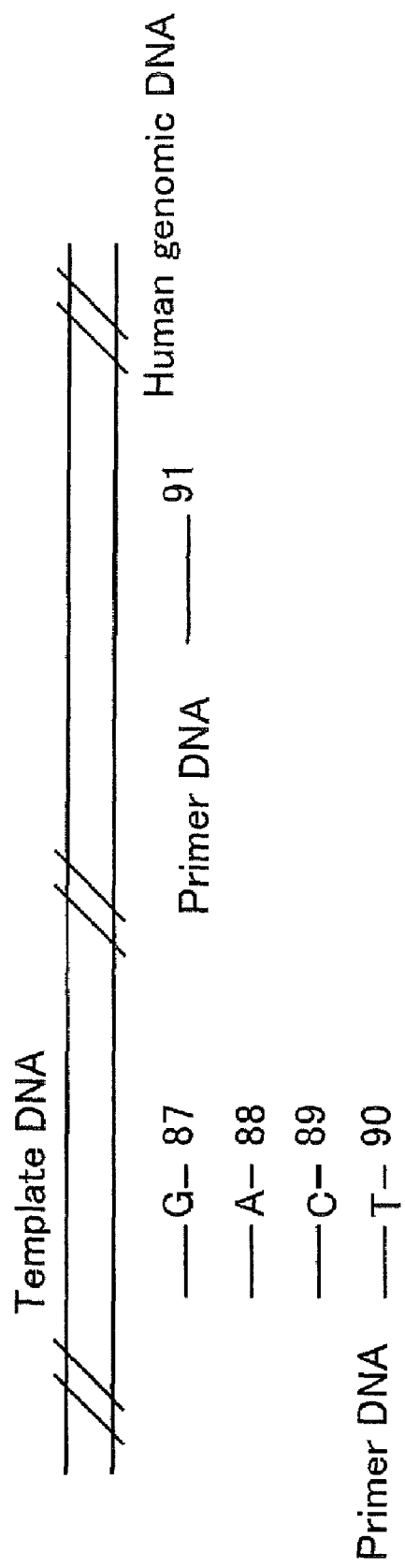
FIG. 32 is an illustrative view showing the relation between a template DNA and a primer DNA with reference to Example 14.

In this Example, as shown in FIG. 32, a human genome DNA (Promega) was prepared as a template DNA, and 5 kinds of oligonucleotides (Oligonucleotides 87 to 91) were prepared as the primer DNAs. Each primer DNA was designed with reference to *Homo sapiens* BAC clone CTB-135C18 (Genbank accession no.; AC005164). The primer DNAs at one end (Oligonucleotides 87 to 90) are ones in which the third bases from the 3' end are different, and Oligonucleotide 90 is 100% complementary to the template DNA. The primer DNA at the other end (Oligonucleotide 91) was a common one, and 100% complementary to the template DNA. Each primer DNA consists of a 22-mer base sequence which is 100% complementary to the template DNA.

```
Oligonucleotide 87:
5'-caaagctactttcacagccgcc-3'       (SEQ ID NO: 87)

Oligonucleotide 88:
5'-caaagctactttcacagccacc-3'       (SEQ ID NO: 88)

Oligonucleotide 89:
5'-caaagctactttcacagccccc-3'       (SEQ ID NO: 89)
```

-continued

```
Oligonucleotide 90:
5'-caaagctactttcacagcctcc-3'        (SEQ ID NO: 90)

Oligonucleotide 91:
5'-ggcatattcagccaaggatttc-3'        (SEQ ID NO: 91)
```

Then, nucleic acids were amplified by PCR reaction. Specifically, 0.3 μM each (the final concentration) of two kinds of the oligonucleotides, 200 ng of the human genome DNA (Promega), 1.0 unit of Taq-HS (Takara Bio, Inc.), 0.2 mM of a dNTP mixture solution and 1.0 μg of the T.th.RecA protein, were mixed with 10 mM Tris-HCl Buffer (pH 8.3), 50 mM KCl and 1.5 mM MgCl$_2$ in 50 μl of a PCR reaction solution. Then, PCR was carried out with 1 cycle (at 94° C. for 1 minute), 30 cycles (at 94° C. for 30 seconds, at 60° C. for 30 seconds, and at 68° C. for 1 minute) and 1 cycle (at 68° C. for 7 minutes, and at 4° C. for 1 minute).

Figure 33:
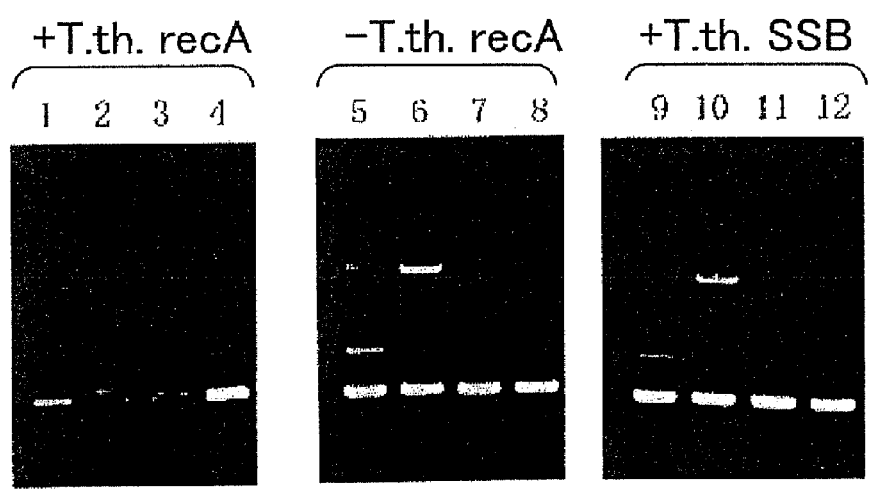
FIG. 33 is a photograph, instead of a drawing, which shows the results of the electrophoresis for the PCR reaction products with reference to Example 14.

Subsequently, the reaction solution was subjected to electrophoresis with a 1% agarose gel, the agarose gel was soaked in an ethidium bromide solution to stain DNA in the gel, and then the stained DNA was recorded by photography. The results are shown in FIG. 33.

Lane 1 shows the results when Oligonucleotide 87 and Oligonucleotide 91 were added as the primer DNAs.

Lane 2 shows the results when Oligonucleotide 88 and Oligonucleotide 91 were added as the primer DNAs.

Lane 3 shows the results when Oligonucleotide 89 and Oligonucleotide 91 were added as the primer DNAs.

Lane 4 shows the results when Oligonucleotide 90 and Oligonucleotide 91 were added as the primer DNAs.

Lane 5 shows the results when PCR was carried out in the same manner as in Lane 1 without adding the T.th.RecA protein.

Lane 6 shows the results when PCR was carried out in the same manner as in Lane 2 without adding the T.th.RecA protein.

Lane 7 shows the results when PCR was carried out in the same manner as in Lane 3 without adding the T.th.RecA protein.

Lane 8 shows the results when PCR was carried out in the same manner as in Lane 4 without adding the T.th.RecA protein.

Lane 9 shows the results when PCR was carried out in the same manner as in Lane 1 except that the T.th.SSB protein was added in the same amount instead of the T.th.RecA protein.

Lane 10 shows the results when PCR was carried out in the same manner as in Lane 2 except that the T.th.SSB protein was added in the same amount instead of the T.th.RecA protein.

Lane 11 shows the results when PCR was carried out in the same manner as in Lane 3 except that the T.th.SSB protein was added in the same amount instead of the T.th.RecA protein.

Lane 12 shows the results when PCR was carried out in the same manner as in Lane 4 except that the T.th.SSB protein was added in the same amount instead of the T.th.RecA protein.

As clearly shown in the results of FIG. 33, among Lanes 1 to 4 in which PCR was carried out with the addition of T.th.RecA protein, in Lane 4 in which the primer DNAs 100% complementary to the template DNA were used, substantial amplification of the desired DNA was detected whereas byproducts were scarcely detected. In Lanes 1 to 3 where the primer DNAs whose third bases from the 3' end were different from the template DNA, amplification of the desired nucleic acid was scarcely detected.

In contrast, in all of Lanes 5 to 8 in which PCR was carried out without adding the T.th.RecA protein, amplification of the desired DNA was detected. Further, in Lanes 5 and 6, byproducts were also detected.

Further, in all of Lanes 9 to 12 in which PCR was carried out with the addition of T.th.SSB protein instead of the T.th.RecA protein, amplification of the desired DNA was detected. Further, in Lanes 9 and 10, byproducts were also detected.

From these results, if PCR is carried out with the addition of T.th.RecA protein, amplification of byproducts can be suppressed to low levels without decreasing the yield of the desired nucleic acid. In other words, by the presence of the homologous recombinant protein, the primer extension reaction caused by binding of the primer DNAs to a non-specific region of the template DNA is suppressed, and thus it is possible to suppress amplification of non-specific PCR products. Specifically, it is possible to amplify nucleic acids specifically only if there is no base mismatch between the primer DNA and the template DNA. Generally, when a base near the 3' end of a primer DNA (especially, a base within 3 bases from the 3' end of the primer DNA) is mismatched with the template DNA, there is a tendency that nucleic acids are easily amplified. However, if PCR is carried out with the addition of T.th.RecA protein, it is possible to amplify the desired nucleic acid specifically.

On the other hand, even if PCR is carried out with the addition of a T.th.SSB protein which binds to DNA in the similar manner as the RecA protein, the PCR specificity does not increase especially.

Further, from the results of this Example, it is possible to detect single nucleotide polymorphism. In other words, if PCR is carried out by using a primer DNA corresponding to a sequence comprising a base which forms single nucleotide polymorphism in the template DNA as one of the primer DNAs, it is possible to amplify the desired nucleic acid only when the template DNA is completely complementary to the primer DNA corresponding to the sequence comprising the base which forms single nucleotide polymorphism. On the other hand, when the template DNA is not completely complementary to the primer DNA corresponding to the sequence comprising the base which forms single nucleotide polymorphism, i.e., when the base which forms single nucleotide polymorphism is not complementary to the primer DNA, it is possible not to amplify or to inhibit amplification of the desired nucleic acid. Therefore, amplification of the desired nucleic acid by PCR allows detection of single nucleotide polymorphism.

Example 15

Next, Example 15 will be explained. Explanation of the parts which are similar to those of each of the above-mentioned Examples will be omitted or simplified.

Figure 34:
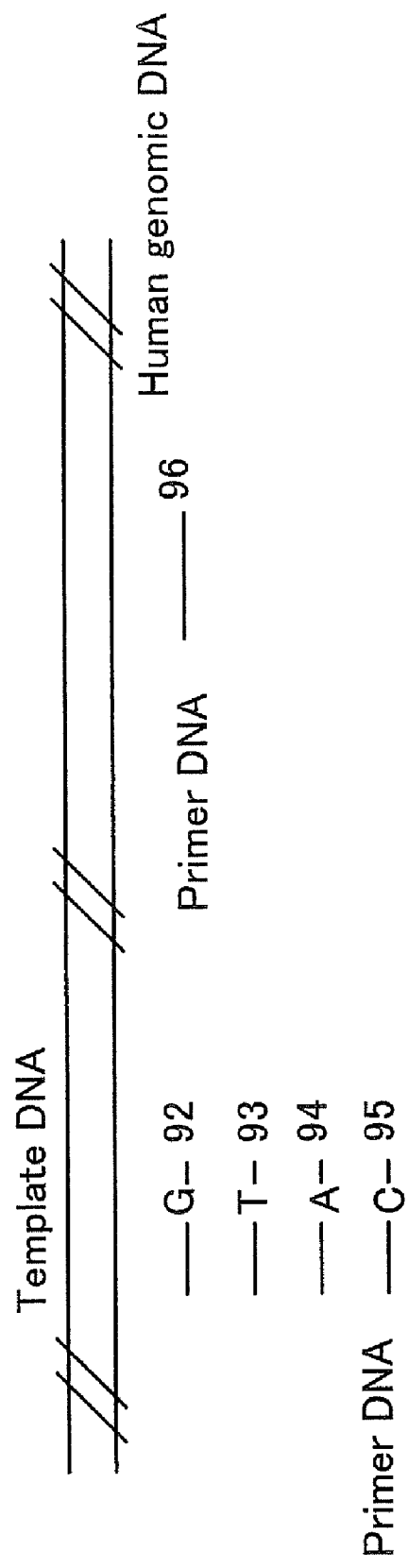
FIG. 34 is an illustrative view showing the relation between a template DNA and a primer DNA with reference to Example 15.

In this Example, as shown in FIG. 34, a human genome DNA (Promega) was prepared as a template DNA, and 5 kinds of oligonucleotides (Oligonucleotides 92 to 96) were prepared as the primer DNAs. Each primer DNA was designed with reference to *Homo sapiens* PAC clone RP5-1142J19 (Genbank accession no.; AC004975). The primer DNAs at one end (Oligonucleotides 92 to 95) are ones in which the third bases from the 3' end are different, and Oligonucleotide 93 is 100% complementary to the template DNA. The primer DNA at the other end (Oligonucleotide 96)

is a common one, and 100% complementary to the template DNA. Each primer DNA consists of a 20 mer or a 21 mer base sequence.

```
Oligonucleotide 92:
5'-gcaggcaccaagaactacggc-3'    (SEQ ID NO: 92)

Oligonucleotide 93:
5'-gcaggcaccaagaactactgc-3'    (SEQ ID NO: 93)

Oligonucleotide 94:
5'-gcaggcaccaagaactacagc-3'    (SEQ ID NO: 94)

Oligonucleotide 95:
5'-gcaggcaccaagaactaccgc-3'    (SEQ ID NO: 95)

Oligonucleotide 96:
5'-gcctaaggtcacgttgtccc-3'     (SEQ ID NO: 96)
```

Then, PCR was carried out under the same conditions as those of Lane 1 of Example 14 and the like. Subsequently, the reaction solution was subjected to electrophoresis with a 1% agarose gel, and the results were recorded by photography and shown in FIG. 35, in the same manner as in Example 14.

Lane 1 shows the results when Oligonucleotide 92 and Oligonucleotide 96 were added as the primer DNAs.

Lane 2 shows the results when Oligonucleotide 93 and Oligonucleotide 96 were added as the primer DNAs.

Lane 3 shows the results when Oligonucleotide 94 and Oligonucleotide 96 were added as the primer DNAs.

Lane 4 shows the results when Oligonucleotide 95 and Oligonucleotide 96 were added as the primer DNAs.

Lane 5 shows the results when PCR was carried out in the same manner as in Lane 1 without adding the T.th.RecA protein.

Lane 6 shows the results when PCR was carried out in the same manner as in Lane 2 without adding the T.th.RecA protein.

Lane 7 shows the results when PCR was carried out in the same manner as in Lane 3 without adding the T.th.RecA protein.

Lane 8 shows the results when PCR was carried out in the same manner as in Lane 4 without adding the T.th.RecA protein.

Lane 9 shows the results when PCR was carried out in the same manner as in Lane 1 except that the T.th.SSB protein was added in the same amount instead of the T.th.RecA protein.

Lane 10 shows the results when PCR was carried out in the same manner as in Lane 2 except that the T.th.SSB protein was added in the same amount instead of the T.th.RecA protein.

Lane 11 shows the results when PCR was carried out in the same manner as in Lane 3 except that the T.th.SSB protein was added in the same amount instead of the T.th.RecA protein.

Lane 12 shows the results when PCR was carried out in the same manner as in Lane 4 except that the T.th.SSB protein was added in the same amount instead of the T.th.RecA protein.

Figure 35:
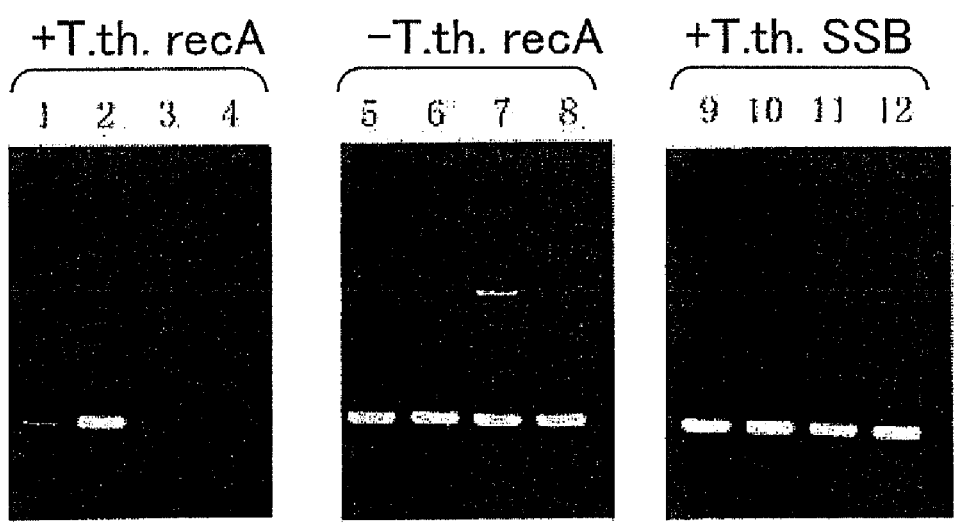
FIG. 35 is a photograph, instead of a drawing, which shows the results of the electrophoresis for the PCR reaction products with reference to Example 15.

As clearly shown in the results of FIG. 35, among Lanes 1 to 4 in which PCR was carried out with the addition of T.th.RecA protein, in Lane 2 in which the primer DNAs used were 100% complementary to the template DNA, substantial amplification of the desired DNA was detected whereas byproducts were scarcely detected. In Lanes 1, 3 and 4 where the primer DNAs whose third bases from the 3' end were different from the template DNA, amplification of the desired nucleic acid was scarcely detected.

In contrast, in all of Lanes 5 to 8 in which PCR was carried out without adding the T.th.RecA protein, amplification of the desired DNA was detected. Further, in Lane 7, byproducts were also detected.

Further, in all of Lanes 9 to 12 in which PCR was carried out with the addition of T.th.SSB protein instead of the T.th.RecA protein, amplification of the desired DNA was detected. Further, in Lane 11, byproducts were also amplified.

From these results, if PCR is carried out with the addition of T.th.RecA protein, amplification of byproducts can be suppressed to low levels without decreasing the yield of the desired nucleic acid. In other words, by the presence of the homologous recombinant protein, the primer extension reaction caused by binding of the primer DNAs to a non-specific region of the template DNA is suppressed, and thus it is possible to suppress amplification of non-specific PCR products. Specifically, it is possible to amplify nucleic acids specifically only if there is no base mismatch between the primer DNA and the template DNA. Generally, when a base near the 3' end of the primer DNA (especially, a base within 3 bases from the 3' end of the primer DNA) is mismatched with the template DNA, there is a tendency that nucleic acids are easily amplified. However, if PCR was carried out with the addition of T.th.RecA protein, it is possible to amplify the desired nucleic acid specifically.

On the other hand, even if PCR is carried out with the addition of T.th.SSB protein which binds to DNA in the similar manner as the RecA protein, the PCR specificity does not increase especially.

Further, from the results of this Example, it is possible to detect single nucleotide polymorphism. In other words, if PCR is carried out by using a primer DNA corresponding to a sequence comprising a base which forms single nucleotide polymorphism in the template DNA as one of the primer DNAs, it is possible to amplify the desired nucleic acid only when the template DNA is completely complementary to the primer DNA corresponding to the sequence comprising the base which forms single nucleotide polymorphism. On the other hand, when the template DNA is not completely complementary to the primer DNA corresponding to the sequence comprising the base which forms single nucleotide polymorphism, i.e., when the base which forms single nucleotide polymorphism is not complementary to the primer DNA, it is possible not to amplify or to inhibit amplification of the desired nucleic acid. Therefore, amplification of the desired nucleic acid by PCR allows detection of single nucleotide polymorphism.

Example 16

Next, Example 16 will be explained. Explanation of the parts which are similar to those of each of the above-mentioned Examples will be omitted or simplified.

Figure 36:
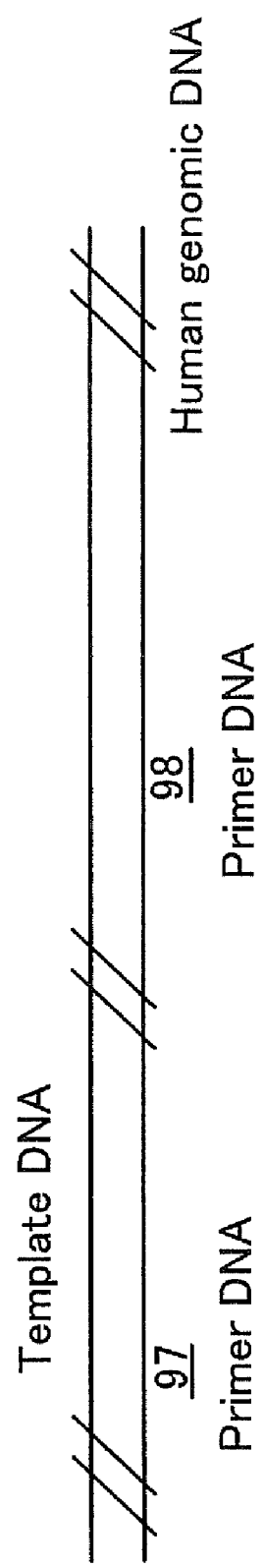
FIG. 36 is an illustrative view showing the relation between a template DNA and a primer DNA with reference to Example 16.

In this Example, as shown in FIG. 36, a human genome DNA (Promega) was prepared as a template DNA, and Oligonucleotides 97 and 98 were prepared as the primer DNAs. Each primer DNA was designed with reference to Human chromosome 14 DNA sequence BAC C-2240H23 (Genbank accession no.; AL356017). Each primer DNA consists of a 20-mer base sequence which is 100% complementary to the template DNA.

```
Oligonucleotide 97:
5'-atgaaaagccctgctttgca-3'      (SEQ ID NO: 97)

Oligonucleotide 98:
5'-agacttcttcaactcaatgg-3'      (SEQ ID NO: 98)
```

Then, nucleic acids were amplified by PCR reaction. Specifically, 0.5 μM each (final concentration) of two kinds of the oligonucleotides, 200 ng of human cDNA (Invitrogen), 1.0 unit of ExTaq-HS Polymerase (Takara Bio, Inc.), 0.2 mM of a dNTP mixture solution and 1.0 μg of the T.th.RecA protein, were mixed with 1XExTaq-HS dedicated buffer (Takara Bio, Inc.) in 50 μl of a PCR reaction solution. Then, PCR was carried out with 1 cycle (at 94° C. for 30 seconds), 30 cycles (at 94° C. for 15 seconds, at 55° C. for 30 seconds, and at 72° C. for 1 minute) and 1 cycle (at 72° C. for 7 minutes, and at 4° C. for 1 minute).

Subsequently, 10 μl of the reaction solution was subjected to electrophoresis with a 1% agarose gel, the agarose gel was soaked in an ethidium bromide solution to stain DNA in the gel, and then the stained DNA was recorded by photography. The results are shown in FIG. 37.

Lane 1 shows the results when T.th.RecA protein was added as described above.

Lane 2 shows the results when PCR was carried out in the same manner as in Lane 1 without adding the T.th.RecA protein.

As clearly shown in the results of FIG. 37, in Lane 1 in which PCR was carried out with the addition of T.th.RecA protein, amplification of the desired DNA was detected whereas byproducts were scarcely detected. Further, the signal appearing at the lower side is considered as background.

In contrast, in Lane 2 in which PCR was carried out without adding the T.th.RecA protein, amplification of the desired DNA was not detected. The reason is considered to be that the template DNA has a region of an inhibitory or suppressive secondary structure.

From these results, if PCR is carried out with the addition of T.th.RecA protein, it is possible to amplify the desired nucleic acid efficiently and specifically even when the template DNA has the region of the inhibitory or suppressive secondary structure. The reason is considered to be that the inhibitory or suppressive secondary structure is released by binding of the homologous recombinant protein to the template DNA.

Example 17

Next, Example 17 will be explained. Explanation of the parts which are similar to those of each of the above-mentioned Examples will be omitted or simplified.

Figure 38:
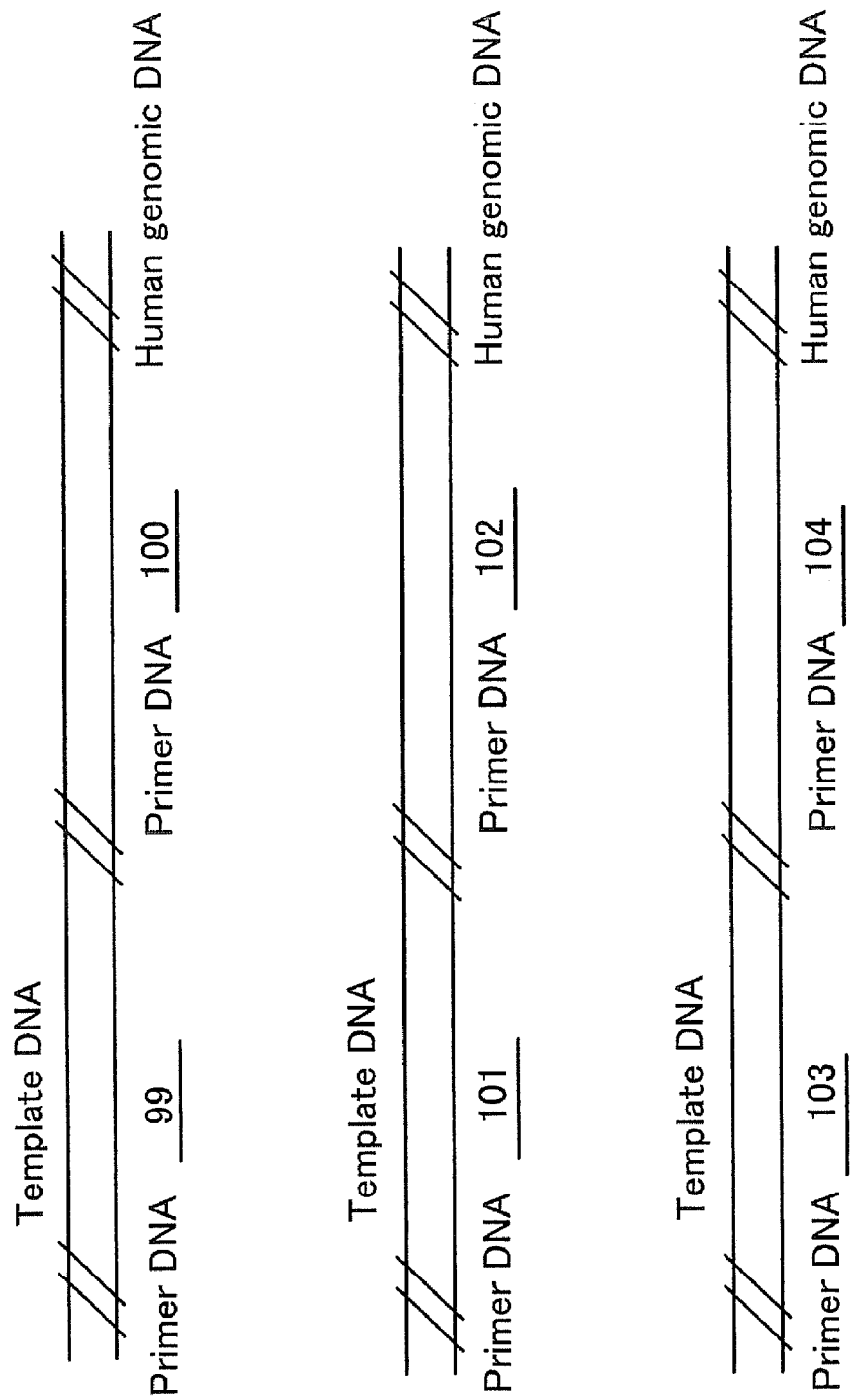
FIG. 38 is an illustrative view showing the relation between a template DNA and a primer DNA with reference to Example 17.
Figure 39:
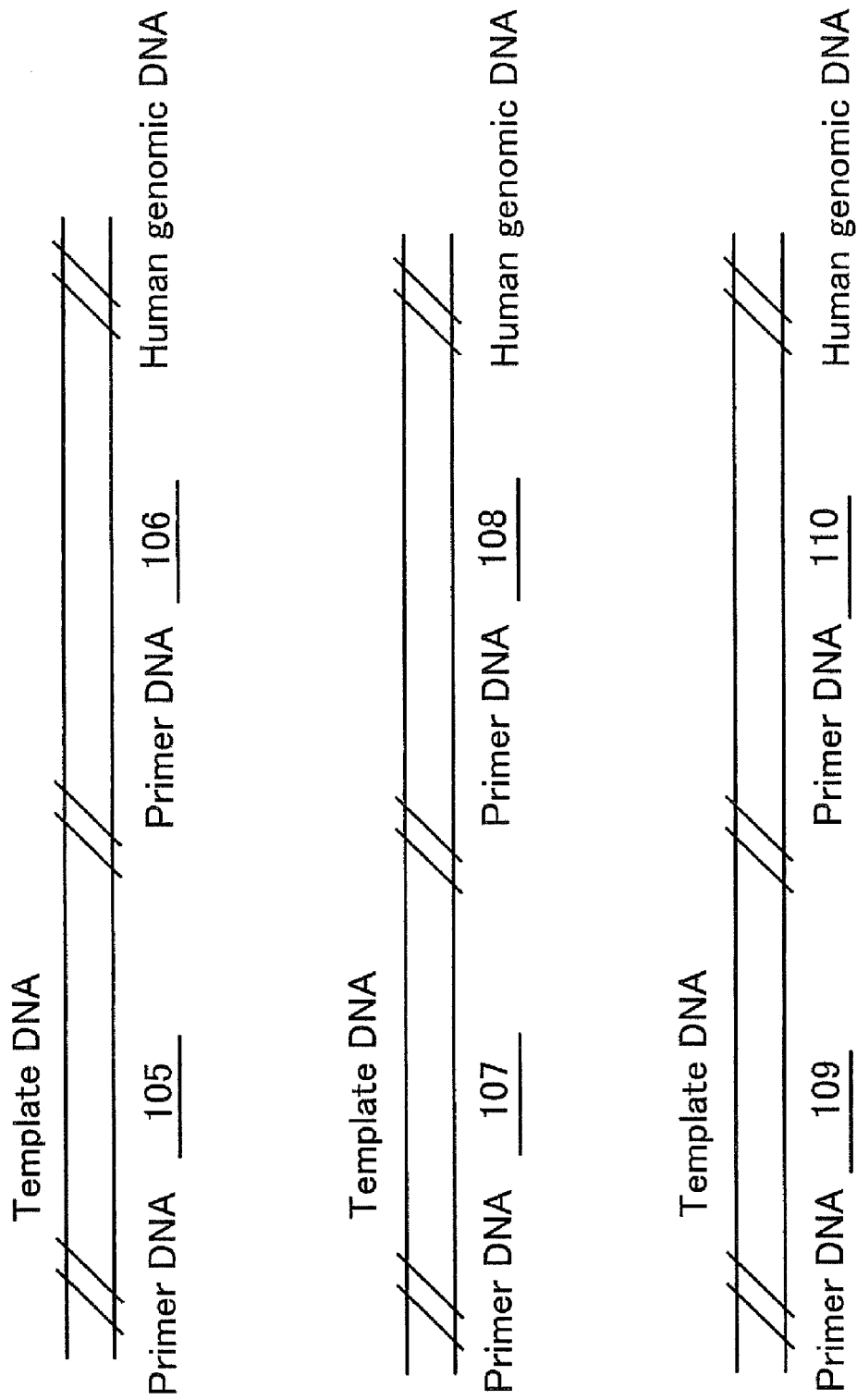
FIG. 39 is an illustrative view showing the relation between the template DNA and the primer DNA with reference to Example 17.

In this Example, as shown in FIG. 38 and FIG. 39, a human genome DNA (Promega) was prepared as a template DNA, and 12 kinds of oligonucleotides (Oligonucleotides 99 to 110) were prepared as the primer DNAs. Oligonucleotides 99 and 100 were designed with reference to Human DNA sequence from clone RP11-760M1 on chromosome 13 (Genbank accession no.; AL354815) and Human hepatocyte nuclear factor 4-alpha gene (Genbank accession no.; U72959, U72960). Oligonucleotides 101 and 102 were designed with reference to Human rhodopsin gene (Genbank accession no.; U49742, K02281). Further, Oligonucleotides 103 and 104 were designed with reference to *Homo sapiens* beta globin region (Genbank accession no.; NG000007). Further, Oligonucleotides 105 and 106 were designed with reference to *Homo sapiens* HPFH60R gene (Genbank accession no.; X81445, X91835). Further, Oligonucleotides 107 and 108 were designed with reference to Human p53 gene (Genbank accession no.; U94788). Further, Oligonucleotides 109 and 110 were designed with reference to Human p53 gene (Genbank accession no.; U94788). Each primer DNA consists of a base sequence from a 20 mer to a 27-mer, which is 100% complementary to the template DNA.

```
Oligonucleotide 99:
5'-gcatctggggcctggtatttag-3'       (SEQ ID NO: 99)

Oligonucleotide 100:
5'-tacaaggcaggcatcatgactcacg-3'   (SEQ ID NO: 100)

Oligonucleotide 101:
5'-aggagcttaggaggggaggt-3'        (SEQ ID NO: 101)

Oligonucleotide 102:
5'-cattgacaggacaggagaaggga-3'     (SEQ ID NO: 102)

Oligonucleotide 103:
5'-ctttttgttcccccagacactc-3'      (SEQ ID NO: 103)

Oligonucleotide 104:
5'-gcaatggcttaggagttggact-3'      (SEQ ID NO: 104)

Oligonucleotide 105:
5'-gttaatacctaaggctctactgca-3'    (SEQ ID NO: 105)

Oligonucleotide 106:
5'-aggcaatggcggcacccatc-3'        (SEQ ID NO: 106)

Oligonucleotide 107:
5'-gcagagacctgtgggaagcgaaaa-3'    (SEQ ID NO: 107)

Oligonucleotide 108:
5'-gagagctgtggcaagcagggga-3'      (SEQ ID NO: 108)

Oligonucleotide 109:
5'-cccctcctggcccctgtcat-3'        (SEQ ID NO: 109)

Oligonucleotide 110:
5'-gttagatgactttgcccaactgtaggg-3' (SEQ ID NO: 110)
```

Then, nucleic acids were amplified by PCR reaction. Specifically, 0.8 μM each (final concentration) of two kinds of the oligonucleotides, 200 ng of the human genome DNA (Promega), 1.0 unit of ExTaq-HS Polymerase (Takara Bio, Inc.), 0.2 mM of a dNTP mixture solution and 1.0 μg of the T.th.RecA protein, were mixed with 1XExTaq buffer (Takara Bio, Inc.) in 50 μl of a PCR reaction solution. Then, PCR was carried out with 1 cycle (at 94° C. for 30 seconds), 35 cycles (at 94° C. for 15 seconds, at 55° C. for 30 seconds, and at 72° C. for 1 minute) and 1 cycle (at 72° C. for 7 minutes, and at 4° C. for 1 minute).

Figure 40:
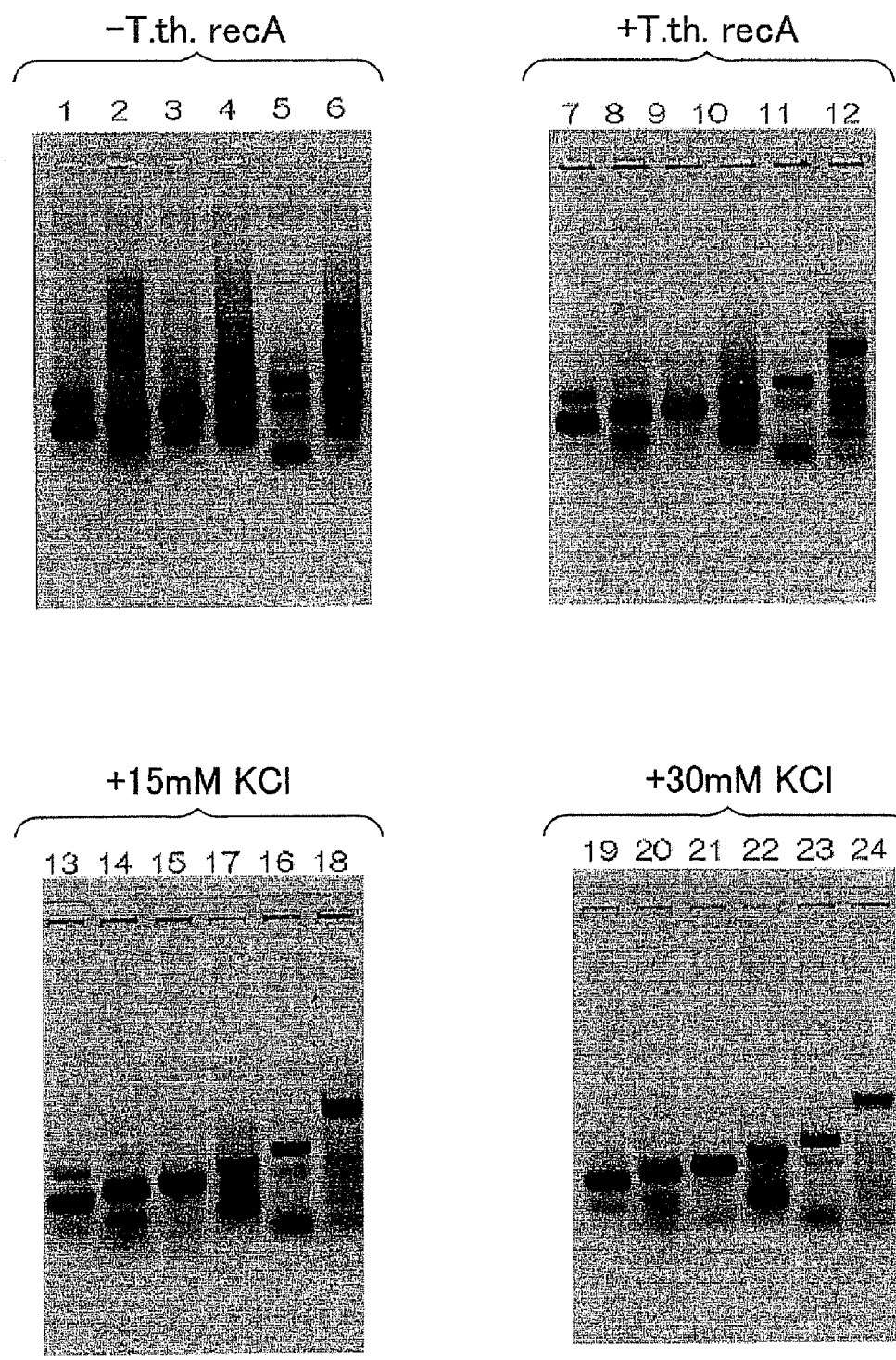
FIG. 40 is a photograph, instead of a drawing, which shows the results of the electrophoresis for the PCR reaction products with reference to Example 17.

Subsequently, 10 μl of the reaction solution was subjected to electrophoresis with 1.2% agarose gel, the agarose gel was soaked in an ethidium bromide solution to stain DNA in the gel, and then the stained DNA was recorded by photography. The results are shown in FIG. 40.

Lane 7 shows the results when Oligonucleotide 99 and Oligonucleotide 100 are added as the primer DNA.

Lane 8 shows the results when Oligonucleotide 101 and Oligonucleotide 102 were added as the primer DNAs.

Lane 9 shows the results when Oligonucleotide 103 and Oligonucleotide 104 were added as the primer DNAs.

Lane 10 shows the results when Oligonucleotide 105 and Oligonucleotide 106 were added as the primer DNAs.

Lane 11 shows the results when Oligonucleotide 107 and Oligonucleotide 108 were added as the primer DNAs.

Lane 12 shows the results when Oligonucleotide 109 and Oligonucleotide 110 are added as the primer DNA.

Lane 1 shows the results when PCR was carried out in the same manner as in Lane 7 without adding the T.th.RecA protein.

Lane 2 shows the results when PCR was carried out in the same manner as in Lane 8 without adding the T.th.RecA protein.

Lane 3 shows the results when PCR was carried out in the same manner as in Lane 9 without adding the T.th.RecA protein.

Lane 4 shows the results when PCR was carried out in the same manner as in Lane 10 without adding the T.th.RecA protein.

Lane 5 shows the results when PCR was carried out in the same manner as in Lane 11 without adding the T.th.RecA protein.

Lane 6 shows the results when PCR was carried out in the same manner as in Lane 12 without adding the T.th.RecA protein.

Lane 13 shows the results when 15 mM KCl was added and PCR was carried out in the same manner as in Lane 7.

Lane 14 shows the results when 15 mM KCl was added and PCR was carried out in the same manner as in Lane 8.

Lane 15 shows the results when 15 mM KCl was added and PCR was carried out in the same manner as in Lane 9.

Lane 16 shows the results when 15 mM KCl was added and PCR was carried out in the same manner as in Lane.

Lane 17 shows the results when 15 mM KCl was added and PCR was carried out in the same manner as in Lane 11 g.

Lane 18 shows the results when 15 mM KCl was added and PCR was carried out in the same manner as in Lane 12.

Lane 19 shows the results when 30 mM KCl was added and PCR was carried out in the same manner as in Lane 7.

Lane 20 shows the results when 30 mM KCl was added and PCR was carried out in the same manner as in Lane 8.

Lane 21 shows the results when 30 mM KCl was added and PCR was carried out in the same manner as in Lane 9.

Lane 22 shows the results when 30 mM KCl was added and PCR was carried out in the same manner as in Lane 10.

Lane 23 shows the results when 30 mM KCl was added and PCR was carried out in the same manner as in Lane 11.

Lane 24 shows the results when 30 mM KCl was added and PCR was carried out in the same manner as in Lane 12.

As clearly shown in the results of FIG. 40, in Lanes 7 to 12 in which PCR was carried out with the addition of T.th.RecA protein, amplification of the desired DNA was detected whereas byproducts were detected only slightly.

Further, in Lanes 13 to 18 in which 15 mM KCl was added, amplification of byproducts was suppressed more than in Lanes 7 to 12.

Furthermore, in Lanes 19 to 24 in which 30 mM KCl was added, amplification of byproducts was suppressed more efficiently than in Lanes 13 to 18.

In contrast, in Lanes 1 to 6 in which PCR was carried out without adding the T.th.RecA protein, amplification of the desired DNA was detected, and also byproducts were detected in a large amount.

From these results, if PCR is carried out with the addition of T.th.RecA protein, amplification of byproducts can be suppressed to low levels without decreasing the yield of the desired nucleic acid. In other words, by the presence of the homologous recombination protein, the primer extension reaction caused by binding of the primer DNAs to a non-specific region of the template DNA is suppressed, and thus it is possible to suppress amplification of non-specific PCR products.

Especially, by adding KCl to the PCR reaction solution, it is possible to increase the PCR specificity.

Example 18

Next, Example 18 will be explained. Explanation of the parts which are similar to those of each of the above-mentioned Examples will be omitted or simplified.

Figure 41:
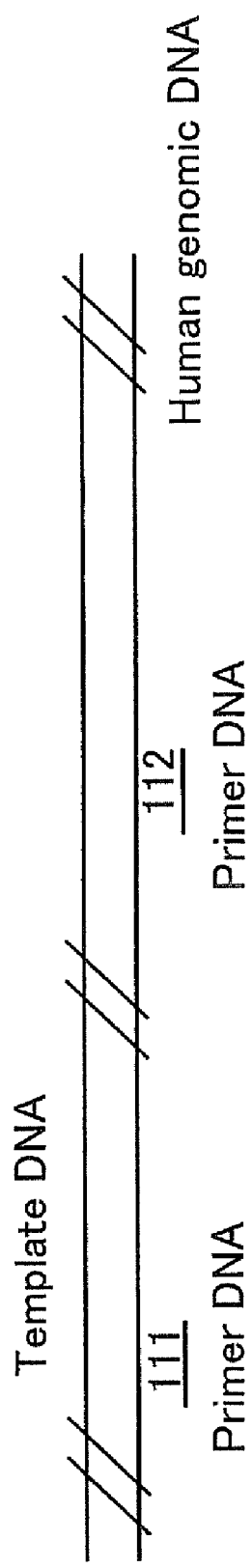
FIG. 41 is an illustrative view showing the relation between a template DNA and a primer DNA with reference to Example 18.

In this Example, as shown in FIG. 41, a human genome DNA (Promega) was prepared as a template DNA, and Oligonucleotides 111 and 112 were prepared as the primer DNAs. Each primer DNA was designed with reference to *Homo sapiens* beta globin region (Genbank accession no.; NG000007). Each primer DNA consists of a 21 mer or a 22 mer base sequence, which is 100% complementary to the template DNA.

```
Oligonucleotide 111:
5'-ctgctgaaagagatgcggtgg-3'    (SEQ ID NO:111)

Oligonucleotide 112:
5'-aggaaaacagcccaagggacag-3'   (SEQ ID NO:112)
```

Then, nucleic acids were amplified by PCR reaction. Specifically, 0.25 μM each (the final concentration) of two kinds of the oligonucleotides, 100 ng of the human genome DNA (Promega), 1.25 unit of ExTaq Polymerase (Takara Bio, Inc.), 0.2 mM of a dNTP mixture solution and 1.0 μg of the T.th.RecA protein, were mixed with 1× ExTaq buffer (Takara Bio, Inc.) in 50 μl of a PCR reaction solution. Then, PCR was carried out with 1 cycle (at 94° C. for 30 seconds), 35 cycles (at 94° C. for 15 seconds, at 55° C. for 30 seconds, and at 72° C. for 1 minute) and 1 cycle (at 72° C. for 7 minutes, and at 4° C. for 1 minute).

Figure 42:
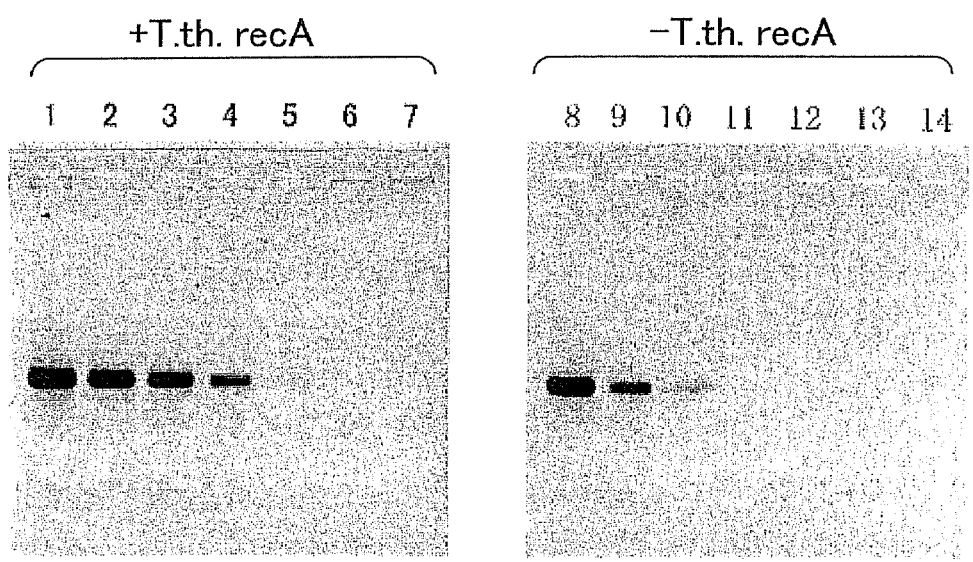
FIG. 42 is a photograph, instead of a drawing, which shows the results of the electrophoresis for the PCR reaction products with reference to Example 18.
Figure 43:
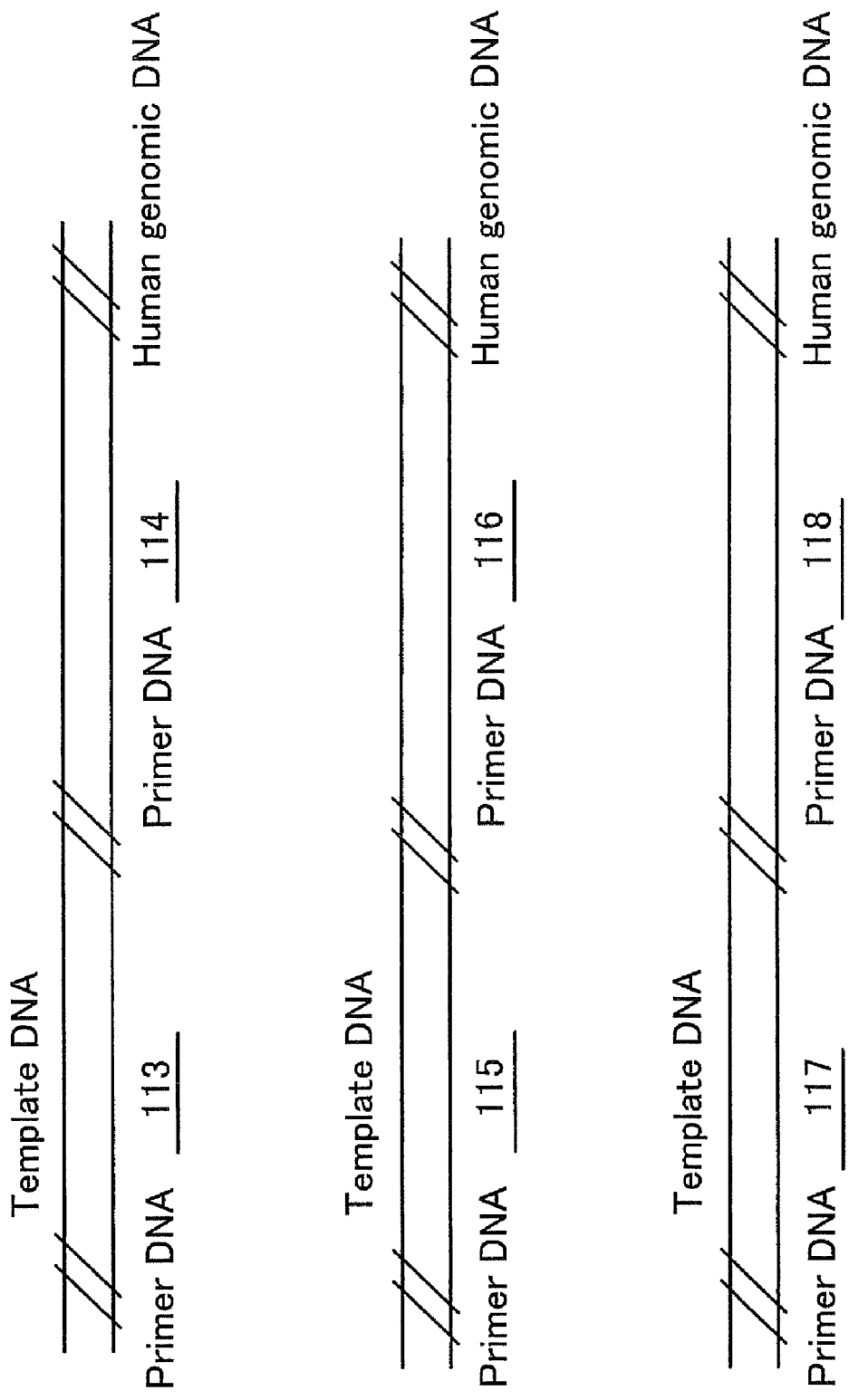
FIG. 43 is an illustrative view showing the relation between a template DNA and a primer DNA with reference to Example 19.
Figure 44:
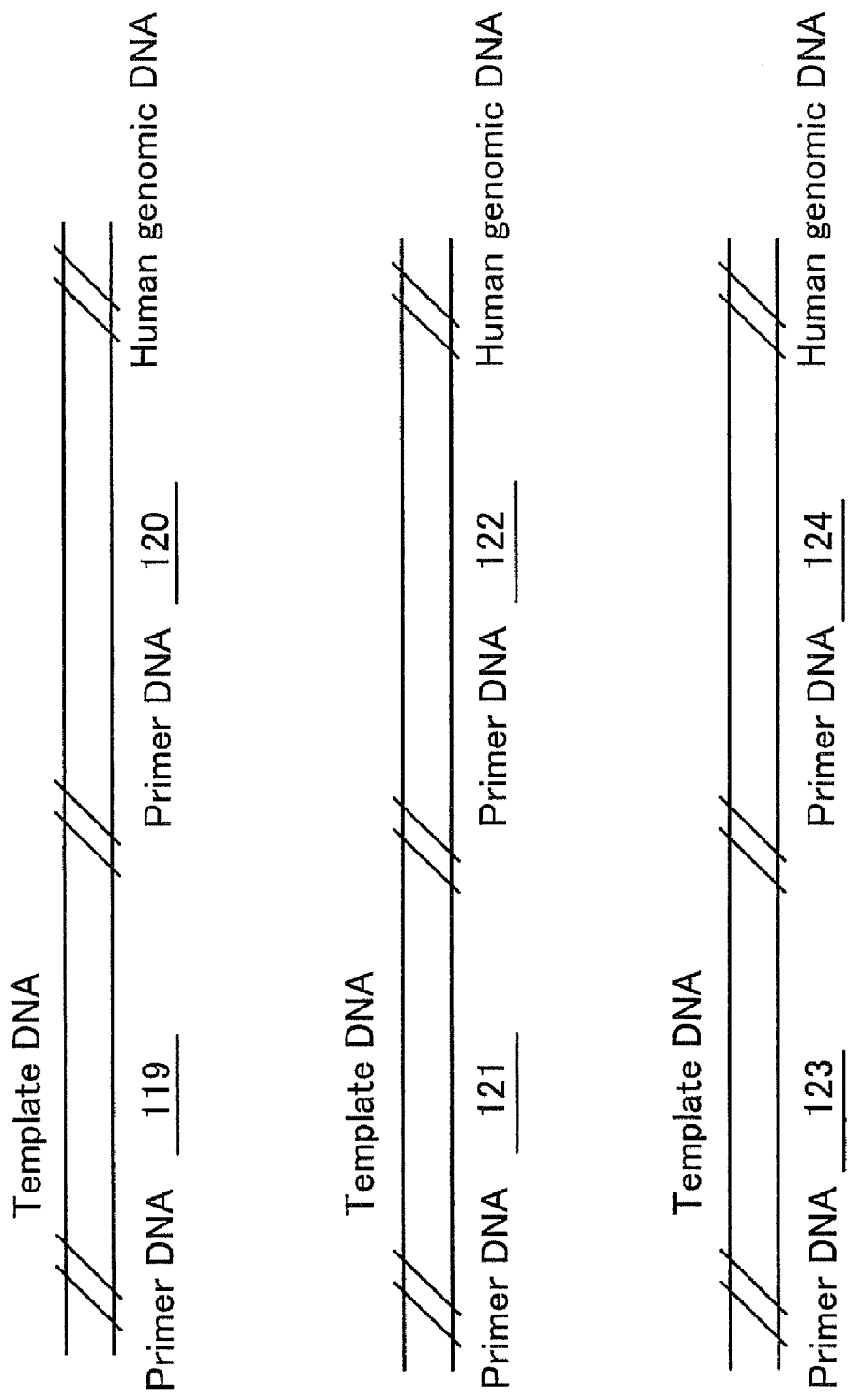
FIG. 44 is an illustrative view showing the relation between the template DNA and the primer DNA with reference to Example 19.
Figure 45:
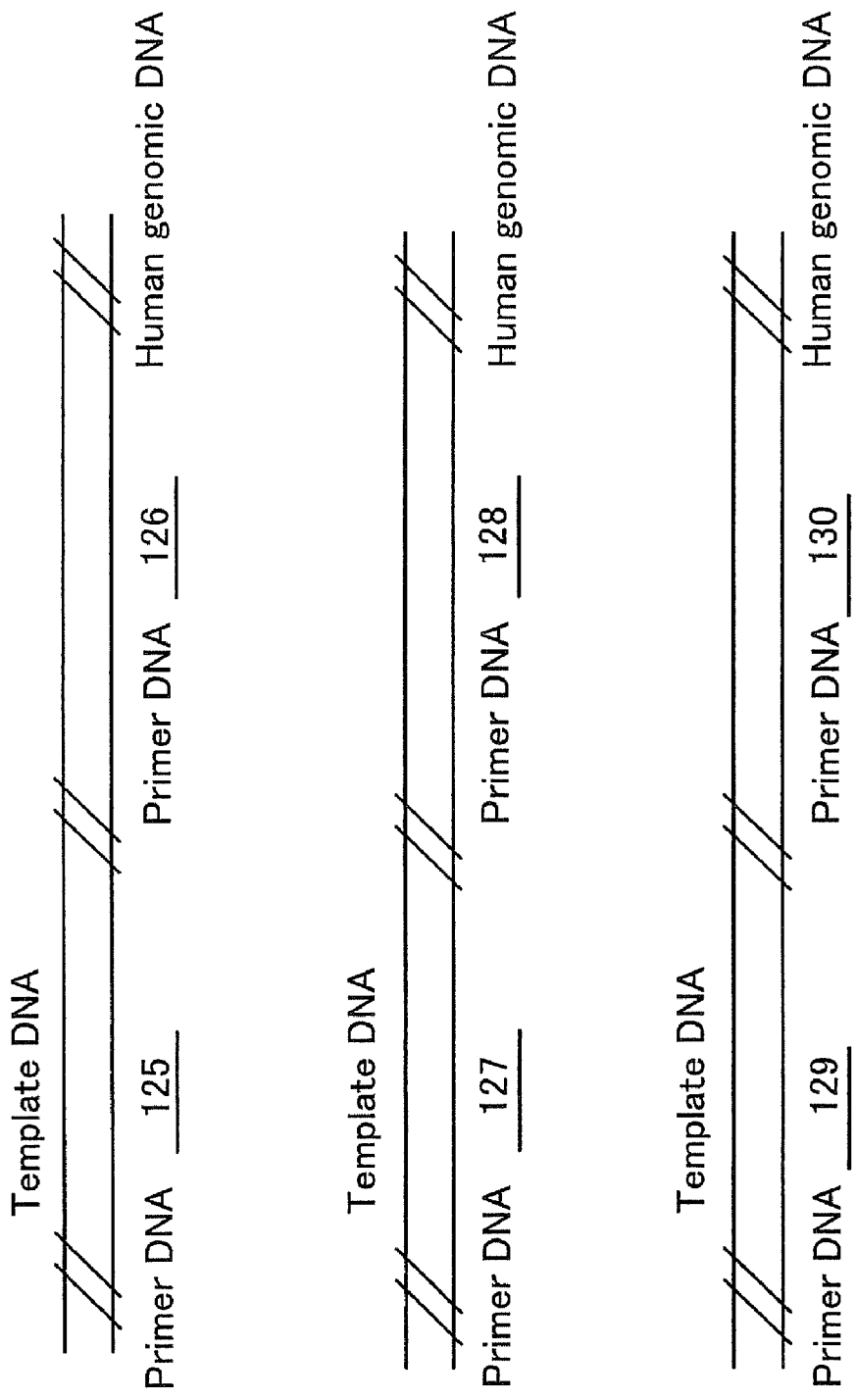
FIG. 45 is an illustrative view showing the relation between the template DNA and the primer DNA with reference to Example 19.
Figure 46:
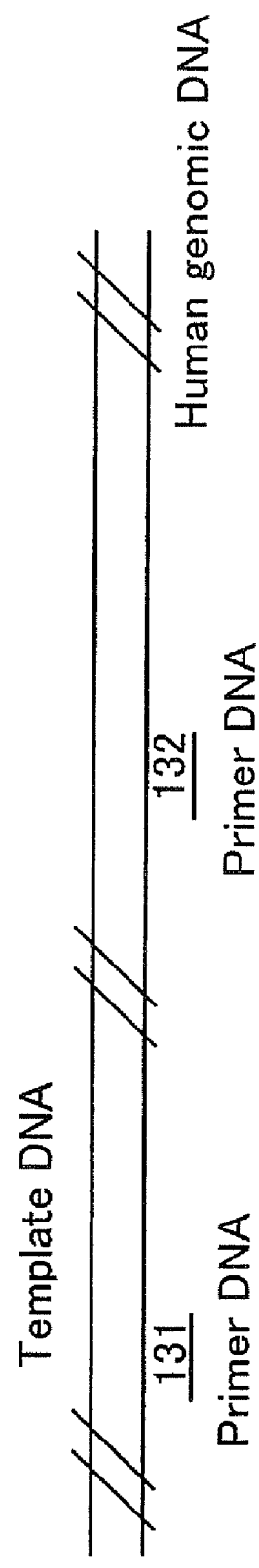
FIG. 46 is an illustrative view showing the relation between the template DNA and the primer DNA with reference to Example 19.

Subsequently, 10 μl of the reaction solution was subjected to electrophoresis with 1.2% agarose gel, the agarose gel was soaked in an ethidium bromide solution to stain DNA in the gel, and then the stained DNA was recorded by photography. The results are shown in FIG. 42.

Lane 1 shows the results when PCR was carried out with the addition of 1.25 unit of the ExTaq Polymerase.

Lane 2 shows the results when PCR was carried out in the same manner as in Lane 1 except that the ExTaq Polymerase was reduced to 0.63 unit.

Lane 3 shows the results when PCR was carried out in the same manner as in Lane 1 except that the ExTaq Polymerase was reduced to 0.31 unit.

Lane 4 shows the results when PCR was carried out in the same manner as in Lane 1 except that the ExTaq Polymerase was reduced to 0.16 unit.

Lane 5 shows the results when PCR was carried out in the same manner as in Lane 1 except that the ExTaq Polymerase was reduced to 0.08 unit.

Lane 6 shows the results when PCR was carried out in the same manner as in Lane 1 except that the ExTaq Polymerase was reduced to 0.04 unit.

Lane 7 shows the results when PCR was carried out in the same manner as in Lane 1 except that the ExTaq Polymerase was reduced to 0.02 unit.

Lane 8 shows the results when PCR was carried out in the same manner as in Lane 1 without adding the T.th.RecA protein.

Lane 9 shows the results when PCR was carried out in the same manner as in Lane 2 without adding the T.th.RecA protein.

Lane 10 shows the results when PCR was carried out in the same manner as in Lane 3 without adding the T.th.RecA protein.

Lane 11 shows the results when PCR was carried out in the same manner as in Lane 4 without adding the T.th.RecA protein.

Lane 12 shows the results when PCR was carried out in the same manner as in Lane 5 without adding the T.th.RecA protein.

Lane 13 shows the results when PCR was carried out in the same manner as in Lane 6 without adding the T.th.RecA protein.

Lane 14 shows the results when PCR was carried out in the same manner as in Lane 7 without adding the T.th.RecA protein.

As clearly shown in the results of FIG. 42, in Lanes 1 to 5 among Lanes 1 to 7 in which PCR was carried out with the addition of T.th.RecA protein, amplification of the desired DNA was detected. In other words, by adding more than 0.08 unit of ExTaq Polymerase to the PCR reaction solution, the desired DNA was amplified.

In contrast, when PCR was carried out without adding the T.th.RecA protein, amplification of the desired DNA was detected only in Lanes 8 to 10 among Lanes 8 to 14. In other words, only when more than 0.31 unit of ExTaq Polymerase was added to the PCR reaction solution, the desired DNA was amplified.

From these results, if PCR is carried out with the addition of T.th.RecA protein, the desired nucleic acid can be amplified more efficiently and specifically even if the amount of the DNA polymerase to be added is reduced. The reason is considered to be that because the homologous recombinant protein binds to the primer DNAs and to the template DNA, which promotes binding of the primer DNAs with the template DNA, PCR reaction proceeds efficiently even if the amount of the DNA polymerase to be added is reduced.

Example 19

Next, Example 19 will be explained. Explanation of the parts which are similar to those of each of the above-mentioned Examples will be omitted or simplified.

In this Example, as shown in FIG. 43 to FIG. 46, a human genome DNA (Promega) was prepared as a template DNA, and 20 kinds of oligonucleotides (Oligonucleotides 113 to 132) were prepared as the primer DNAs. Oligonucleotides 113 and 114 were designed with reference to *Homo sapiens* 16p13.3 sequence (Genbank accession no.; AE006462, AE005175). Oligonucleotides 115 and 116 were designed with reference to *Homo sapiens* SVMT gene (Genbank accession no.; AB044401). Oligonucleotides 117 and 118 were designed with reference to *Homo sapiens* HPFH60R gene (Genbank accession no.; X81445, X91835). Oligonucleotides 119 and 120 were designed with reference to Human p53 gene (Genbank accession no.; U94788). Oligonucleotides 121 and 122 were designed with reference to Human hepatocyte nuclear factor 4-alpha gene (Genbank accession no.; U72959, U72960). Oligonucleotides 123 and 124 were designed with reference to *Homo sapiens* diacylglycerol kinase (Genbank accession no.; NM_003646). Oligonucleotides 125 and 126 were designed with reference to Human rhodopsin gene (Genbank accession no.; U49742, K02281). Oligonucleotides 127 and 128 were designed with reference to Human DNA for CAAF1 (Genbank accession no.; D83657). Oligonucleotides 129 and 130 were designed with reference to *Homo sapiens* CYP21 (Genbank accession no.; M12792, M23280). Oligonucleotides 131 and 132 were designed with reference to Human S100 protein beta-subunit gene (Genbank accession no.; M59486, J05600). Each primer DNA consists of a base sequence from a 20-mer to a 26-mer, which is 100% complementary to the template DNA.

```
Oligonucleotide 113:
5'-cacagatttccaaggatgcgctg-3'        (SEQ ID NO: 113)

Oligonucleotide 114:
5'-cgtgctctgttccagacttg-3'           (SEQ ID NO: 114)

Oligonucleotide 115:
5'-cgtctggcgattgctccaaatg-3'         (SEQ ID NO: 115)

Oligonucleotide 116:
5'-gggcagttgtgatccatgagaa-3'         (SEQ ID NO: 116)

Oligonucleotide 117:
5'-ggcttgcaccagcttaggaaag-3'         (SEQ ID NO: 117)

Oligonucleotide 118:
5'-cgttaggcataatcagtgggatagt-3'      (SEQ ID NO: 118)

Oligonucleotide 119:
5'-gcctctgattcctcactgattgctct-3'     (SEQ ID NO: 119)

Oligonucleotide 120:
5'-tgtcaaccaccccttaacccctcc-3'       (SEQ ID NO: 120)

Oligonucleotide 121:
5'-ttggaggggtgggtgagtcaag-3'         (SEQ ID NO: 121)

Oligonucleotide 122:
5'-ggaggggtgggggttaatggtta-3'        (SEQ ID NO: 122)

Oligonucleotide 123:
5'-ggaacaagacacggctggtt-3'           (SEQ ID NO: 123)

Oligonucleotide 124:
5'-agcaaggcagggcaggcaagt-3'          (SEQ ID NO: 124)

Oligonucleotide 125:
5'-cggtcccattctcagggaatct-3'         (SEQ ID NO: 125)

Oligonucleotide 126:
5'-gcccagaggaagaagaaggaaa-3'         (SEQ ID NO: 126)

Oligonucleotide 127:
5'-gcccccacccaggttggtttcta-3'        (SEQ ID NO: 127)

Oligonucleotide 128:
5'-atgccttcatctggctcagtgaa-3'        (SEQ ID NO: 128)

Oligonucleotide 129:
5'-gctcagcatgctggtggcataa-3'         (SEQ ID NO: 129)

Oligonucleotide 130:
5'-cctcataccttcccccccatt-3'          (SEQ ID NO: 130)

Oligonucleotide 131:
5'-gactactctagcgactgtccatctc-3'      (SEQ ID NO: 131)

Oligonucleotide 132:
5'-gacagccaccagatccaatc-3'           (SEQ ID NO: 32)
```

Then, nucleic acids were amplified by PCR reaction. Specifically, 0.1 μM each (the final concentration) of 20 kinds of the oligonucleotides, 100 ng of the human genome DNA (Promega), 1.25 unit of ExTaq Polymerase (Takara Bio, Inc.), 0.2 mM of a dNTP mixture solution and 1.0 μg of the T.th.RecA protein, were mixed with 1× ExTaq buffer (Takara Bio, Inc.) in 50 μl of a PCR reaction solution. Then, PCR was carried out with 1 cycle (at 94° C. for 30 seconds), 35 cycles (at 94° C. for 15 seconds, at 55° C. for 30 seconds, and at 72° C. for 1 minute) and 1 cycle (at 72° C. for 7 minutes, and at 4° C. for 1 minute).

Subsequently, 10 μl of the reaction solution was subjected to electrophoresis with 1.2% agarose gel, the agarose gel was soaked in an ethidium bromide solution to stain DNA in the gel, and then the stained DNA was recorded by photography. The results are shown in FIG. 47.

As clearly shown in the results of FIG. 47, amplification of the desired DNA corresponding to each primer set was detected whereas byproducts were scarcely detected.

From these results, even if a plurality of kinds of primer DNAs are added and PCR is carried out, i.e., multi-primer-PCR is carried out, when PCR is carried out with the addition of T.th.RecA protein, it is possible to amplify the desired nucleic acid while suppressing the production of byproducts. The reason is considered to be that since the desired DNA can be amplified even if the concentration of the primer DNAs is reduced as described above when PCR is carried out with the addition of T.th.RecA protein, it is possible to amplify the desired DNA corresponding to each primer set even if multi-primer-PCR is carried out.

In the above, the embodiment modes of the present invention were illustrated by Examples, but the present invention is not limited by each of the above-mentioned Examples 1 to 19, and, needless to say, it can be suitably modified and applied without departing from the spirit or scope of the present invention.

For example, T.th.RecA protein was employed as the homologous recombinant protein in each of the above-mentioned Examples, but other ones may be employed as described above. That is, it is possible to use a modified RecA protein obtained by modification of the T.th.RecA protein and having a function similar to that of the T.th.RecA protein (modified T.th.RecA protein), or a mixture of the T.th.RecA protein and the modified T.th.RecA protein. Further, a T.th.RecA protein fragment may be used.

Further, a RecA protein other than those mentioned above may also be used, wherein the RecA protein causes the primer extension reaction only for a primer DNA having a mismatch of 3 bases or less with the template DNA. Also, it is possible to use homologous recombinant proteins comprising at least one of such RecA proteins and a modified RecA protein obtained by modification of the RecA protein and having a function similar to that of the RecA protein.

Further, if the template DNA has a region of an inhibitory or suppressive secondary structure, it is difficult to amplify efficiently and specifically the desired nucleic acid which has such a region if usual PCR is carried out.

In contrast, by applying the present invention, it is possible to amplify the desired nucleic acid efficiently and specifically even when the template DNA has the region of the inhibitory or suppressive secondary structure. The reason is considered to be that the inhibitory or suppressive secondary structure is released by binding of the homologous recombinant protein to the template DNA.

Further, in the above Examples, T.th.RecA protein which was separately extracted and purified was added to the reaction solution, and PCR was carried out. However, if *E. coli*, etc. is prepared such that it is transformed to express T.th.RecA protein and the like and then is heat-treated, this can be also used as a T.th.RecA protein. That is, this is a method of using *E. coli*, etc. which is subjected to heat treatment to inactivate proteins other than the T.th.RecA protein and the like having high heat-resistance.

Especially, when a genome DNA or a plasmid DNA of *E. coli* is used as a template DNA, the template DNA and the T.th.RecA protein can be obtained at the same time by heat treatment of *E. coli*, etc. that express T.th.RecA protein and the like, and thereby working efficiency for carrying out PCR can be improved.

As described above, the present invention provides a nucleic acid amplification method for amplifying a desired nucleic acid while suppressing amplification of byproducts in a PCR reaction, a reagent kit for amplifying nucleic acids, which can amplify the desired nucleic acid while suppressing amplification of byproducts in a PCR reaction, a method of detecting single nucleotide polymorphism, which utilizes that the desired nucleic acid can be amplified while suppressing amplification of byproducts in a PCR reaction, and a reagent kit for detecting single nucleotide polymorphism, which utilizes that the desired nucleic acid can be amplified while suppressing amplification of byproducts in a PCR reaction.

What is claimed is:

1. A method of detecting single nucleotide polymorphism, comprising
admixing in a reaction solution, a homologous recombinant protein which contains at least one of a RecA protein derived from *Thermus thermophilus*, and a modified RecA protein obtained by modification of the RecA protein and having a function similar to that of the RecA protein, and
carrying out PCR, by using a primer DNA corresponding to a sequence containing a base which forms single nucleotide polymorphism in a template DNA, to detect single nucleotide polymorphism by amplifying a desired nucleic acid;
wherein ATP-γS is added to the reaction solution; and
wherein the single nucleotide polymorphism is at a base other than the base corresponding to the 3' end of the primer.

2. The method of detecting single nucleotide polymorphism according to claim 1, comprising adding KCl to the reaction solution.

3. The method of detecting single nucleotide polymorphism according to claim 1, comprising adding Mg2+ to the reaction solution.

4. A method of detecting single nucleotide polymorphism, comprising
admixing in a reaction solution, a homologous recombinant protein which contains at least one of a RecA protein derived from *Thermus thermophilus*, and a modified RecA protein obtained by modification of the RecA protein and having a function similar to that of the RecA protein, and
carrying out PCR, by using a primer DNA corresponding to a sequence containing a base which forms single nucleotide polymorphism in a template DNA, to detect single nucleotide polymorphism by amplifying a desired nucleic acid;
wherein ATP-γS is added to the reaction solution, and
wherein the single nucleotide polymorphism is at a base corresponding to any one of the 2nd to the 11th base from the 3' end of the primer.

5. The method of claim 4, wherein the mismatch is at a base corresponding to any one of the 3rd to the 11th base from the 3' end of the primer.

6. The method of claim 5, wherein the mismatch is at a base corresponding to the 3rd, 4th, or 11th base from the 3' end of the primer.

* * * * *